(12) United States Patent
Bangera et al.

(10) Patent No.: US 9,717,618 B2
(45) Date of Patent: Aug. 1, 2017

(54) GASTROINTESTINAL DEVICE WITH ASSOCIATED COMMENSAL MICROBES

(71) Applicant: Elwha LLC, Bellevue, WA (US)

(72) Inventors: Mahalaxmi Gita Bangera, Renton, WA (US); William David Duncan, Mill Creek, WA (US); Roderick A. Hyde, Redmond, WA (US); Wayne R. Kindsvogel, Seattle, WA (US); Elizabeth A. Sweeney, Seattle, WA (US)

(73) Assignee: Elwha LLC, Bellevue, WA (US)

( * ) Notice: Subject to any disclaimer, the term of this patent is extended or adjusted under 35 U.S.C. 154(b) by 171 days.

(21) Appl. No.: 14/471,169

(22) Filed: Aug. 28, 2014

(65) Prior Publication Data

US 2016/0058591 A1    Mar. 3, 2016

(51) Int. Cl.
*A61B 19/00*      (2006.01)
*A61F 5/00*      (2006.01)
*A61F 2/04*      (2013.01)
*A61L 27/54*      (2006.01)
*A61L 29/14*      (2006.01)
(Continued)

(52) U.S. Cl.
CPC .............. *A61F 5/0076* (2013.01); *A61F 2/04* (2013.01); *A61K 35/741* (2013.01); *A61K 35/745* (2013.01); *A61K 35/747* (2013.01); *A61K 38/168* (2013.01); *A61L 27/54* (2013.01); *A61L 29/08* (2013.01); *A61L 29/148* (2013.01); *A61L 29/16* (2013.01); *A61L 31/005* (2013.01); *A61L 31/048* (2013.01); *A61L 31/06* (2013.01); *A61L 31/10* (2013.01); *A61L 31/145* (2013.01); *A61L 31/148* (2013.01); *A61L 31/16* (2013.01); *A61F 2002/045* (2013.01); *A61F 2210/0004* (2013.01); *A61F 2210/0057* (2013.01); *A61F 2210/0076* (2013.01); *A61F 2220/0016* (2013.01); *A61F 2240/001* (2013.01); *A61K 2035/115* (2013.01); *A61L 2300/252* (2013.01); *A61L 2300/604* (2013.01);
(Continued)

(58) Field of Classification Search
CPC ..... A61F 5/0076; A61F 5/0036; A61K 35/74; A61L 29/16
USPC .......................................................... 604/8
See application file for complete search history.

(56) References Cited

U.S. PATENT DOCUMENTS 3,331,772 A    7/1967    Brownscombe et al.
5,275,766 A    1/1994    Gadkaree et al.
(Continued)

OTHER PUBLICATIONS

PCT International Search Report; International App. No. PCT/US2015/046650; Dec. 1, 2015; pp. 1-3.
(Continued)

*Primary Examiner* — Leslie Deak

(57) ABSTRACT

A gastrointestinal device and methods of manufacturing said gastrointestinal device are described and include a flexible tubular structure including an inner surface and an outer surface, a plurality of at least one type of commensal microbe associated with at least a portion of at least one of the inner surface and the outer surface, and a proximal end and a distal end, the proximal end and the distal end forming a flow conduit through the flexible tubular structure; and at least one anchor structure including one or more gastric wall-engaging components configured to engage a wall of the gastrointestinal tract of the subject.

32 Claims, 35 Drawing Sheets

(51) Int. Cl.
| | |
|---|---|
| *A61L 29/16* | (2006.01) |
| *A61K 35/741* | (2015.01) |
| *A61L 29/08* | (2006.01) |
| *A61L 31/00* | (2006.01) |
| *A61L 31/04* | (2006.01) |
| *A61L 31/06* | (2006.01) |
| *A61L 31/10* | (2006.01) |
| *A61L 31/14* | (2006.01) |
| *A61L 31/16* | (2006.01) |
| *A61K 38/16* | (2006.01) |
| *A61K 35/745* | (2015.01) |
| *A61K 35/747* | (2015.01) |
| *A61K 35/00* | (2006.01) |

(52) U.S. Cl.
CPC ....... *A61L 2300/62* (2013.01); *A61L 2420/02* (2013.01); *A61L 2420/06* (2013.01)

(56) References Cited

U.S. PATENT DOCUMENTS

| | | | |
|---|---|---|---|
| 5,662,713 | A | 9/1997 | Andersen et al. |
| 7,025,791 | B2 | 4/2006 | Levine et al. |
| 7,037,344 | B2 | 5/2006 | Kagan et al. |
| 7,101,565 | B2 | 9/2006 | Monte |
| 7,976,488 | B2 | 7/2011 | Levine et al. |
| 7,998,060 | B2 | 8/2011 | Ferren et al. |
| 8,282,561 | B2 | 10/2012 | Towe |
| 8,753,387 | B2 | 6/2014 | Headley et al. |
| 8,753,407 | B2 | 6/2014 | Nguyen |
| 2005/0049718 | A1* | 3/2005 | Dann ............... A61F 5/0076 623/23.65 |
| 2008/0060995 | A1 | 3/2008 | Zhang et al. |
| 2011/0021888 | A1 | 1/2011 | Sing et al. |
| 2012/0158026 | A1 | 6/2012 | Behan |
| 2012/0184893 | A1 | 7/2012 | Thompson et al. |
| 2012/0232460 | A1* | 9/2012 | Raven ............... A61B 5/0031 604/9 |
| 2013/0030351 | A1* | 1/2013 | Belhe ............... A61F 5/0076 604/9 |
| 2013/0131765 | A1 | 5/2013 | Polkinghorne et al. |
| 2013/0281911 | A1 | 10/2013 | Babkes et al. |
| 2013/0331759 | A1 | 12/2013 | Neisz et al. |
| 2014/0012178 | A1 | 1/2014 | Chin |
| 2014/0200502 | A1* | 7/2014 | Belhe ............... A61F 5/0076 604/8 |
| 2015/0265660 | A1* | 9/2015 | Kaznessis ........... A01N 63/00 424/93.4 |

OTHER PUBLICATIONS

Allegretti et al.; "Restoring the gut microbiome for the treatment of inflammatory bowel diseases"; World Journal of Gastroenterology; Apr. 7, 2014; pp. 3468-3474; vol. 20, Issue 13; Baishideng Publishing Group Co.

Andersson et al.; "Comparative Analysis of Human Gut Microbiota by Barcoded Pyrosequencing"; Plos One; Jul. 2008; pp. 1-8; vol. 3, Issue 7.

Bakken et al.; "Treating Clostridium difficile Infection with Fecal Microbiota Transplantation"; National Institutes of Health Public Access; Dec. 2011; pp. 1-13; vol. 9, Issue 12; Elsevier Inc.

Baxter et al.; "Structure of the gut microbiome following colonization with human feces determines colonic tumor burden"; Microbiome; bearing a date of Mar. 5, 2014; pp. 1-11; vol. 2, Issue 20; BioMed Central Ltd.

Borody et al.; "Fecal Microbiota Transplantation: Indications, Methods, Evidence, and Future Directions"; Curr Gastroenterol Rep; Accessed on Jun. 23, 2014; pp. 1-7; vol. 15, Issue 337.

Cox et al.; "Pathways in Microbe-Induced Obesity"; National Institutes of Health Public Access; Jun. 4, 2013; pp. 1-21; vol. 17, Issue 6; Elsevier Inc.

Damaskos et al.; "Probiotics and prebiotics in inflammatory bowel disease: microflora 'on the scope'"; British Journal of Clinical Pharmacology; bearing a date of Sep. 11, 2007; pp. 453-467; vol. 65, Issue 4; Blackwell Publishing Ltd.

Derrien et al.; "Mucin-bacterial interactions in the human oral cavity and digestive tract"; Gut Microbes; Jul./Aug. 2010; pp. 254-268; vol. 1, Issue 4; Landes Bioscience.

Di Bella et al.; "Fecal microbiota transplantation: the state of the art"; Infectious Disease Reports 2013; bearing a date of Jun. 4, 2013; pp. 43-45; vol. 5, Issue e13.

Escalona et al.; "Weight Loss and Metabolic Improvement in Morbidly Obese Subjects Implanted for 1 Year With an Endoscopic Duodenal-Jejunal Bypass Liner"; Annals of Surgery; Jun. 2012; pp. 1080-1085; vol. 255, Issue 6; Lippincott Williams & Wilkins.

Espinet-Coll et al.; "Current endoscopic techniques in the treatment of obesity"; Revista Española De Enfermedades Digestivas; Accessed on Aug. 8, 2014; pp. 72-87; vol. 104, Issue 2; Arán Ediciones, S.L.

Fan et al.; Structures in *Bacillus subtilis* Are Recognized by CD14 in a Lipopolysaccharide Binding Protein-Dependent Reaction; Infection and Immunity; Jun. 1999; pp. 2964-2968; vol. 64, Issue 6; American Society for Microbiology.

Fujii et al.; "Culturing intestinal stem cells: applications for colorectal cancer research"; Frontiers in Genetics; Jun. 5, 2014; pp. 1-5; vol. 5, Article 169.

Gauglitz et al.; "Host Defence Against *Candida albicans* and the Role of Pattern-recognition Receptors"; Acta Derm Venereol; bearing a date of Aug. 15, 2011; pp. 291-300; vol. 92; Acta Dermato-Venereologica.

Gomes et al.; "Natural and Genetically Engineered Proteins for Tissue Engineering"; National Institutes of Health Public Access; bearing a date of Jan. 1, 2012; pp. 1-32; vol. 37, Issue 1; Elsevier Ltd.

Grover et al.; "Probiotics for human health—new innovations and emerging trends"; Gut Pathogens; bearing a date of Nov. 13, 2012; pp. 1-14; vol. 4, Issue 15; BioMed Central Ltd.

Hamilton et al.; "High-thoughput DNA sequence analysis reveals stable engraftment of gut microbiota following transplantation of previously frozen fecal bacteria"; Gut Microbes; Mar./Apr. 2013; pp. 125-135; vol. 4, Issue 2; Landes Bioscience.

Hardy et al.; "Probiotics, Prebiotics and Immunomodulation of Gut Mucosal Defences: Homeostasis and Immunopathology"; Nutrients 2013; bearing a date of Mar. 5, 2013; pp. 1869-1912.

Harley et al.; "Obesity and the gut microbiome: Striving for causality"; Molecular Metabolism; bearing a date of Jun. 10, 2012; pp. 21-31; vol. 1; Elsevier GmbH.

Hoffman et al.; "Archaea and Fungi of the Human Gut Microbiome: Correlations with Diet and Bacterial Residents"; PLOS One; Jun. 2013; pp. 1-12; vol. 8, Issue 6.

Kadooka et al.; "Regulation of abdominal adiposity by probiotics (*Lactobacillus gasseri* SBT2055) in adults with obese tendencies in a randomized controlled trial"; European Journal of Clinical Nutrition; bearing a date of Aug. 14, 2009; pp. 636-643; vol. 64; Macmillan Publishers Limited.

Kong et al.; "Controlling Rigidity and Degradation of Alginate Hydrogels via Molecular Weight Distribution"; Biomacromolecules; bearing a date of Feb. 25, 2004; pp. 1720-1727; vol. 5; American Chemical Society.

Kubinak et al.; "Toll-Like Receptors Promote Mutually Beneficial Commensal-Host Interactions"; PLOS Pathogens; Jul. 2012; pp. 1-3; vol. 8, Issue 7.

Kumar et al.; "AnimalLectinDb: An integrated animal lectin database"; Bioinformation—Discovery at the interface of physical and biological sciences; bearing a date of Feb. 25, 2011; pp. 134-136; vol. 6, Issue 3; Biomedical Informatics.

Lawley et al.; "Targeted Restoration of the Intestinal Microbiota with a Simple, Defined Bacteriotherapy Resolves Relapsing *Clostridium difficile* Disease in Mice"; PLOS Pathogens; Oct. 2012; pp. 1-14; vol. 8, Issue 10.

Lieleg et al.; "Biological Hydrogels as Selective Diffusion Barriers"; National Institutes of Health Public Access; Trends Cell Biol.; bearing a date of Sep. 2011; pp. 1-19; vol. 21, Issue 9.

(56) References Cited

OTHER PUBLICATIONS

Lin et al.; "Hydrogels in controlled release formulations: Network design and mathematical modeling"; Science Direct—Advanced Drug Delivery Reviews; bearing a date of Aug. 15, 2006; pp. 1379-1408; Elsevier B.V.
Lotfipour et al.; "Evaluation of the effect of $CaCl_2$ and alginate concentrations and hardening time on the characteristics of *Lactobacillus acidophilus* loaded alginate beads using response surface analysis"; Advanced Pharmaceutical Bulletin; bearing a date of Feb. 10, 2012; pp. 71-78; vol. 2, Issue 1; Tabriz University of Medical Sciences.
Makadia et al.; "Poly Lactic-co-Glycolic Acid (PLGA) as Biodegradable Controlled Drug Delivery Carrier"; Polymers; bearing a date of Aug. 26, 2011; pp. 1377-1397; vol. 3.
Marzorati et al.; The HMI™ module: a new tool to study the Host-Microbiota Interaction in the human gastrointestinal tract in vitro; BMC Microbiology Methodology Article; bearing a date of May 22, 2014; pp. 1-14; vol. 14, Issue 133; BioMed Central Ltd.
Mattar et al.; "Probiotics up-regulate MUC-2 mucin gene expression in a Caco-2 cell-culture model"; Pediatr Surg. Int; bearing a date of Sep. 21, 2002; pp. 586-590; Springer-Verlag.
Maynard et al.; "Reciprocal interactions of the intestinal microbiota and immune system"; Nature; Sep. 13, 2012; pp. 231-241; vol. 489.
Miyata et al.; "Tumor marker-responsive behavior of gels prepared by biomolecular imprinting"; PNAS; Jan. 31, 2006; pp. 1190-1193; vol. 103, Issue 5; The National Academy of Sciences of the USA.
Modlin et al.; "Innate Immunity: Ignored for decades, but not forgotten"; National Institutes of Health Public Access; J. Invest Dermatol; bearing a date of Mar. 2012; vol. 132, Issue 3; pp. 1-9.
Moreno-Indias et al.; "Impact of the gut microbiota on the development of obesity and type 2 diabetes mellitus"; Frontiers in Microbiology; Apr. 2014; pp. 1-10; vol. 5, Issue 190.
Morowitz et al.; "Contributions of Intestinal Bacteria to Nutrition and Metabolism in the Critically Ill"; National Institutes of Health Public Access; Surg Clin North Am.; bearing a date of Aug. 2011; pp. 1-15; vol. 91, Issue 4; Elsevier Inc.
Neumann et al.; "Differences in signalling by directly and indirectly binding ligands in bacterial chemotaxis"; The EMBO Journal; bearing a date of Sep. 10, 2010; pp. 3484-3495; vol. 29, Issue 20; European Molecular Biology Organization.
Ouwehand et al.; "[13] Microbial Interactions to Intestinal Mucosal Models"; Methods in Enzymology; accessed on Aug. 8, 2014; pp. 200-212; vol. 337; Academic Press.
"Polyethylene-co-vinyl acetate 70:30 (wt) MW 55,000"; located at http://www.polysciences.com/Catalog/Department/Product/98/categoryid--286/productid--3186/search--polyethylene-co-vinyl/; Polysciences Inc.; printed on Jul. 28, 2014; pp. 1-2.
Rohde et al.; "Effect of the EndoBarrier Gastrointestinal Liner on obesity and type 2 diabetes: protocol for systematic review and meta-analysis of clinical studies"; BMJ Open; downloaded Jun. 11, 2014; pp. 1-5; vol. 3; group.bmj.com.
Schmaljohann, Dirk; "Thermo- and pH-responsive polymers in drug delivery"; ScienceDirect—Advanced Drug Delivery Reviews; bearing a date of Oct. 18, 2006; pp. 1655-1670; vol. 58; Elsevier B.V.
Tilg et al.; "Gut microbiome, obesity, and metabolic dysfunction"; The Journal of Clinical Investigation; Jun. 2011; pp. 2126-2132; vol. 121, Issue 6.
Urgesi et al.; "A randomized double-blind placebo-controlled clinical trial on efficacy and safety of association of simethicone and *Bacillus coagulans* (Colinox®) in patients with irritable bowel syndrome"; European Review for Medical and Pharmacological Sciences; accessed on Jun. 23, 2014; pp. 1344-1353; vol. 18.
Van Boeckel et al.; "Fully covered self-expandable metal stents (SEMS), partially covered SEMS and self-expandable plastic stents for the treatment of benign esophageal ruptures and anastomotic leaks"; BMC Gastroenterology; accessed Jun. 23, 2014; pp. 1-7; vol. 12, Issue 19; BioMed Central Ltd.
Van Tassell et al.; "*Lactobacillus* Adhesion to Mucus"; Nutrients; bearing a date of May 20, 2011; pp. 613-636.
Vert et al.; "Terminology for biorelated polymers and applications (IUPAC Recommendations 2012)"; Pure Appl. Chem.; Jan. 11, 2012; pp. 377-410; vol. 84, Issue 2; IUPAC.
Wang et al.; "Upper gastrointestinal microbiota and digestive diseases"; World of Gastroenterology; Mar. 14, 2013; pp. 1541-1550; vol. 19, Issue 10; Baishindeng.
Wu et al.; "Analysis of the Human Gut Microbiome and Association With Disease"; Clinical Gastroenterology and Hepatology—Advances in Translational Science; accessed on Jun. 23, 2014; pp. 774-777.
Wu et al.; "The role of gut microbiota in immune homeostasis and autoimmunity"; Gut Microbes; Jan./Feb. 2012; pp. 4-14; vol. 3, Issue 1; Landes Bioscience.
Yang et al.; "Engineering Target-Responsive Hydrogels Based on Aptamer-Target Interactions"; J. Am. Chem. Soc.; Apr. 29, 2008; pp. 6320-6321; vol. 130, Issue 20; American Chemical Society.
Zoetendal et al.; "The human small intestinal microbiota is driven by rapid uptake and conversion of simple carbohydrates"; The ISME Journal; bearing a date of Jan. 19, 2012; pp. 1415-1426; vol. 6; International Society for Microbial Ecology.

\* cited by examiner

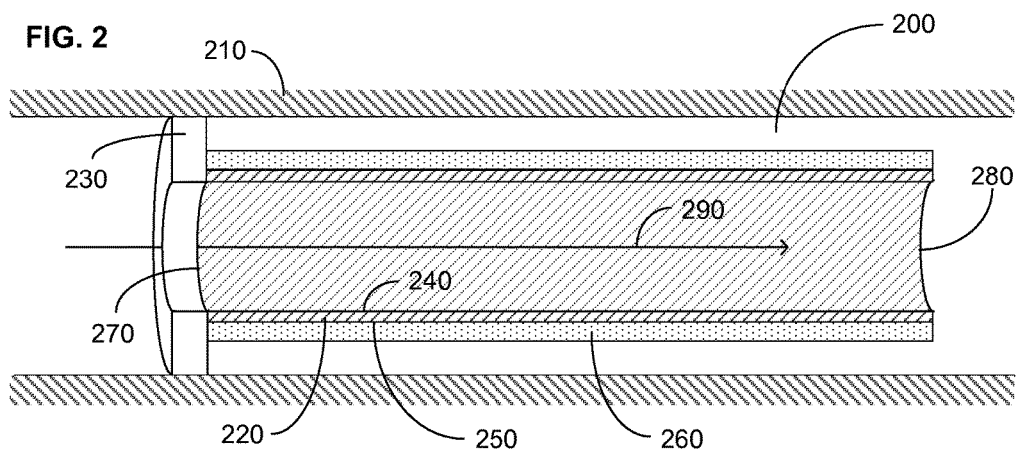
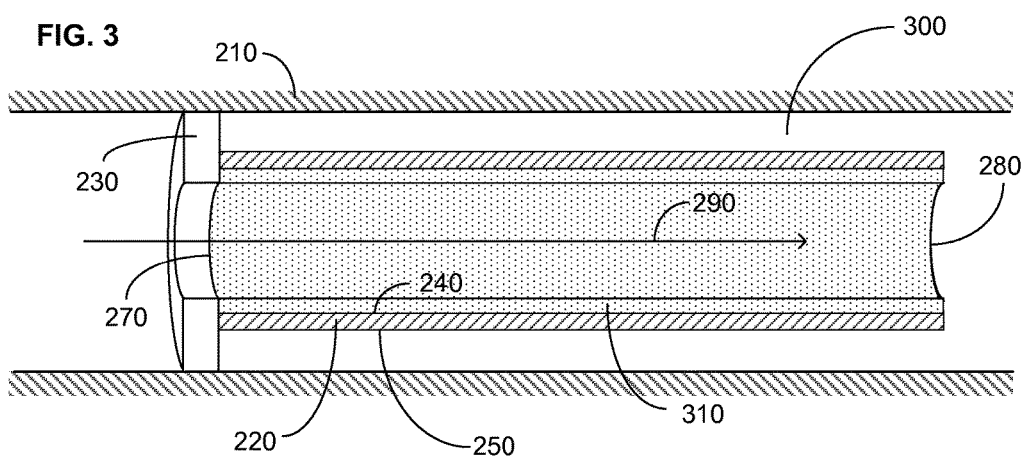
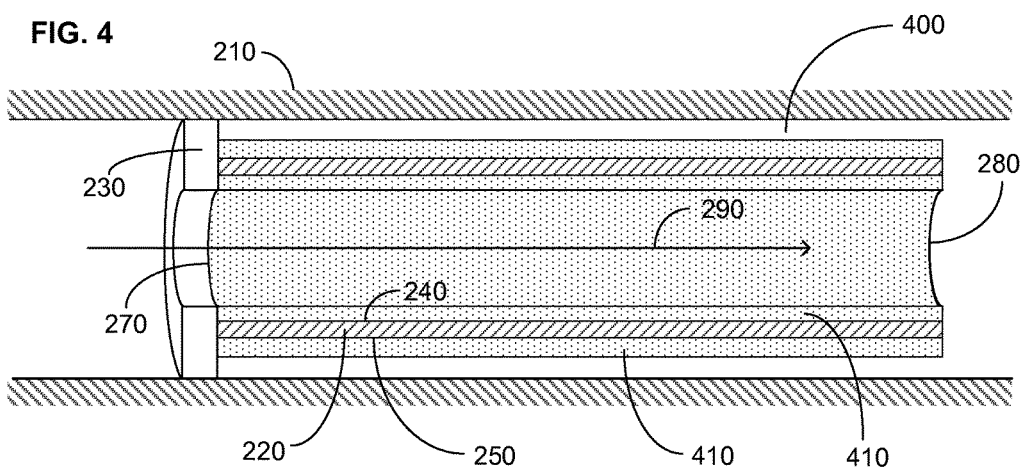

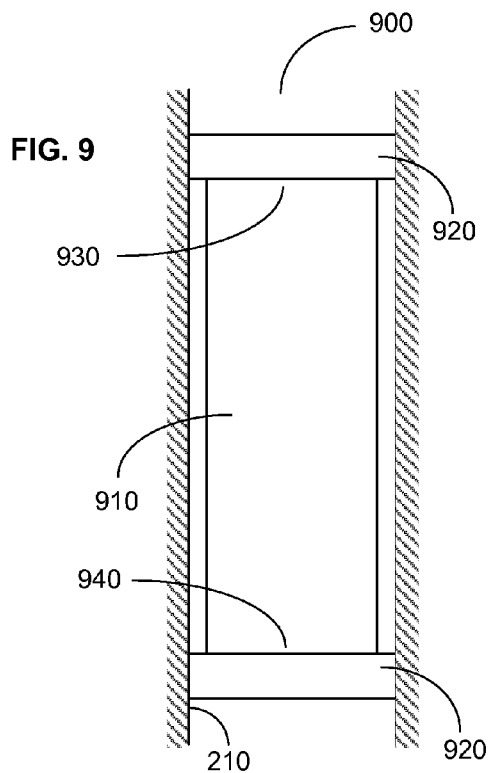
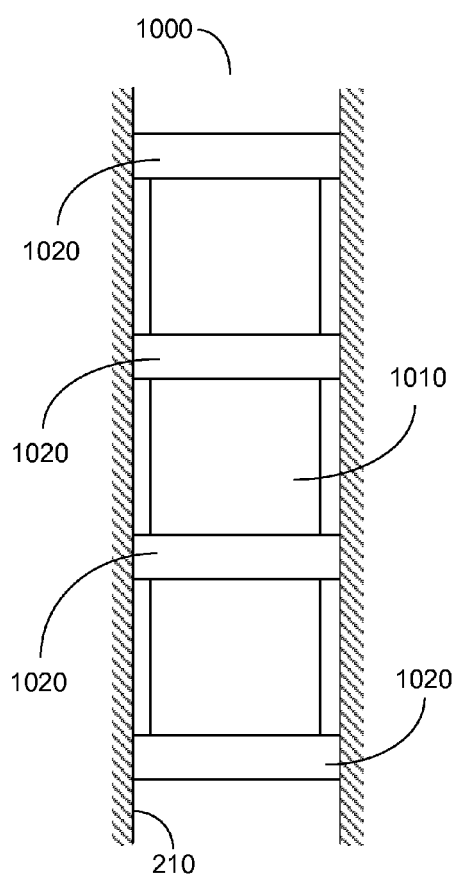
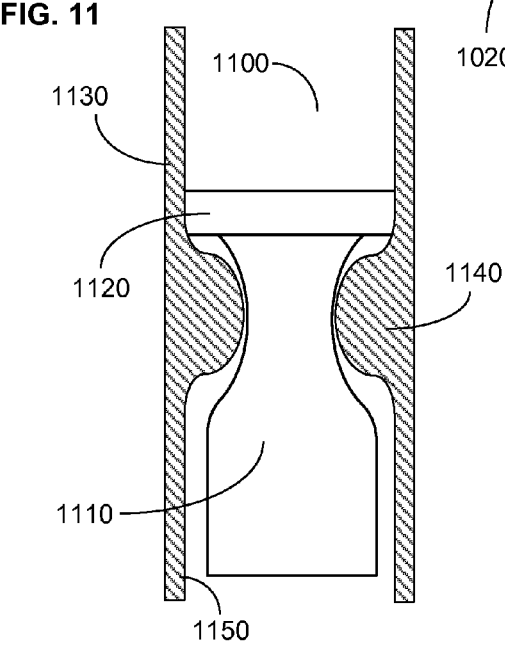

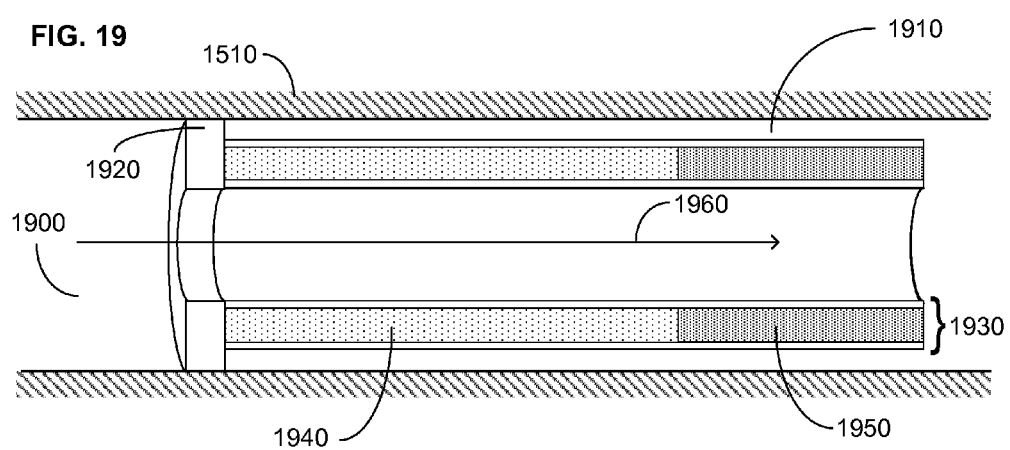
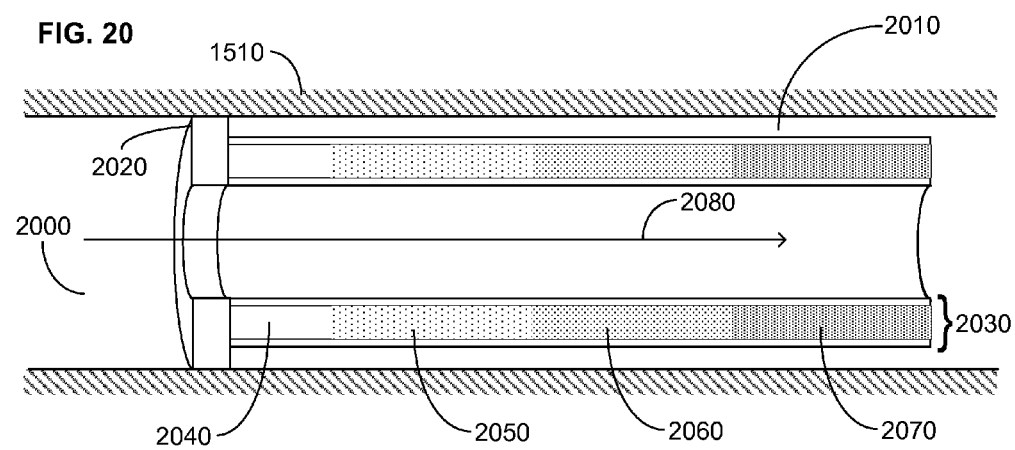

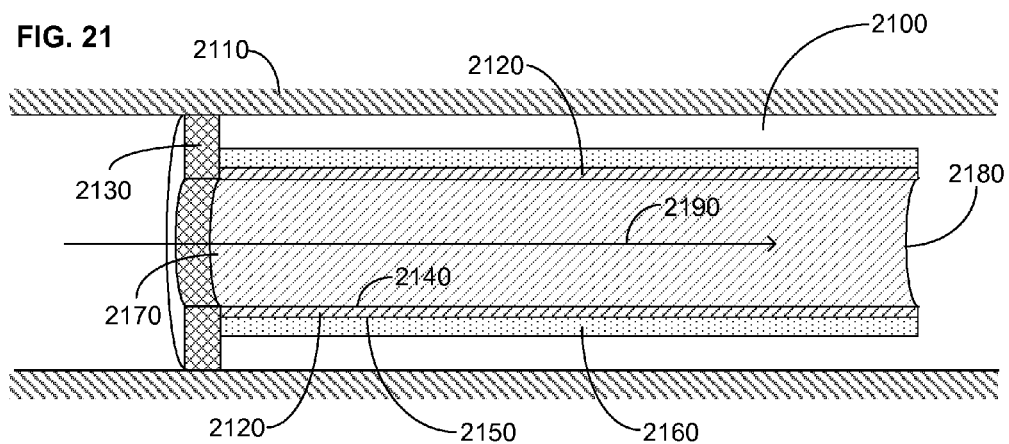
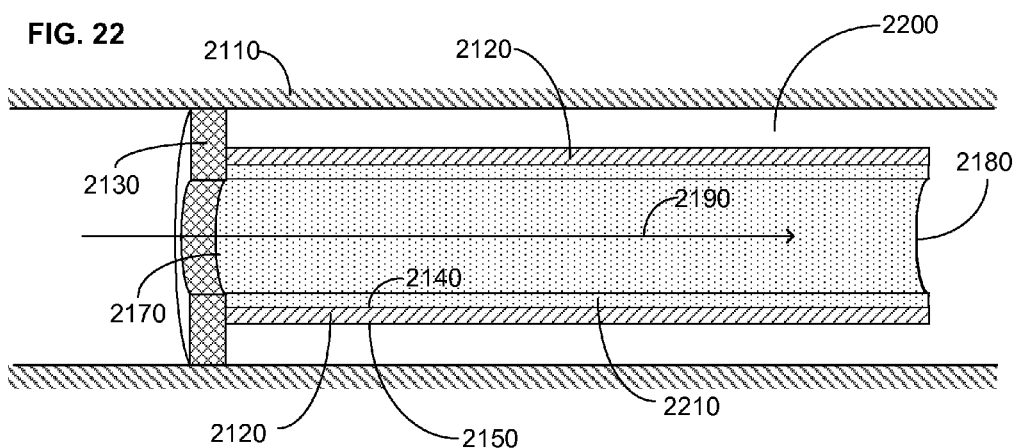
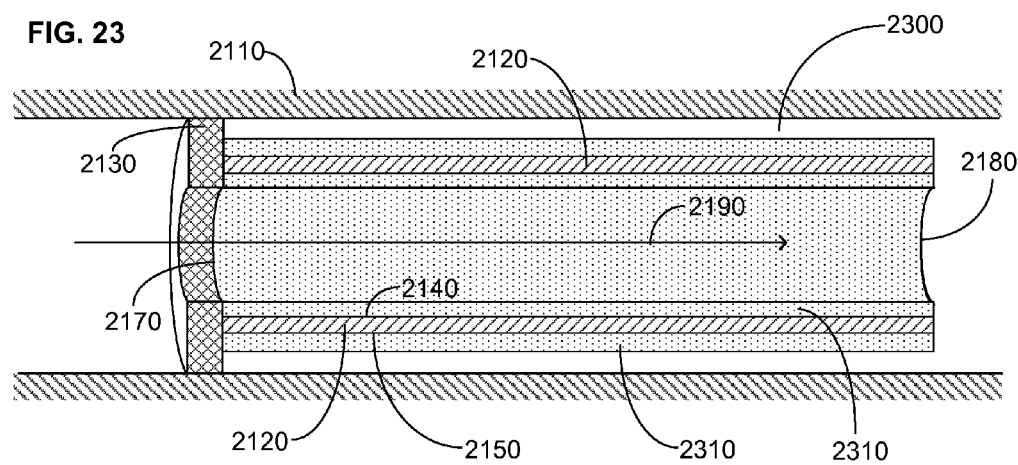

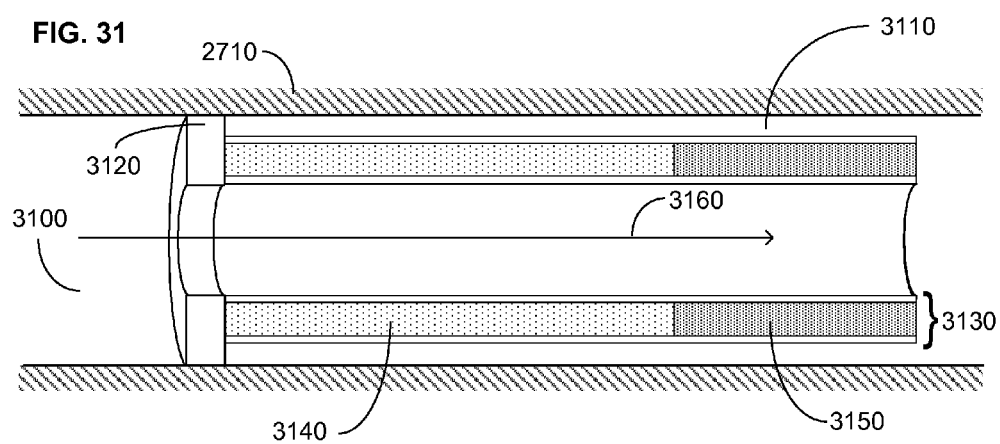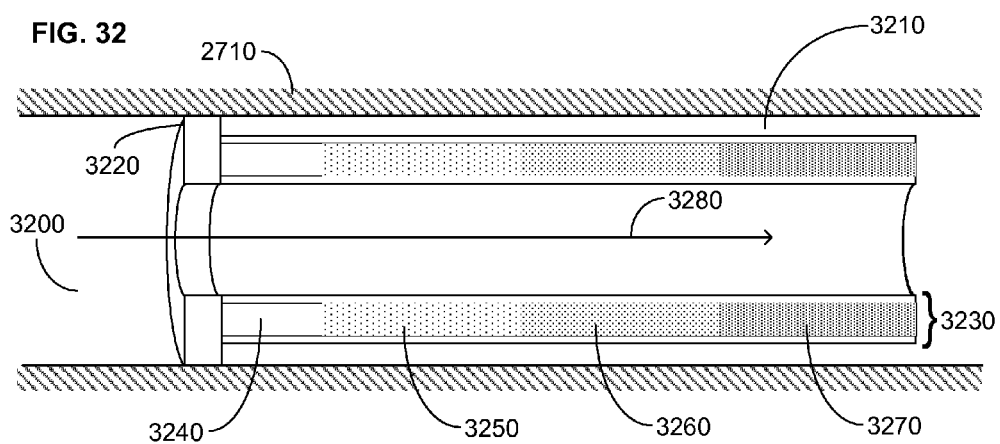

FIG. 34

3400
Obtaining a gastrointestinal device, the gastrointestinal device including a flexible tubular structure including an inner surface and an outer surface; and a proximal end and a distal end, the proximal end and the distal end forming a flow conduit through the flexible tubular structure; and at least one anchor structure including one or more gastric wall-engaging components configured to engage a wall of the gastrointestinal tract of a subject

3410
Distributing on at least a portion of at least one of the inner surface and the outer surface of the flexible tubular structure a plurality of at least one type of commensal microbe

FIG. 35

| 3400 Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject |
|---|
| 3500 wherein obtaining the gastrointestinal device includes manufacturing the gastrointestinal device |

| 3410 Distributing on at least a portion of at least one of the inner surface and the outer surface of the flexible tubular structure a plurality of at least one type of commensal microbe |
|---|
| 3510 wherein the flexible tubular structure is formed from a semi-permeable material |
| 3520 wherein the flexible tubular structure is formed from a substantially impermeable material |
| 3530 wherein the flexible tubular structure is noncontiguous |
| 3540 Coating the at least a portion of the at least one of the inner surface and the outer surface of the flexible tubular structure with the plurality of the at least one type of commensal microbe |
| 3550 Distributing on the at least a portion of the at least one of the inner surface and the outer surface of the flexible tubular structure the plurality of the at least one type of commensal microbe in a coating material |
| 3560 wherein the coating material includes at least one of a degradable coating material, a matrix coating material, a fibrous coating material, a hydrogel coating material, or a mucus coating material |
| 3570 Distributing on the at least a portion of the at least one of the inner surface and the outer surface of the flexible tubular structure the plurality of the at least one type of commensal microbe in a stimulus-responsive coating material |
| 3580 wherein the stimulus-responsive coating material includes at least one of a time-responsive coating material, a moisture-responsive coating material, a temperature-responsive coating material, a pH-responsive coating material, or a chemical-responsive coating material |

| 3590 Coating at least a portion of at least one of the inner surface and the outer surface of the flexible tubular structure with a coating material |
|---|

FIG. 36

3400
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject

3410
Distributing on at least a portion of at least one of the inner surface and the outer surface of the flexible tubular structure a plurality of at least one type of commensal microbe > 3600 Binding on the at least a portion of the at least one of the inner surface and the outer surface of the flexible tubular structure the plurality of the at least one type of commensal microbe > 3610 Binding on the at least a portion of the at least one of the inner surface and the outer surface of the flexible tubular structure the plurality of the at least one type of commensal microbe with at least one selective binding agent or non-selective binding agent
>
>> 3620 wherein the at least one selective binding agent includes an antibody, a protein, a peptide, a DNA fragment, an RNA fragment, a lectin, or an aptamer
>
>> 3630 wherein the at least one non-selective binding agent includes at least one of an adhesive, an absorbent, an adsorbent, a gel, or a matrix > 3640 Impregnating the at least a portion of at least one of the inner surface and the outer surface of the flexible tubular structure with the plurality of the at least one type of commensal microbe > 3650 Embedding into the at least a portion of the at least one of the inner surface and the outer surface of the flexible tubular structure the plurality of the at least one type of commensal microbe > 3660 Adsorbing, absorbing, covalently binding, or non-covalently binding to the at least a portion of the at least one of the inner surface and the outer surface of the flexible tubular structure the plurality of the at least one type of commensal microbe > 3670 Embedding the plurality of the at least one type of commensal microbe into the flexible tubular structure at the time of manufacture

3400
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject

---

3410
Distributing on at least a portion of at least one of the inner surface and the outer surface of the flexible tubular structure a plurality of at least one type of commensal microbe > 3700 wherein the plurality of the at least one type of commensal microbe includes at least one type of gut microbe > 3710 wherein the plurality of the at least one type of commensal microbe includes at least one type of genetically modified microbe > 3720 wherein the plurality of the at least one type of commensal microbe includes at least one type of commensal microbe from a fecal sample > 3730 wherein the plurality of the at least one type of commensal microbe includes at least part of a gut microbiota
>
>> 3740 wherein the at least part of the gut microbiota includes at least part of a gut microbiota of the subject
>
>> 3750 wherein the at least part of the gut microbiota includes at least part of a gut microbiota of one or more other individuals
>
>> 3760 wherein the at least part of the gut microbiota includes at least part of a healthy gut microbiota, a preferred gut microbiota, or a theoretical gut microbiota
>
>> 3770 preparing the at least part of the gut microbiota from a fecal sample
>
>> 3780 preparing the at least part of the gut microbiota from in vitro culture of one or more types of gut microbes

FIG. 38

3400
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject

3410
Distributing on at least a portion of at least one of the inner surface and the outer surface of the flexible tubular structure a plurality of at least one type of commensal microbe > 3800 wherein the plurality of the at least one type of commensal microbe includes a phylogenetically diverse mini-microbiota > 3810 wherein the plurality of at least one type of commensal microbe includes a plurality of at least one type of probiotic > 3820 wherein the at least one type of commensal microbe is beneficial to the subject >> 3830 wherein the at least one type of commensal microbe is beneficial to at least one of the immune system of the subject, a dietary condition of the subject, or a medical condition of the subject

3840
Distributing on at least a portion of at least one of the inner surface and the outer surface of the flexible tubular structure at least one of a prebiotic agent, a therapeutic agent, or a bioactive agent

FIG. 39

3900
Obtaining a gastrointestinal device, the gastrointestinal device including a flexible tubular structure including an inner surface and an outer surface; and a proximal end and a distal end, the proximal end and the distal end forming a flow conduit through the flexible tubular structure; and at least one anchor structure including one or more gastric wall-engaging components configured to engage a wall of the gastrointestinal tract of a subject

3910
Distributing on at least one of the inner surface and the outer surface of the flexible tubular structure at least one microbe-promoting agent, the at least one microbe-promoting agent configured to promote at least one of attraction, colonization, and growth of at least one type of commensal microbe

FIG. 40

3900
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject > 4000 wherein obtaining the gastrointestinal device includes manufacturing the gastrointestinal device

3910
Distributing on at least one of the inner surface and the outer surface of the flexible tubular structure at least one microbe-promoting agent, the at least one microbe-promoting agent configured to promote at least one of attraction, colonization, and growth of at least one type of commensal microbe > 4010 wherein the flexible tubular structure is formed from a semi-permeable material > 4020 wherein the flexible tubular structure is formed from a substantially impermeable material > 4030 wherein the flexible tubular structure is noncontiguous > 4040 Coating the at least one of the inner surface and the outer surface of the flexible tubular structure with the at least one microbe-promoting agent > 4050 Coating the at least one of the inner surface and the outer surface of the flexible tubular structure with the at least one microbe-promoting agent in a coating material
>> 4060 wherein the coating material includes at least one of a degradable coating material, a matrix coating material, a fibrous coating material, a hydrogel coating material, or a mucus coating material > 4070 Distributing on the at least one of the inner surface and the outer surface of the flexible tubular structure the at least one microbe-promoting agent in a stimulus-responsive coating material
>> 4080 wherein the stimulus-responsive coating material includes at least one of a time-responsive coating material, a moisture-responsive coating material, a temperature-responsive coating material, a pH-responsive coating material, or a chemical-responsive coating material

FIG. 41

3900
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject

3910
Distributing on at least one of the inner surface and the outer surface of the flexible tubular structure at least one microbe-promoting agent, the at least one microbe-promoting agent configured to promote at least one of attraction, colonization, and growth of at least one type of commensal microbe > 4100  Binding on the at least one of the inner surface and the outer surface of the flexible tubular structure the at least one microbe-promoting agent > 4110  Binding on the at least one of the inner surface and the outer surface of the flexible tubular structure the at least one microbe-promoting agent with at least one non-selective binding agent or selective binding agent >> 4120  wherein the at least one selective binding agent includes an antibody, a protein, a peptide, a DNA fragment, an RNA fragment, a lectin, or an aptamer >> 4130  wherein the at least one non-selective binding agent includes at least one of an adhesive, an absorbent, an adsorbent, a gel, or a matrix > 4140  Impregnating the at least one of the inner surface and the outer surface of the flexible tubular structure with the at least one microbe-promoting agent > 4150  Embedding into the at least one of the inner surface and the outer surface of the flexible tubular structure the at least one microbe-promoting agent > 4160  Adsorbing, absorbing, covalently binding, or non-covalently binding onto the at least one of the inner surface and the outer surface of the flexible tubular structure the at least one microbe-promoting agent

4170  Embedding the at least one microbe-promoting agent into the flexible tubular structure at the time of manufacture

FIG. 42

3900
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject

3910
Distributing on at least one of the inner surface and the outer surface of the flexible tubular structure at least one microbe-promoting agent, the at least one microbe-promoting agent configured to promote at least one of attraction, colonization, and growth of at least one type of commensal microbe > 4200 wherein the at least one microbe-promoting agent is configured to promote at least one of attraction, colonization, and growth of at least one type of commensal gut microbe > 4210 wherein the at least one microbe-promoting agent is configured to promote at least one of attraction, colonization, and growth of at least part of a gut microbiota > 4220 wherein the at least one microbe-promoting agent is configured to promote at least one of attraction, colonization, and growth of at least one type of endogenous commensal microbe > 4230 wherein the at least one microbe-promoting agent is configured to promote at least one of attraction, colonization, and growth of at least one type of administered commensal microbe > 4240 wherein the at least one microbe-promoting agent is configured to promote at least one of attraction, colonization, and growth of at least one type of commensal microbe derived from a fecal sample > 4250 wherein the at least one microbe-promoting agent is configured to promote at least one of attraction, colonization, and growth of at least one type of genetically engineered microbe > 4260 wherein the at least one microbe-promoting agent is configured to promote at least one of attraction, colonization, and growth of at least one type of commensal microbe derived from in vitro culture > 4270 wherein the at least one microbe-promoting agent is configured to promote at least one of attraction, colonization, and growth of at least one type of probiotic > 4280 wherein the at least one microbe-promoting agent is configured to promote at least one of attraction, colonization, and growth of a phylogenetically diverse mini-microbiota

FIG. 43

3900
Obtaining a gastrointestinal device, the gastrointestinal device including a flexible tubular structure including an inner surface and an outer surface, and a proximal end and a distal end, the proximal end and the distal end forming a flow conduit through the flexible tubular structure; and at least one anchor structure including one or more gastric wall-engaging components configured to engage a wall of the gastrointestinal tract of a subject

3910
Distributing on at least one of the inner surface and the outer surface of the flexible tubular structure at least one microbe-promoting agent, the at least one microbe-promoting agent configured to promote at least one of attraction, colonization, and growth of at least one type of commensal microbe 4300 wherein the at least one microbe-promoting agent is configured to promote at least one of attraction, colonization, and growth of at least one type of commensal microbe beneficial to the subject 4310 wherein the at least one microbe-promoting agent is configured to promote at least one of attraction, colonization, and growth of at least one type of commensal microbe beneficial to at least one of the immune system of the subject, a dietary condition of the subject, or a medical condition of the subject 4320 wherein the at least one microbe-promoting agent is configured to promote formation of a microbiome 4330 wherein the at least one microbe-promoting agent includes at least one prebiotic agent 4340 wherein the at least one microbe-promoting agent includes a mucus 4350 wherein the at least one microbe-promoting agent includes a binding agent 4360 wherein the at least one microbe-promoting agent includes at least one lectin 4370 Distributing on at least one first portion of the flexible tubular structure at least one first microbe-promoting agent and distributing on at least one second portion of the flexible tubular structure at least one second microbe-promoting agent 4380 Distributing on at least one of the inner surface and the outer surface of the flexible tubular structure at least one therapeutic agent 4390 Distributing on at least one of the inner surface and the outer surface of the flexible tubular structure at least one bioactive agent

FIG. 44

4400
Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place

4410
Distributing on one surface of the first material a plurality of at least one type of commensal microbe

4420
Applying a second material over the plurality of the at least one type of commensal microbe to form a layered wall, the layered wall allowing an interaction between the plurality of the at least one type of commensal microbe and an ingested product within the flexible tubular structure

FIG. 45

| |
|---|
| 4400 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and an anchor structure including one or more wall-engaging components configured to engage a wall of the gastrointestinal tract of a subject and hold the flexible tubular structure in place |
| 4500 Manufacturing the gastrointestinal device |

| |
|---|
| 4410 Distributing on one surface of the first material a plurality of at least one type of commensal microbe |
| 4510 wherein at least one of the first material and the second material includes a semi-permeable material |
| 4520 wherein the first material includes a first semi-permeable material and the second material includes a second semi-permeable material |
| 4530 wherein the first semi-permeable material differs from the second semi-permeable material |
| 4540 Distributing on an inner surface of the first material the plurality of the at least one type of commensal microbe, the inner surface facing the flow conduit through the flexible tubular structure |
| 4550 Distributing on an outer surface of the first material the plurality of the at least one type of commensal microbe, the outer surface facing the wall of the gastrointestinal tract |
| 4560 Coating the one surface of the first material with the plurality of the at least one type of commensal microbe |
| 4570 Distributing on the one surface of the first material the plurality of the at least one type of commensal microbe in a coating material |
| 4580 wherein the coating material includes at least one of a degradable coating material, a matrix coating material, a fibrous coating material, a porous coating material, a gel coating material, or a mucus coating material |
| 4590 Distributing on the one surface of the first material the plurality of the at least one type of commensal microbe in a stimulus-responsive coating material |
| 4595 wherein the stimulus-responsive coating material includes at least one of a time-responsive coating material, a moisture-responsive coating material, a temperature-responsive coating material, a pH-responsive coating material, or a chemical-responsive coating material |

| |
|---|
| 4420 Applying a second material over the plurality of the at least one type of commensal microbe to form a layered wall, the layered wall allowing an interaction between the plurality of the at least one type of commensal microbe and an ingested product within the flexible tubular structure |

FIG. 46

4400 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and an anchor structure including one or more wall-engaging components configured to engage a wall of the gastrointestinal tract of a subject and hold the flexible tubular structure in place 4410 Distributing on one surface of the first material a plurality of at least one type of commensal microbe 4600 Binding to the one surface of the first material the plurality of the at least one type of commensal microbe 4610 Binding to the one surface of the first material the plurality of the at least one type of commensal microbe with at least one non-selective binding agent or selective binding agent 4620 wherein the at least one selective binding agent includes at least one of an antibody, a protein, a peptide, a DNA fragment, an RNA fragment, a lectin, or an aptamer 4630 wherein the at least one non-selective binding agent includes at least one of an adhesive, an absorbent, adsorbent, a gel, or a matrix 4640 Impregnating into the one surface of the first material the plurality of the at least one type of commensal microbe 4650 Embedding into the one surface of the first material the plurality of the at least one type of commensal microbe 4660 Adsorbing, absorbing, covalently binding, or non-covalently binding onto the one surface of the first material the plurality of the at least one type of commensal microbe 4670 Embedding the plurality of the at least one type of commensal microbe into the flexible tubular structure at the time of manufacture 4420 Applying a second material over the plurality of the at least one type of commensal microbe to form a layered wall, the layered wall allowing an interaction between the plurality of the at least one type of commensal microbe and an ingested product within the flexible tubular structure

FIG. 47

4400 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and an anchor structure including one or more wall-engaging components configured to engage a wall of the gastrointestinal tract of a subject and hold the flexible tubular structure in place 4410 Distributing on one surface of the first material a plurality of at least one type of commensal microbe > 4700 wherein the plurality of the at least one type of commensal microbe includes at least one type of gut microbe > 4710 wherein the plurality of the at least one type of commensal microbe includes at least one type of genetically modified microbe > 4720 wherein the plurality of the at least one type of commensal microbe is derived from a fecal sample > 4730 wherein the plurality of at least one type of commensal microbe includes at least part of a gut microbiota >> 4740 wherein the at least part of the gut microbiota includes at least part of a gut microbiota from at least one of the subject or one or more other individuals >> 4750 wherein the at least part of the gut microbiota includes at least part of a healthy gut microbiota, a preferred gut microbiota, or a theoretical gut microbiota >> 4760 preparing the at least part of the gut microbiota from a fecal sample >> 4770 preparing the at least part of the gut microbiota from in vitro culture of one or more types of gut microbes > 4780 wherein the plurality of the at least one type of commensal microbe includes a phylogenetically diverse mini-microbiota > 4790 wherein the plurality of the at least one type of commensal microbe includes a plurality of at least one type of probiotic 4420 Applying a second material over the plurality of the at least one type of commensal microbe to form a layered wall, the layered wall allowing an interaction between the plurality of the at least one type of commensal microbe and an ingested product within the flexible tubular structure

FIG. 48

4400 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and an anchor structure including one or more wall-engaging components configured to engage a wall of the gastrointestinal tract of a subject and hold the flexible tubular structure in place 4410 Distributing on one surface of the first material a plurality of at least one type of commensal microbe 4800 wherein the at least one type of commensal microbe is beneficial to the subject 4810 wherein the at least one type of commensal microbe is beneficial to at least one of the immune system of the subject, a dietary condition of the subject, or a medical condition of the subject 4820 Distributing on a surface of the first material at least one of a prebiotic agent, a therapeutic agent, or a bioactive agent 4420 Applying a second material over the plurality of the at least one type of commensal microbe to form a layered wall, the layered wall allowing an interaction between the plurality of the at least one type of commensal microbe and an ingested product within the flexible tubular structure 4830 Applying a second material substantially identical to the first material 4840 Applying a second semi-permeable material with a permeability property that differs from a permeability property of the first material 4850 wherein the permeability property includes at least one of a sized-based permeability property, a charge-based permeability property, a pH-based permeability property, or a hydrophobicity-based permeability property 4860 Distributing on at least one surface of the second material at least one of a prebiotic agent, a therapeutic agent, or a bioactive agent

FIG. 49

4900
Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place

4910
Distributing on one surface of the first material at least one microbe-promoting agent

4920
Applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject

FIG. 50

| 4900 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place |
|---|
| 5000 Manufacturing the gastrointestinal device |

| 4910 Distributing on one surface of the first material at least one microbe-promoting agent |
|---|
| 5010 wherein at least one of the first material and the second material includes a semi-permeable material |
| 5020 wherein the first material includes a first semi-permeable material and the second material includes a second semi-permeable material |
| 5030 wherein the first semi-permeable material differs from the second semi-permeable material |
| 5040 Distributing on an inner surface of the first material the at least one microbe-promoting agent, the inner surface facing the flow conduit through the flexible tubular structure |
| 5050 Distributing on an outer surface of the first material the at least one microbe-promoting agent, the outer surface facing the wall of the gastrointestinal tract |
| 5060 Coating the one surface of the first material with the at least one microbe-promoting agent |
| 5070 Distributing on the one surface of the first material the at least one microbe-promoting agent in a coating material |
| 5080 wherein the coating material includes at least one of a degradable coating material, a matrix coating material, a fibrous coating material, a porous coating material, a gel coating material, or a mucus coating material |
| 5090 Distributing on the one surface of the first material the at least one microbe-promoting agent in a stimulus-responsive coating material |
| 5095 wherein the stimulus-responsive coating material includes at least one of a time-responsive coating material, a moisture-responsive coating material, a temperature-responsive coating material, a pH-responsive coating material, or a chemical-responsive coating material |

| 4920 Applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject |
|---|

FIG. 51

4900 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place

4910 Distributing on one surface of the first material at least one microbe-promoting agent

5100 Binding to the one surface of the first material the at least one microbe-promoting agent

5110 Binding to the one surface of the first material the at least one microbe-promoting agent with at least one non-selective binding agent or selective binding agent

5120 wherein the at least one selective binding agent includes at least one of an antibody, a protein, a peptide, a DNA fragment, an RNA fragment, a lectin, or an aptamer

5130 wherein the at least one non-selective binding agent includes at least one of an adhesive, an absorbent, an adsorbent, a gel, or a matrix

5140 Impregnating into the one surface of the first material the at least one microbe-promoting agent

5150 Embedding into the one surface of the first material the at least one microbe-promoting agent

5160 Adsorbing, absorbing, covalently binding, or non-covalently binding onto the one surface of the first material the at least one microbe-promoting agent

4920 Applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject

FIG. 52

4900 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place 4910 Distributing on one surface of the first material at least one microbe-promoting agent > 5200 wherein the at least one microbe-promoting agent is configured to promote at least one of attraction, colonization, and growth of at least one type of commensal microbe > 5210 wherein the at least one microbe-promoting agent is configured to promote at least one of attraction, colonization, and growth of at least one type of commensal gut microbe > 5220 wherein the at least one microbe-promoting agent is configured to promote at least one of attraction, colonization, and growth of at least part of a gut microbiota > 5230 wherein the at least one microbe-promoting agent is configured to promote at least one of attraction, colonization, and growth of at least one type of endogenous commensal microbe > 5240 wherein the at least one microbe-promoting agent is configured to promote at least one of attraction, colonization, and growth of at least one type of administered commensal microbe > 5250 wherein the at least one microbe-promoting agent is configured to promote at least one of attraction, colonization, and growth of at least one type of commensal microbe derived from a fecal sample > 5260 wherein the at least one microbe-promoting agent is configured to promote at least one of attraction, colonization, and growth of at least one type of genetically engineered microbe > 5270 wherein the at least one microbe-promoting agent is configured to promote at least one of attraction, colonization, and growth of at least one type of commensal microbe derived from in vitro culture > 5280 wherein the at least one microbe-promoting agent is configured to promote at least one of attraction, colonization, and growth of at least one type of probiotic > 5290 wherein the at least one microbe-promoting agent is configured to promote at least one of attraction, colonization, and growth of a phylogenetically diverse mini-microbiota 4920 Applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject

FIG. 53

| 4900 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place |
|---|

| 4910 Distributing on one surface of the first material at least one microbe-promoting agent |
|---|

> 5300 wherein the at least one microbe-promoting agent is configured to promote at least one of attraction, colonization, and growth of at least one type of commensal microbe beneficial to the subject
>
>> 5310 wherein the at least one microbe-promoting agent is configured to promote at least one of attraction, colonization, and growth of at least one type of commensal microbe beneficial to at least one of the immune system of the subject, a dietary condition of the subject, or a medical condition of the subject > 5320 wherein the at least one microbe-promoting agent is configured to promote formation of a microbiome > 5330 wherein the at least one microbe-promoting agent includes at least one prebiotic agent > 5340 wherein the at least one microbe-promoting agent includes mucus > 5350 wherein the at least one microbe-promoting agent includes a binding agent > 5360 wherein the at least one microbe-promoting agent includes at least one lectin > 5370 wherein the at least one microbe-promoting agent includes at least one chemoattractant

| 4920 Applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject |
|---|

FIG. 54

| 4900 Obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place |

| 4910 Distributing on one surface of the first material at least one microbe-promoting agent |

| 5400 Distributing on a surface of the first material at least one therapeutic agent |

| 5410 Distributing on a surface of the first material at least one bioactive agent |

| 4920 Applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject |
| 5420 Applying a second material substantially identical to the first material |
| 5430 Applying a second semi-permeable material with a permeability property that differs from a permeability property of the first material |
| 5440 wherein the permeability property includes at least one of a sized-based permeability property, a charge-based permeability property, a pH-based permeability property, or a hydrophobicity-based permeability property |

| 5450 Distributing on at least one surface of the second material at least one of a therapeutic agent and a bioactive agent |

GASTROINTESTINAL DEVICE WITH ASSOCIATED COMMENSAL MICROBES

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

Priority Applications

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a gastrointestinal device includes, but is not limited to, a flexible tubular structure including an inner surface and an outer surface; a plurality of at least one type of commensal microbe associated with at least a portion of at least one of the inner surface and the outer surface; and a proximal end and a distal end, the proximal end and the distal end forming a flow conduit through the flexible tubular structure; and at least one anchor structure including one or more gastric wall-engaging components configured to engage a wall of the gastrointestinal tract of a subject. In addition to the foregoing, other aspects of a device are described in the claims, drawings, and text forming a part of the present disclosure.

In an aspect, a gastrointestinal device includes, but is not limited to a flexible tubular structure including a layered wall, the flexible tubular structure including a plurality of at least one type of commensal microbe encased in the layered wall, the layered wall configured to allow an interaction between the plurality of the at least one type of commensal microbe and an ingested product within the flexible tubular structure; and a proximal end and a distal end, the proximal end and the distal end forming a flow conduit through the flexible tubular structure; and at least one anchor structure including one or more gastric wall-engaging components configured to engage a wall of the gastrointestinal tract of a subject. In addition to the foregoing, other aspects of a device are described in the claims, drawings, and text forming a part of the present disclosure.

In an aspect, a gastrointestinal device includes, but is not limited to, a flexible tubular structure including an inner surface and an outer surface; at least one microbe-promoting agent associated with at least one of the inner surface and the outer surface, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more gastric wall-engaging components configured to engage a wall of the gastrointestinal tract of a subject. In addition to the foregoing, other aspects of a device are described in the claims, drawings, and text forming a part of the present disclosure.

In an aspect, a gastrointestinal device includes, but is not limited to, a flexible tubular structure including a layered wall, the flexible tubular structure including at least one microbe-promoting agent encased in the layered wall of the flexible tubular structure, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more gastric wall-engaging components configured to engage a wall of the gastrointestinal tract of a subject. In addition to the foregoing, other aspects of a device are described in the claims, drawings, and text forming a part of the present disclosure.

In an aspect, a lumen-resident device includes, but is not limited to, a flexible tubular structure including an inner surface and an outer surface; a plurality of at least one type of commensal microbe associated with at least one of the inner surface and the outer surface of the flexible tubular structure; and a proximal end and a distal end, the proximal end and the distal end forming a flow conduit through the flexible tubular structure; and at least one anchor structure including one or more lumen wall-engaging components configured to engage a wall of a lumen of a subject. In addition to the foregoing, other aspects of a device are described in the claims, drawings, and text forming a part of the present disclosure.

In an aspect, a lumen-resident device includes, but is not limited to, a flexible tubular structure including a layered wall, the flexible tubular structure including a plurality of at least one type of commensal microbe encased in the layered wall, the layered wall configured to allow an interaction between the plurality of the at least one type of commensal microbe and a lumen of a subject; and a proximal end and a distal end, the proximal end and the distal end forming a flow conduit through the flexible tubular structure; and at least one anchor structure including one or more lumen wall-engaging components configured to engage a wall of the lumen of the subject. In addition to the foregoing, other aspects of a device are described in the claims, drawings, and text forming a part of the present disclosure.

In an aspect, a lumen-resident device includes, but is not limited to, a flexible tubular structure including an inner surface and an outer surface; at least one microbe-promoting agent associated with at least one of the inner surface and the outer surface, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more lumen wall-engaging components configured to engage a wall of a lumen of a subject. In addition to the foregoing, other aspects of a device are described in the claims, drawings, and text forming a part of the present disclosure.

In an aspect, a lumen-resident device includes, but is not limited to, a flexible tubular structure including a layered wall, the flexible tubular structure including a layered wall, the flexible tubular structure including at least one microbe-promoting agent encased in the layered wall, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more lumen wall-engaging components configured to engage a wall of the lumen of a subject. In addition to the foregoing, other aspects of a device are described in the claims, drawings, and text forming a part of the present disclosure.

In an aspect, a method of manufacture includes, but is not limited to, obtaining a gastrointestinal device, the gastrointestinal device including a flexible tubular structure including an inner surface and an outer surface; and a proximal end and a distal end, the proximal end and the distal end forming a flow conduit through the flexible tubular structure; and at least one anchor structure including one or more gastric wall-engaging components configured to engage a wall of the gastrointestinal tract of a subject; and distributing on at least a portion of at least one of the inner surface and the outer surface of the flexible tubular structure a plurality of at least one type of commensal microbe. In addition to the foregoing, other aspects of a method are described in the claims, drawings, and text forming a part of the present disclosure.

In an aspect, a method of manufacture includes, but is not limited to, obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place; distributing on one surface of the first material a plurality of at least one type of commensal microbe; and applying a second material over the plurality of the at least one type of commensal microbe to form a layered wall, the layered wall allowing an interaction between the plurality of the at least one type of commensal microbe and an ingested product within the flexible tubular structure. In addition to the foregoing, other aspects of a method are described in the claims, drawings, and text forming a part of the present disclosure.

In an aspect, a method of manufacturing includes, but is not limited to, obtaining a gastrointestinal device, the gastrointestinal device including a flexible tubular structure including an inner surface and an outer surface; and a proximal end and a distal end, the proximal end and the distal end forming a flow conduit through the flexible tubular structure; and at least one anchor structure including one or more gastric wall-engaging components configured to engage a wall of the gastrointestinal tract of a subject; and distributing on at least one of the inner surface and the outer surface of the flexible tubular structure at least one microbe-promoting agent, the at least one microbe-promoting agent configured to promote at least one of attraction, colonization, and growth of at least one type of commensal microbe. In addition to the foregoing, other aspects of a method are described in the claims, drawings, and text forming a part of the present disclosure.

In an aspect, a method of manufacture includes, but is not limited to, obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place; distributing on one surface of the first material at least one microbe-promoting agent; and applying a second material over the at least one microbe-promoting agent to form a layered wall, the layered wall allowing an interaction between the at least one microbe-promoting agent and at least one of an ingested product within the flexible tubular structure and a component of the gastrointestinal tract of the subject. In addition to the foregoing, other aspects of a method are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2 is a schematic of a cross-section through a gastrointestinal device including a plurality of at least one type of commensal microbe on an inner surface.

FIG. 3 is a schematic of a cross-section through a gastrointestinal device including a plurality of at least one type of commensal microbe on an outer surface.

FIG. 4 is a schematic of a cross-section through a gastrointestinal device including a plurality of at least one type of commensal microbe on an inner surface and an outer surface.

FIG. 9 is a schematic of proximal and distal anchor structures on a gastrointestinal device.

FIG. 10 is a schematic of anchor structures along the length of a flexible tubular structure.

FIG. 11 is a schematic of a gastrointestinal device engaging the walls of the gastrointestinal tract of a subject.

FIG. 19 is a schematic of a cross-section through a gastrointestinal device including a layered wall encasing multiple types of commensal microbes.

FIG. 20 is a schematic of a cross-section through a gastrointestinal device including a layered wall encasing a gradient of a plurality of at least one type of commensal microbes.

FIG. 21 is a schematic of a cross-section through a gastrointestinal device including at least one microbe-promoting agent associated with an outer surface.

FIG. 22 is a schematic of a cross-section through a gastrointestinal device including at least one microbe-promoting agent associated with an inner surface.

FIG. 23 is a schematic of a cross-section through a gastrointestinal device including at least one microbe-promoting agent associated with an outer surface and an inner surface.

FIG. 31 is a schematic of a cross-section through a gastrointestinal device including a layered wall encasing multiple types of microbe-promoting agents.

FIG. 32 is a schematic of a cross-section through a gastrointestinal device including a layered wall encasing a gradient of at least one microbe-promoting agent.

FIG. 34 shows a flowchart of a method.

FIG. 35 illustrates further aspects of a method such as depicted in FIG. 34.

FIG. 36 depicts further aspects of a method such as shown in FIG. 34.

FIG. 37 shows further aspects of a method such as illustrated in FIG. 34.

FIG. 38 illustrates further aspects of a method such as depicted in FIG. 34.

FIG. 39 shows a flowchart of a method.

FIG. 40 illustrates further aspects of a method such as depicted in FIG. 39.

FIG. 41 depicts further aspects of a method such as shown in FIG. 39.

FIG. 42 shows further aspects of a method such as illustrated in FIG. 39.

FIG. 43 illustrates further aspects of a method such as depicted in FIG. 39.

FIG. 44 shows a flowchart of a method.

FIG. 45 illustrates further aspects of a method such as depicted in FIG. 44.

FIG. 46 depicts further aspects of a method such as shown in FIG. 44.

FIG. 47 shows further aspects of a method such as illustrated in FIG. 44.

FIG. 48 illustrates further aspects of a method such as depicted in FIG. 44.

FIG. 49 shows a flowchart of a method.

FIG. 50 illustrates further aspects of a method such as depicted in FIG. 49.

FIG. 51 depicts further aspects of a method such as shown in FIG. 49.

FIG. 52 shows further aspects of a method such as illustrated in FIG. 49.

FIG. 53 illustrates further aspects of a method such as depicted in FIG. 49.

FIG. 54 depicts further aspects of a method such as shown in FIG. 49.

DETAILED DESCRIPTION

Figure 1:
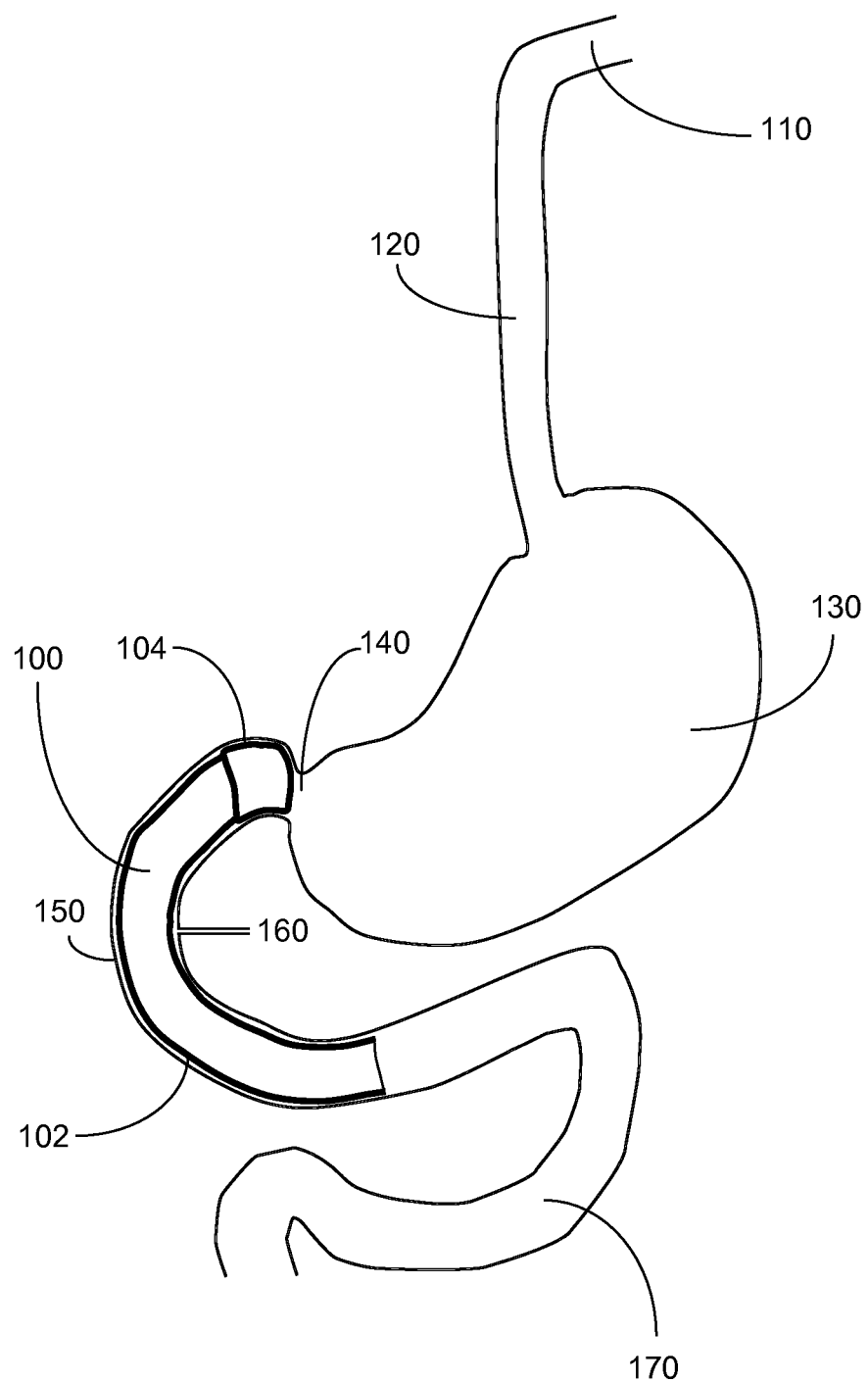
FIG. 1 is a schematic of a gastrointestinal device positioned in the gastrointestinal tract of a subject.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Described herein are devices and methods for establishing, maintaining, supporting, and/or altering the health of a mammalian digestive system, including its flora, to treat a medical condition (e.g., an inflammatory disease, metabolic disease, cancer, microbial infection, ischemia, stricture, obstruction, or trauma) and/or dietary need (e.g., nutritional need, weight control, and/or food sensitivity). Intraluminal devices are well known as means to treat disorders of the gastrointestinal tract and to promote dietary and weight control. These devices include gastrointestinal endoluminal sleeves, liners, and stents, which function, for example, to bypass a diseased or damaged portion of the gastrointestinal tract, to bypass a portion of the gastrointestinal tract (e.g., the small intestine) to reduce absorption (e.g., in weight loss), or to structurally support diseased or damaged portions of the gastrointestinal tract. Such devices, however, neglect the importance of commensal microbes that normally reside in the gastrointestinal tract and the roles they play in the coordinated function of the gastrointestinal tract. Disruption or bypass of the flow of food or chyme through the gut, and thus its normal exposure to commensal microbes, can result in complications including diarrhea and vitamin and micronutrient insufficiencies, as well as disruptions in normal flora in nearby tissues.

The mammalian gastrointestinal tract includes an array of endogenous microbes that make up the microbiota. The microbiota of gut flora includes bacteria, fungi, archaea, and viruses. For example, the human gut, defined here as any part of the alimentary canal or gastrointestinal tract, is home to approximately 100 trillion bacteria cells. Humans have co-evolved to exist with this microbial community largely in a mutualistic relationship where humans as host rely on these microorganisms for a number of key functions related to nutrition, energy balance, susceptibility to obesity, education of the immune system, and prevention of infection by pathogenic species. In turn, humans provide a source of nutrition to the microbial community in the form of mucus lining the inner surface of the gastrointestinal tract. Furthermore, the microbial lineages present in the gut appear to be at least partially dependent upon the types of foods ingested, the diet providing nutrients to both the host and microbial community. For example, abundant *Prevotella* correlate with consumption of carbohydrates, while abundant *Bacteroides* correlate with consumption of choline, fats, and amino acids. For example, a more diverse diet correlates with increased gut bacterial diversity. See, e.g., Hoffman et al. (2013) *PLoS ONE* 8(6):e66019, which is incorporated herein by reference. Thus, a healthy and intact microbiota is important to both digestive and general health, and disruptance of the microbiota has been associated with numerous disease processes including inflammatory bowel diseases, metabolic diseases (e.g., type 2 diabetes and obesity), cancer, and infection, particularly with *Clostridium difficile* infection. See, e.g., Wu & Lewis (2013) *Clin. Gastroenterol. Hepatol.* 11:774-777; Cox & Blaser (2013) *Cell Metab.* 17:883-894; Maynard et al. (2012) *Nature* 489:231-241, which are incorporated herein by reference.

With reference to FIG. 1, shown is a view of a portion of the gastrointestinal tract including a gastrointestinal device 100. During digestion, food enters the mouth 110, is chewed, and passes down the esophagus 120 to the stomach 130. The stomach 130 converts the ingested food into chyme, a thick semi-solid mass. The chyme passes through the pylorus 140 and into the duodenum 150 of the small intestine, past an inlet 160 from the bile duct and the pancreas, and onto the jejunum 170. In this non-limiting embodiment, gastrointestinal device 100 is positioned in the duodenum 150 distal to the pylorus 140. In some embodiments, gastrointestinal device 100 may be placed in a mouth, an esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof of a subject. Gastrointestinal device 100 includes a flexible tubular structure 102 and an anchor structure 104.

In an embodiment, flexible tubular structure 102 includes an inner surface and an outer surface, a plurality of at least one type of commensal microbe associated with at least a portion of at least one of the inner surface and the outer surface, and a proximal end and a distal end, the proximal end and the distal end forming a flow conduit through the flexible tubular structure.

In an embodiment, flexible tubular structure 102 is formed from a semi-permeable material and includes an inner surface and an outer surface, a plurality of at least one type of commensal microbe associated with at least a portion of the at least one of the inner surface and the outer surface, and a proximal end and a distal end, the proximal end and the distal end forming a flow conduit through the flexible tubular structure.

In an embodiment, flexible tubular structure 102 is formed from a substantially impermeable material and includes an inner surface and an outer surface, a plurality of at least one type of commensal microbe associated with at least a portion of the at least one of the inner surface and the outer surface, and a proximal end and a distal end, the proximal end and the distal end forming a flow conduit through the flexible tubular structure.

In an embodiment, flexible tubular structure 102 includes a layered wall, a plurality of at least one type of commensal microbe encased in the layered wall, the layered wall configured to allow an interaction between the plurality of the at least one type of commensal microbe and an ingested product within the flexible tubular structure, and a proximal end and a distal end, the proximal end and the distal end forming a flow conduit through the flexible tubular structure.

In an embodiment, flexible tubular structure 102 includes an inner surface and an outer surface, at least one microbe-promoting agent associated with at least one of the inner surface and the outer surface, the at least one microbe-promoting agent configured to promote at least one of attraction, colonization, and growth of at least one type of commensal microbe, and a proximal end and a distal end, the proximal end and the distal end forming a flow conduit through the flexible tubular structure.

In an embodiment, flexible tubular structure 102 includes a layered wall, a least one microbe-promoting agent encased in the layered wall, the at least one microbe-promoting agent configured to promote at least one of attraction, colonization, and growth of at least one type of commensal microbe, and a proximal end and a distal end, the proximal end and the distal end forming a flow conduit through the flexible tubular structure.

Gastrointestinal device 100 further includes at least one anchor structure 104. In this non-limiting embodiment, the anchor structure 104 is shown associated with the proximal end of flexible tubular structure 102. In some embodiments, the at least one anchor structure may be associated with the distal end of the flexible tubular structure. In some embodiments, the gastrointestinal device may include two or more anchor structures positioned at the proximal end, the distal end, and/or along the length of the flexible tubular structure. In some embodiments, the structure of the flexible tubular structure of the gastrointestinal device forms at least one anchor structure. Anchor structure 104 includes one or more gastric wall-engaging components configured to engage a wall of the gastrointestinal tract of the subject.

In an aspect, gastrointestinal device 100 including a plurality of at least one type of commensal microbe is beneficial to a medical condition of a subject.

FIGS. 2-4 illustrate further aspects of a gastrointestinal device. FIG. 2 shows a longitudinal cross-section through gastrointestinal device 200 positioned within the gastrointestinal tract 210. Gastrointestinal device 200 includes flexible tubular structure 220 (diagonal pattern) and anchor structure 230. Flexible tubular structure 220 includes inner surface 240 and outer surface 250. The flexible tubular structure 220 of gastrointestinal device 200 includes a plurality of at least one type of commensal microbe 260 (stippled pattern) associated with the outer surface 250. The flexible tubular structure 220 further includes proximal end 270 and distal end 280, the proximal end 270 and the distal end 280 forming a flow conduit 290 through the flexible tubular structure 220. Anchor structure 230 includes one or more gastric wall-engaging components configured to engage a wall of the gastrointestinal tract 210 of the subject. In an aspect, gastrointestinal device 200 is configured to allow the plurality of the at least one type of commensal microbe 260 associated with the outer surface 250 of the flexible tubular structure 220 to come in contact with gastrointestinal tract 210. In an aspect, the gastrointestinal device is configured to allow components (e.g., vitamins) secreted by the at least one type of commensal microbe to interact with and/or be absorbed by the gastrointestinal tract.

FIG. 3 shows a longitudinal cross-section through gastrointestinal device 300 positioned within the gastrointestinal tract 210. Gastrointestinal device 300 includes flexible tubular structure 220 (diagonal pattern) and anchor structure 230. Flexible tubular structure 220 includes inner surface 240 and outer surface 250. The flexible tubular structure 220 of gastrointestinal device 300 includes a plurality of at least one type of commensal microbe 310 (stippled pattern) associated with the inner surface 240. The flexible tubular structure 220 further includes proximal end 270 and distal end 280, the proximal end 270 and the distal end 280 forming a flow conduit 290 through the flexible tubular structure 220. Anchor structure 230 includes one or more gastric wall-engaging components configured to engage a wall of the gastrointestinal tract 210 of the subject. In an aspect, gastrointestinal device 300 is configured to allow components of the food or chyme flowing through the flexible tubular structure to come in contact with the plurality of the at least one type of commensal microbe 310 associated with the inner surface 240 of flexible tubular structure 220. In an aspect, the gastrointestinal device is configured to allow components secreted by the at least one type of commensal microbe to interact with an ingested product, e.g., one or more components of the food or chyme.

FIG. 4 shows a longitudinal cross-section through gastrointestinal device 400 positioned within the gastrointestinal tract 210. Gastrointestinal device 400 includes flexible tubular structure 220 (diagonal pattern) and anchor structure 230. Flexible tubular structure 220 includes inner surface 240 and outer surface 250. The flexible tubular structure 220 of gastrointestinal device 400 includes a plurality of at least one type of commensal microbe 410 (stippled pattern) associated with the inner surface 240 and the outer surface 250. The flexible tubular structure 220 further includes proximal end 270 and distal end 280, the proximal end 270 and the distal end 280 forming a flow conduit 290 through the flexible tubular structure 220. Anchor structure 230 includes one or more gastric wall-engaging components configured to engage a wall of the gastrointestinal tract 210 of the subject. In an aspect, gastrointestinal device 400 is configured to allow the plurality of at least one type of commensal microbe on the inner surface to interact with components of the food or chyme as it passes through the flexible tubular structure and to allow the plurality of at least one type of commensal microbe on the outer surface to interact with the gastrointestinal tract 210 of the subject.

Flexible Tubular Structure

A gastrointestinal device described herein includes a flexible tubular structure. In an aspect, the flexible tubular structure is sized for placement in a portion of the gastrointestinal tract of the subject. In an aspect, the flexible tubular structure is sized for placement in a mouth, an esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof of the subject. In an aspect, the flexible tubular structure is sized for placement in a portion of the gastrointestinal tract and includes a flow conduit from the proximal end to the distal end in fluid communication with at least a portion of the gastrointestinal tract. For example, the flexible tubular structure is appropriately sized for allowing passage of ingested food and/or chyme through the internal portion of the flexible tubular structure without becoming obstructed.

In an aspect, the flexible tubular structure is a sleeve, a liner, or a stent. In an aspect, the flexible tubular structure is of a type configured to treat a medical condition of the subject. In an aspect, the flexible tubular structure is of a type configured to treat at least one of diabetes, obesity, metabolic syndrome, colitis, cancer, inflammatory bowel disease, irritable bowel syndrome, an autoimmune disorder, trauma, stricture, or a microbial infection.

In an aspect, the flexible tubular structure of the gastrointestinal device is sufficiently flexible to allow peristaltic motions of the gastrointestinal tract to move ingested food and/or chyme through the flexible tubular structure. For example, the flexible tubular structure can be sufficiently flexible to allow for movement of ingested food and/or chyme through the flexible tubular structure in response to contractile waves moving along the gastrointestinal tract. For example, the flexible tubular structure can be sufficiently flexible to allow for movement of ingested food through the flexible tubular structure in response to primary and secondary peristaltic waves in the esophagus. For example, the flexible tubular structure can be sufficiently flexible to allow for movement of chyme through the flexible tubular structure in response to short pulsed waves of contraction in the small intestine. For example, the flexible tubular structure can be sufficiently flexible to allow for movement of feces through the flexible tubular structure in response to periodic mass movements in the large intestine and colon.

In an aspect, the flexible tubular structure of the gastrointestinal device is sufficiently flexible to be moved through the bends of the gastrointestinal tract without damaging, e.g., perforating, the gastrointestinal wall. For example, the flexible tubular structure is flexible enough to be placed deep within the gastrointestinal tract using a catheter, endoscope, or enteroscope-like device. For example, the flexible tubular structure is flexible enough to be moved through the gastrointestinal tract attached to a device designed to travel through the lumen of the gastrointestinal tract. See, e.g., U.S. Pat. No. 7,998,060 to Ferren et al. titled "Lumen-traveling delivery device," which is incorporated herein by reference. For example, the flexible tubular structure is flexible enough to be moved through the gastrointestinal tract using an endoscope.

In an aspect, the flexible tubular structure of the gastrointestinal device includes a flexible material, e.g., a material that provides flexibility. In an aspect, the flexible tubular structure of the gastrointestinal device includes a flexible form or structure, e.g., that provides flexibility. In an aspect, the flexible tubular structure of the gastrointestinal device includes at least one rigid material. For example, the flexibility of a tubular structure that is a stent may owe its flexibility to a flexible helix design of multiple rigid struts.

In an aspect, the flexible tubular structure has a diameter consistent with the inner diameter of a given portion of the gastrointestinal tract. In an aspect, the flexible tubular structure is a flexible circular tube structure with a circular cross-sectional shape. However, the flexible tubular structure can include tube structures having cross-sectional shapes with two or more sides. In an aspect, the cross-sectional shape of the flexible tubular structure is a multi-sided polygon. For example, the cross-sectional shape of the flexible tubular structure can include 2 sides, 3 sides, 4 sides, 5 sides, 6 sides, 7 sides, 8 sides, 9 sides, 10 sides, or more. For example, the cross-sectional shape of the flexible tubular structure can include a triangle, a square, a pentagon, a hexagon, a heptagon, an octagon, a nonagon, a decagon, or other appropriately sized, multi-sided polygon.

In an aspect, the flexible tubular structure is sized in diameter so as to not be in sealing contact with the gastrointestinal wall to allow unrestricted flow of gastric, biliary, pancreatic, and intestinal secretions between the gastrointestinal wall and the outer surface of the flexible tubular structure. In an aspect, the flexible tubular structure has a diameter of between about 5 mm and about 40 mm. For example, the flexible tubular structure can have a diameter of about 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, or 40 mm.

In an aspect, the flexible tubular structure has a length sufficient to cover a desired length of the gastrointestinal tract. For example, the flexible tubular structure can extend in length from a location in the esophagus to a location in the stomach or beyond. For example, the flexible tubular structure can extend in length from a location proximal to the pyloric junction to the jejunum at the ligament of Treitz. For example, the flexible tubular structure can extend in length from the junction between the small intestine and the large intestine to the rectum or about 1.5 meters. For example, the flexible tubular structure can extend the entire length of the small intestine or about 7 meters. In an aspect, the flexible tubular structure has a length of between about 0.001 meters to about 9 meters. For example, the flexible tubular structure can have a length of about 0.001 meters, 0.002 meters, 0.003 meters, 0.005 meters, 0.005 meters, 0.006 meters, 0.007 meters, 0.008 meters, 0.009 meters, 0.01 meters, 0.015 meters, 0.02 meters, 0.05 meters, 0.1 meters, 0.15 meters, 0.2 meters, 0.25 meters, 0.30 meters, 0.35 meters, 0.4 meters, 0.45 meters, 0.5 meters, 0.55 meters, 0.6 meters, 0.65 meters, 0.7 meters, 0.75 meters, 0.8 meters, 0.85 meters, 0.90 meters, 0.95 meters, 1.0 meters, 1.1 meters, 1.15 meters, 1.2 meters, 1.25 meters, 1.30 meters, 1.35 meters, 1.4 meters, 1.45 meters, 1.5 meters, 1.55 meters, 1.6 meters, 1.65 meters, 1.7 meters, 1.75 meters, 1.8 meters, 1.85 meters, 1.90 meters, 1.95 meters, 2 meters, 2.5 meters, 3 meters, 3.5 meters, 4 meters, 4.5 meters, 5 meters, 5.5 meters, 6 meters, 6.5 meters, 7 meters, 7.5 meters, 8 meters, 8.5 meters, or 9 meters.

In an aspect, the flexible tubular structure has a thickness, e.g., the distance between the inner surface and the outer surface of the flexible tubular structure, which is dependent upon the material used to form the flexible tubular structure. In an aspect, the flexible tubular structure has a thickness of between about 0.002 mm and about 3 mm. For example, the thickness of the flexible tubular structure can be about 0.002 mm, 0.005 mm, 0.0075 mm, 0.01 mm, 0.02 mm, 0.03 mm, 0.04 mm, 0.05 mm, 0.06 mm, 0.07 mm, 0.08 mm, 0.1 mm, 0.2 mm, 0.3 mm, 0.4 mm, 0.5 mm, 0.6 mm, 0.7 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2 mm, 2.1 mm, 2.2 mm, 2.3 mm, 2.4 mm, 2.5 mm, 2.6 mm, 2.7 mm, 2.8 mm, 2.9 mm, or 3 mm in thickness.

In an aspect, the flexible tubular structure includes a sleeve or liner. For example, the flexible tubular structure can include a long sleeve or liner formed from a thin-walled polymer material such as silicone, polyurethane, nylon, polytetrafluoroethylene, fluorinated ethylene propylene, polyethylene, or other suitable material. See, e.g., U.S. Patent Application No. 2012/0184893 to Thompson et al. titled "Anchors and methods for intestinal bypass sleeves," which is incorporated herein by reference. In an aspect, the sleeve is reinforced with rings or a spiral made of wire and/or plastic to hold the sleeve open. See, e.g., U.S. Pat. No. 7,037,344 to Kagan et al. titled "Apparatus and Methods for Treatment of Morbid Obesity," which is incorporated herein by reference.

In an aspect, the flexible tubular structure includes a stent. In an aspect, the flexible tubular structure includes a metal stent. For example, the flexible tubular structure can include a self-expandable metallic stent. See, e.g., U.S. Pat. No. 8,753,407 to Nguyen titled "Temporary protective gastrointestinal device," which is incorporated herein by reference. In an aspect, the flexible tubular structure includes a plastic stent. For example, the flexible tubular structure can include a self-expandable plastic stent. See, e.g., van Boeckel et al. (2012) *BMC Gastroenterology* 12:19, which is incorporated herein by reference. In an aspect, the flexible tubular structure includes a stent configured to expand in the gastrointestinal tract. See, e.g., U.S. Pat. No. 5,662,713 to Andersen & Strecker titled "Medical stents for body lumens exhibiting peristaltic motion," which is incorporated herein by reference. In an aspect, the flexible tubular structure is between about 1 cm and about 50 cm. For example, the flexible tubular structure can include a stent that is about 1 cm, 2 cm, 3 cm, 4 cm, 5 cm, 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 25 cm, 30 cm, 35 cm, 40 cm, 45 cm, or 50 cm in length. In an aspect, at least a portion of the stent is not flexible.

In an aspect, the flexible tubular structure is formed from a material that helps to minimize or prevent tissue in-growth. In an aspect, the flexible tubular structure is formed from a material that helps to promote tissue in-growth. In an aspect, the flexible tubular structure is formed from a material that is non-irritating to the gastrointestinal tract, so as to aid in removal once removal is desired. In an aspect, the flexible tubular structure is formed from a material that allows the gastrointestinal tract to function without complications such as allergic reactions or other adverse side effects. For example, the flexible tubular structure is preferably formed from a material that does not cause extended chronic inflammation, does not cause cell disruption or thrombosis, and is not cytotoxic. In an aspect, the flexible tubular structure is formed from a material that is suitable for exposure to the gastrointestinal tract and gastrointestinal tract fluids. For example, the flexible tubular structure is formed from a material that is compatible with the pH conditions of the gastrointestinal tract. In an aspect, the flexible tubular structure is formed from a material that is biodegradable.

In an aspect, the flexible tubular structure is formed from a biocompatible material. For example, the flexible tubular structure can be formed from a biocompatible material that includes at least one of a metallic compound, a polymer, a plastic, a ceramic, or a composite. For example, the flexible tubular structure can be formed from at least one of a natural polymer, a modified natural polymer, and/or a synthetic polymer. For example, the flexible tubular structure can be formed from a synthetic biocompatible polymer, e.g., poly (vinyl alcohol), poly(ethylene glycol), or poly(N-2-hydroxypropyl methacrylamide). Non-limiting examples of biocompatible materials include ultra-high-molar-mass polyethylene (UHMWPE), poly(caprolactone), poly(lactic acid) (PLLA), polytetrafluoroethylene (PTFE), polyvinylchloride, polyethersulfone, polyetheretherketone (PEEK), polysulfone, polypropylene, poly(methyl methacrylate) (PMMA), and other acrylics and methacrylics, silicones, and polyurethanes. See, e.g., Vert et al. (2012) *Pure Appl. Chem.* 84:377-410, which is incorporated herein by reference.

In an aspect, the flexible tubular structure is formed from a responsive biocompatible material. For example, the flexible tubular structure can be formed from a material that changes properties in response to a stimulus, e.g., changes in pH. temperature, or presence of a substance. For example, the flexible tubular structure can be formed from poly(N-isopropylacrylamide) (PIPAAm) which changes form in response to changes in temperature.

In an aspect, at least a portion of the flexible tubular structure includes a degradable material. For example, all or part of the flexible tubular structure can be formed from a material that degrades over time and is passed through the gastrointestinal tract. In an aspect, at least a portion of the flexible tubular structure includes a stimulus-responsive degradable material. In an aspect, the stimulus-responsive degradable material includes at least one of a time-responsive degradable material, a moisture-responsive degradable material, a temperature-responsive degradable material, a pH-responsive degradable material, or a chemical-responsive degradable material. In an aspect, all or part of the flexible tubular structure is formed from a polymer that includes hydrolytically unstable linkages in the backbone of the polymer. For example, all or part of the flexible tubular structure can be formed from a polymer that includes one or more hydrolytically unstable linkages that include a chemical functional group such as, for example, an ester, anhydride, orthoester, or amide. In an aspect, all or part of the flexible tubular structure is formed from a polymer that is degraded by microorganisms. In an aspect, only a portion of the flexible tubular structure is formed from a degradable material. For example, the flexible tubular structure may have easily passable segments that are connected through degradable portions such that degradation of the degradable portions results in breaking the flexible tubular structure down into easily passable segments. Non-limiting examples of degradable materials include polyhydroxylalkanoates (e.g., poly-3-hydroxybutyrate, polyhydroxyvalerate, and polyhydroxyhexanoate), polylactic acid, polyglycolide, polybutylene succinate, polycaprolactone, polyanhydrides, polyvinyl alcohol, or cellulose esters. For example, at least part of the flexible tubular structure can be formed from a degradable material that is responsive to a low pH, e.g., the approximate pH of chyme or about pH 2.0. For example, the flexible tubular structure can include a biodegradable stent. See, e.g., U.S. Pat. No. 8,753,387 to Headley & Geltz titled "Bioabsorbable stents with reinforced filaments," which is incorporated herein by reference.

In an aspect, the flexible tubular structure is formed from a semi-permeable material. In an aspect, the semi-permeable material is selectively permeable. In an aspect, the semi-permeable material allows certain molecules to pass laterally through the flexible tubular structure while preventing other molecules from passing laterally through the flexible tubular structure. For example, the semi-permeable material can be configured to allow certain ingested molecules to pass laterally through the wall of the flexible tubular structure while preventing other ingested molecules from passing laterally through the flexible tubular structure. For example, the semi-permeable material may allow water and small solutes, e.g., vitamins, to pass laterally through the flexible tubular structure to the underlying wall of the gastrointestinal tract for absorption while preventing the passage of larger ingested components, e.g., fats or complex carbohydrates. For example, the semi-permeable material may allow digestive enzymes, e.g., bile or pancreatic enzymes, to pass through the flexible tubular structure from the gastrointestinal tract. For example, the semi-permeable material may allow vitamins and micronutrients to pass laterally through the flexible tubular structure to the underlying wall of the gastrointestinal tract for absorption.

In an aspect, the semi-permeable material includes any of an number of polymers, non-limiting examples of which include polymers, copolymers, and/or block polymers of poly(methyl methacrylate), poly(alkyl acrylate), poly(alkyl methacrylate), poly(acrylamide), poly(N-alkyl acrylamide), poly(N-isopropyl acrylamide), poly(N,N-dialkyl acrylamide), poly(methacrylamide), poly(N-alkyl methacrylamide), poly(N-isopropyl methacrylamide), poly(N,N-dialkyl methacrylamide), poly(ethylene oxide), poly(vinyl chloride), poly(vinyl fluoride), poly(aryl ether), poly(vinyl ether), poly (vinyl acetate), poly(vinyl butyral), poly(vinyl formal), poly (acrylonitrile), poly(methacrylonitrile), poly(siloxane), poly (styrene), poly(butylene), poly(isobutylene), poly(isoprene), poly(propylene), poly(methylpentene), poly(vinyl alcohol), or poly(ethylene glycol). See, e.g., U.S. Patent Application No. 2008/0060995 to Zhang et al. titled "Semi-Permeable Membrane," which is incorporated herein by reference.

In an aspect, the semi-permeable material is selectively permeable based on size. For example, the semi-permeable material can be selectively permeable to molecules based on size. For example, the semi-permeable material can include a form of dialysis membrane. For example, the semi-permeable material can include regenerated cellulose, cellulose esters, or cellulose acetate cross-linked in various ways to form films with differing properties and pores sizes. For example, the semi-permeable material can include polyethersulfone, etched polycarbonate, or collagen manufactured to form films with differing properties and pore sizes.

In an aspect, the semi-permeable material is selectively permeable based on hydrophobicity. For example, the semi-permeable material can be selectively permeable to molecules based on hydrophobicity. In an aspect, the semi-permeable material includes a hydrophilic membrane. In an aspect, the semi-permeable material includes a hydrophobic membrane. For example, a hydrophobic semi-permeable membrane can be formed from poly(methyl methacrylate) in ethyl acetate as describe in U.S. Patent Application No. 2008/0060995 to Zhang et al. titled "Semi-Permeable Membrane," which is incorporated herein by reference. In an aspect, the hydrophobicity of a semi-permeable material is altered using an oxygen plasma etching process. For example, the walls of pores near the surface of the semi-permeable material may be converted from substantially hydrophobic to substantially hydrophilic surfaces through the action of oxygen plasma to generate polar groups on the surface of the semi-permeable material. See, e.g., U.S. Pat. No. 5,275,766 to Gadkaree & Hersh titled "Method of Making Semi-Permeable Polymer Membranes," which is incorporated herein by reference.

In an aspect, the semi-permeable material is selectively permeable based on charge. For example, the semi-permeable material can be selectively permeable to molecules based on charge, e.g., positive, negative, or neutral charge. In an aspect, the semi-permeable material includes an ion-exchange membrane. For example, the semi-permeable material can include a semi-permeable membrane with discrete particles of ion exclusion material associated with a porous supporting material, the latter of which is freely permeable. See, e.g., U.S. Pat. No. 3,331,772 to Brownscombe & Kern titled "Desalting water by reverse osmosis through novel semipermeable membranes,' which is incorporated herein by reference.

In an aspect, the semi-permeable material includes an active, selectively permeable material. For example, the semi-permeable material may incorporate pumps, e.g., ion pumps or other active transport pumps, to move solutes from low concentration to high concentration.

In an aspect, the semi-permeable material includes a plurality of pores. In an aspect, each of the plurality of pores has a diameter of as small as 200 nm and as large as 3000 nm. In an aspect, one or more of the plurality of pores is less than 200 nm in diameter and can be even smaller than 20 nm. In an aspect, the plurality of pores includes at least two pores. In an aspect, the plurality of pores includes 2 pores to about 100 pores. For example, the plurality of pores can include 2 pores, 3 pores, 4 pores, 5 pores, 6 pores, 7 pores, 8 pores, 9 pores, 10 pores, 15 pores, 20 pores, 25 pores, 30 pores, 35 pores, 40 pores, 45 pores, 50 pores, 55 pores, 60 pores, 65 pores, 70 pores, 75 pores, 80 pores, 85 pores, 90 pores, 95 pores, or 100 pores. In an aspect, the plurality of pores includes about 100 pores to about 100,000 pores. In an aspect, the plurality of pores includes over 100,000 pores. In an aspect, the number of pores is dependent upon the manufacturing process. For example, a semi-permeable material formed from a porous material may include substantially more pores than a semi-permeable material into which one or more pores are machined.

In an aspect, the plurality of pores is formed during the course of manufacturing the semi-permeable material. For example, a porous semi-permeable material formed from cross-linking of cellulose and/or cellulose esters will by definition include a plurality of pores. For example, a stent-like flexible tubular structure includes pores defined by the matrix forming the stent, e.g., a helix design of multiple rigid struts. In an aspect, the semi-permeable material includes a fibrous material. For example, the fibrous material can include cellulose.

In an aspect, the plurality of pores is machined into a material to form the semi-permeable material. For example, the plurality of pores can be machined into a thin sheet of polymer, e.g., poly(propylene), to form the semi-permeable material. In an aspect, each of the plurality of pores is machined into the material with a drill to form the semi-permeable material. In an aspect, each of the plurality of pores is machined into the material using pins and/or needles. For example, the plurality of pores can be machined into the material using a rotary pinned perforation roller with either cold or hot pins. In an aspect, each of the plurality of pores is machined into the material with a laser to form the semi-permeable material. Non-limiting examples of lasers for laser cutting and/or boring include $CO_2$ lasers, neodymium (Nd) lasers, or neodymium yttrium-aluminum-garnet (Nd-YAG) lasers. In an aspect, each of the plurality of pores is machined into the material using a waterjet cutter. For example, each of the plurality of pores can be machined into the material using a waterjet cutter with or without an added abrasive, e.g., garnet or aluminum oxide. In an aspect, the plurality of pores is machined into the material to form the semi-permeable material before the semi-permeable material is used to form the flexible tubular structure. In an aspect, the plurality of pores is machined into a material already forming the flexible tubular structure of the gastrointestinal device.

In an aspect, the flexible tubular structure is formed from a substantially impermeably material. In an aspect, the flexible tubular structure is formed from a material that is substantially impermeable to water and components of the ingested food or chyme. For example, the flexible tubular structure may be formed from plastic sheeting that is impermeable to water and other components of the ingested food or chyme. For example, the flexible tubular structure may be configured such that all of the ingested food or chyme that enters the proximal end of the gastrointestinal device passes through the flow conduit of the flexible tubular structure to the distal end without any of the contents of the ingested food or chyme passing laterally through the flexible tubular structure to the underlying portion of the gastrointestinal wall covered by the flexible tubular structure.

In an aspect, the flexible tubular structure is formed from and/or includes radiopaque and/or sonoreflective materials and/or includes one or more radiopaque and/or sonoreflective markers for enhanced imaging by X-ray, fluoroscopy, and/or ultrasonic imaging so that the position and functional state of the flexible tubular structure can be verified noninvasively. In an aspect, the radiopaque material includes a radiopacifier or a material with a higher electron density compared to the surrounding tissue so that it absorbs X-rays. In an aspect, the radiopaque material or radiopacifier includes at least one of gold, tungsten, zirconium oxide, barium sulphate, or bismuth. For example, the flexible tubular structure can be formed with a polymer and a radiopaque filler, e.g., barium sulfate, bismuth compounds, or tungsten. In an aspect, the sonoreflective marker includes reflective "beads." For example, the sonoreflective marker can include reflective beads formed from stainless steel, Nitinol, titanium, and the like. See, e.g., U.S. Patent Application No. 2011/0021888 to Sing titled "Apparatus, Systems, and Methods for Localizing Markers or Tissue Structures within a Body," which is incorporated herein by reference. In an aspect, the sonoreflective marker includes a piezoelectric marker that generates electrical signals when scanned by ultrasound. See, e.g., U.S. Pat. No. 8,282,561 to Towe titled "Piezo Micro-markers for Ultrasound Medical Diagnostics," which is incorporated herein by reference.

Microbes

In some embodiments, the gastrointestinal device includes a plurality of at least one type of commensal microbe associated with at least a portion of at least one of the inner surface and the outer surface of the flexible tubular structure. In an aspect, the at least one type of commensal microbe includes a type of microbe commonly found in the gastrointestinal tract of a given mammalian subject. For example, the at least one type of commensal microbe can include bacterial strains from Firmicutes and/or Bacteroidetes. In an aspect, the choice of the at least one type of commensal microbe depends upon characteristics of the subject, e.g., age, gender, ethnicity, geographical location, medical history, comorbidities, or subject preferences. In an aspect, the choice of the at least one type of commensal microbe depends upon the intended location of the gastrointestinal device within the gastrointestinal tract. For example, the population of microbes may change along the gastrointestinal tract. For example, the distribution of microbes in the esophagus may differ from the distribution of microbes in the stomach. For example, the distribution of microbes in the small intestine may differ from the distribution of microbes in the large intestine. For example, the distribution of microbes may vary in various parts of the small intestine, e.g., the duodenum, jejunum, or ileum, or of the large intestine, e.g., colon and rectum. See, e.g., Andersson, et al. (2008) *PLoS ONE* 3:e2836; and Wang and Yang (2013) *World J Gastroenterol* 19:1541-1550, which are incorporated herein by reference.

In an aspect, the at least one type of commensal microbe includes a plurality of at least one type of gut microbe. In an aspect, the at least one type of gut microbe includes at least one type of the most common gut microbes residing in the intestine. In an aspect, the at least one type of gut microbe can include at least one type of Firmicutes. For example, the at least one type of Firmicutes can include one or more representatives of *Lactobacillus*. In an aspect, the at least one type of gut microbe can include at least one type of Bacteroidetes. For example, the at least one type of gut microbe can include at least one type of Actinobacteria, and/or Proteobacteria. For example, the at least one type of Actinobacteria can include one or more representatives of *Bifidobacterium*.

In an aspect, the at least one type of commensal microbe includes a plurality of at least one type of microbe found in the esophagus. In an aspect, the at least one type of commensal microbe includes a plurality of at least one type of microbe found in the stomach. In an aspect, the at least one type of commensal microbe includes at least one type of *Actinomyces, Gemella, Veillonella*, or *Prevotella*.

In an aspect, the plurality of the at least one type of commensal microbe includes a plurality of at least one type of genetically modified microbe. For example, the least one type of genetically modified microbe can include at least one type of microbe genetically modified to produce a beneficial digestive enzyme (e.g., pepsin, trypsinogen, chymotrypsinogen, carboxypeptidase, pancreatic lipase, sterol esterase, phospholipase, nucleases, sucrose, lactase, or maltase). For example, the at least one type of genetically modified microbe can include at least one type of microbe genetically modified to produce a beneficial hormone (e.g., gastrin, somatostatin, secretin, or cholecystokinin). For example, the at least one type of genetically modified microbe can include at least one type of microbe genetically modified to produce mucin. For example, the at least one type of genetically modified microbe can include at least one type of microbe genetically modified to produce a desired nutrient. For example, the at least one type of genetically modified microbe can include at least one type of microbe genetically modified to interact with endogenous microbes, e.g., to inhibit and/or stimulate the growth of specific endogenous microbes. For example, the at least one type of genetically modified microbe can include at least one type of microbe genetically modified to generate a therapeutic agent (e.g., an antimicrobial agent, anti-inflammatory agent, or a chemotherapeutic agent). One or more types of genetically modified microbes (e.g., genetically modified *Escherichia coli* bacteria) can be generated using standard methods.

In an aspect, the plurality of the at least one type of commensal microbe includes a plurality of at least one type of commensal microbe from a fecal sample. In an aspect, the at least one type of commensal microbe includes at least one type of microbe harvested or isolated from fecal matter. See, e.g., Borody et al. (2013) *Curr. Gastroenterol. Rep.* 15:337, which is incorporated herein by reference. A non-limiting example of harvesting, screening, and preparing fecal matter from donors is described in Bakken et al. (2011) *Clin. Gastroenterol. Hepatol.* 9:1044-1049, which is incorporated herein by reference.

In an aspect, the at least one type of commensal microbe from the fecal sample includes at least one type of commensal microbe from a fecal sample of the subject. For example, the plurality of at least one type of commensal microbe can include at least one type of commensal microbe harvested or isolated from a fecal sample of the subject at a prior point in time, e.g., at an earlier age. For example, the plurality of the at least one type of commensal microbe can include at least one type of commensal microbe harvested or isolated from a fecal sample of the subject prior to onset of a condition, e.g., obesity, metabolic syndrome, bacterial infection, cancer, ulcerative colitis, or inflammatory bowel disease. For example, the plurality of the at least one type of commensal microbe can include at least one type of commensal microbe harvested or isolated from a fecal sample of the subject prior to a procedure (e.g., surgery) or administration of a drug or treatment (e.g., an antibiotic or chemotherapy) known to disrupt intestinal flora. For example, the plurality of the at least one type of commensal microbe can include at least one type of commensal microbe harvested or isolated from a fecal sample of the subject prior to travel to another country and/or exposure to a new diet.

In an aspect, the at least one type of commensal microbe from the fecal sample includes at least one type of commensal microbe from a fecal sample of one or more other individuals. For example, the at least one type of commensal microbe can include at least one type of commensal microbe from a fecal sample of a biological relative of the subject, e.g., a parent, sibling, or child of the subject, or member of a household e.g., a spouse. For example, the at least one type of commensal microbe can include at least one type of commensal microbe from a fecal sample of one or more individuals having a preferred intestinal microbiota. For example, the at least one type of commensal microbe can be isolated from fecal matter harvested from a thin, slim, or normal weight individual for use in a subject who is overweight/obese and/or suffering from metabolic dysfunction. See, e.g., Tilg & Kaser (2011) *J. Clin. Invest.* 121:2126-2132, which is incorporated herein by reference. For example, the at least one type of commensal microbe can include at least one type of microbe from a fecal sample of one or more individuals with a healthy intestinal microbiota. For example, the at least one type of commensal microbe can be isolated from fecal matter harvested from one or more healthy individuals for use in a subject suffering from *Clostridium difficile* infection. See, e.g., Di Bella et al. (2013) *Infect. Dis. Rep.* 5(2):e13, which is incorporated herein by reference.

In an aspect, the plurality of the at least one type of commensal microbe includes at least part of a gut microbiota. In an aspect, the gut microbiota includes one or more microbes associated with the gut flora. In an aspect, the at least part of the gut microbiota includes at least part of a gut microbiota of the subject. In an aspect, the at least part of a gut microbiota of the subject includes at least part of a gut microbiota of the subject determined at a prior point in time. For example, the at least part of a gut microbiota of the subject can include at least part of a gut microbiota of the subject determined at an earlier age so as to replicate at least part of a youthful microbiota. For example, the at least a part of a gut microbiota of the subject can include at least part of a gut microbiota of the subject determined before the onset of a current condition or therapeutic treatment so as to replicate at least part of a healthy or undisturbed microbiota.

In an aspect, the at least part of the gut microbiota includes at least part of a gut microbiota of one or more other individuals. In an aspect, the at least part of the gut microbiota includes at least part of a healthy gut microbiota. In an aspect, the at least part of the healthy gut microbiota is normalized to the subject based on age, gender, ethnicity, geographical location, diet, medical history, or co-morbidities. For example, the healthy gut microbiota may include a gut microbiota from one or more healthy individuals, e.g., individuals not experiencing an intestinal condition such as ulcerative colitis or *Clostridium difficile* infection. In an aspect, the at least part of the gut microbiota includes at least part of a preferred gut microbiota. For example, the preferred gut microbiota may include a gut microbiota from one or more non-obese and/or healthy weight individuals. In an aspect, the at least part of the gut microbiota includes at least part of a theoretical gut microbiota. For example, the at least part of a theoretical gut microbiota can be determined based on computational analysis of the gut microbiota of individuals with a healthy and/or preferred phenotype. In an aspect, the at least part of a gut microbiota is derived from a fecal sample.

In an aspect, the at least part of the gut microbiota is derived from in vitro culture of one or more types of commensal microbes. In an aspect, at least part of the gut microbiota of an individual is generated in vitro from cultured microbes known to be associated with a specific microbiota. For example, at least part of a gut microbiota can be generated by culturing in vitro representative members of the common classes of bacteria found in a healthy, preferred, or theoretical gut microbiota. For example, the at least part of the gut microbiota can include a small number of representatives of Firmicutes, Bacteriodetes, Actinobacteria, and/or Proteobacteria cultured in vitro and combined for association with the inner and/or outer surface of the flexible tubular structure. A variety of bacterial strains, including representative strains of Firmicutes, Bacteriodetes, Actinobacteria, and Proteobacteria are available through the American Type Culture Collection, Manassas, Va.

In an aspect, the plurality of at least one type of commensal microbe includes at least one type of microbe able to affect its gastrointestinal environment. In an aspect, the plurality of at least one type of commensal microbe includes at least one type of microbe able to affect the pH of its environment, thereby promoting the growth of favorable microbes and protecting against infection with deleterious microbes. In an aspect, the plurality of at least one type of commensal microbe includes at least one type of a mucus-stimulating microbe. For example, the at least one type of commensal microbe can include a type of microbe that stimulates cells of the gastrointestinal tract to generate more protective mucus. For example, the at least one type of commensal microbe can include *A. muciniphila*. Other types of microbes capable of acutely increasing intestinal mucus production include *Bifidobacterium bifidum*, *Campylobacter jejuni*, *Cyrptosporidium parvum*, *Entamoeba histolytica*, *E. coli*, *Salmonella*, and *Yersinia*.

In an aspect, the plurality of at least one type of commensal microbe includes at least one type of a microbe that aids in the digestion of food. For example, the plurality of at least one type of commensal microbe can include a type of microbe that breaks down complex sugars, proteins, and fats. For example, the plurality of at least one type of commensal microbe can include *Lactobacilli*. For example, the device may include a microbe that aids in the digestion of food into a product usable by downstream microbes or subject tissues. For example, the device may include a microbe that aids in the digestion of food so that certain substances (e.g., nutrients, micronutrients, or vitamins) or a portion thereof can cross the semi-permeable material of the device and be absorbed or further processed by the gut. In an aspect, the plurality of at least one type of commensal microbe can include at least one type of microbe that generates vitamins or other nutrients. For example, the plurality of at least one type of commensal microbe can include a type of microbe that generates vitamin K, e.g., *Lactobacillus acidophilus*. For example, the plurality of at least one type of commensal microbe can include a type of microbe that generates B-complex vitamins, e.g., lactic acid bacteria and/or enteric bacteria.

In an aspect, the plurality of the at least one type of commensal microbe includes a phylogenetically diverse mini-microbiota. In an aspect, the plurality of the at least one type of commensal microbe includes a simplified microbiota. For example, the simplified microbiota can include a small number of representatives of Firmicutes, Bacteriodetes, Actinobacteria, and/or Proteobacteria. For example, the simplified microbiota can include a defined mixture of phylogenetically diverse intestinal bacteria capable of stimulating re-establishment of a healthy microbiota. See, e.g., Lawley et al. (2012) *PLoS Pathogen* 8(10):e1002995, which is incorporated herein by reference.

In an aspect, the plurality of the at least one type of commensal microbe includes at least one type of probiotic. In an aspect, the at least one type of probiotic includes at least one type of bacteria that benefits mammalian (particularly human) health, particularly gastrointestinal health. In an aspect, the at least one type of probiotic infers a benefit on the host, e.g., the subject. For example, representatives types of *Lactobacillus* and *Bifidobacterium* significantly influence human health through a range of effects including, but not limited to, detoxification of xenobiotics, biosynthesis of vitamin K, metabolic effects of fermentation of indigestible dietary fiber, positive influence on transit of gastrointestinal contents by peristalsis, competition with pathogenic microbes for nutrients and binding sites on mucosal epithelial cells, and modulation of the host immune response. See, e.g., Hardy et al. (2013) *Nutrients* 5:1869-1912, which is incorporated herein by reference.

In an aspect, the plurality of the at least one type of commensal microbe includes at least one type of *Bifidobacterium*. In an aspect, the at least one type of *Bifidobacterium* includes at least one type of *B. adolescentis*. In an aspect, the at least one type of *Bifidobacterium* includes at least one of *B. laterosporus*, *B. breve*, *B. subtilus*, *B. infantis*, *B. longum*, *B. thermophilum*, *B. animalis*, or *B. bifidum*. In an aspect, the plurality of the at least one type of commensal microbe includes at least one type of *Bacteroides*. In an aspect, the plurality of the at least one type of commensal microbe includes at least one type of *Lactobacillus*. In an aspect, the at least one type of *Lactobacillus* includes at least one of *L. acidophilus*, *L. casei*, *L. fermentum*, *L. salivaroes*, *L. brevis*, *L. leichmannii*, *L. plantarum*, or *L. cellobiosius*. Other non-limiting examples of *Lactobacillus* include *L. reuteri*, *L.*

*curvatus, L. bulgaricus, L. gasseri, L. caveasicus, L. helveticus, L. lactis, L. salivarius, L. rhamnosus*, or *L. buchneri*.

Other non-limiting examples of probiotics include *Streptococcus thermphilius, Lactococcus lactis cremoris, S. diacetylactis* and *S. intermedius, L. sporogenes* (also known as *Bacillus coagulans*), *Pediococcus acidilactici* and *Pediococcus pentosaceus*, and *Enterococcus faecium*.

In an aspect, the at least one type of probiotic is available from a commercial source. For example, commercially available strains of *L. acidophilus* include NCRM and *Lactobacillus acidophilus* DDS-1, manufactured by Nebraska Cultures, Inc. and *Lactobacillus rhamnosus* GG, manufactured by LGG—Research and Development, which is deposited in the American Type Culture Collection, coded ATCC 53103. Another commercially available strain of *Lactobacillus* is KE-99 LACTO by Probiohealth, Inc. of Los Angeles, Calif.

In an aspect, the gastrointestinal device with the plurality of at least one type of commensal microbe is beneficial to a subject having a medical condition. In an aspect, the medical condition of the subject includes at least one of diabetes, obesity, metabolic syndrome, colitis, cancer, inflammatory bowel disease, irritable bowel syndrome, an autoimmune disorder, or a microbial infection. In an aspect, the medical condition includes a *Clostridium difficile* infection. In an aspect, the medical condition includes Crohn's disease. In an aspect, the medical condition includes ischemia in a portion of the gastrointestinal tract. In an aspect, the medical condition includes a stricture (e.g., in a patient with Crohn's disease). In an aspect, the medical condition includes an obstruction (e.g., a benign or malignant growth). In an aspect, the medical condition includes an irritation or damage to a portion of the gastrointestinal tract. In an aspect, the medical condition includes trauma to a portion of the gastrointestinal tract, for example trauma from injury or due to surgery (e.g., excision of tissue or recision of a portion of the gastrointestinal tract).

In an aspect, the gastrointestinal device replaces or supports a defective or at risk portion of the gastrointestinal tract. In an aspect, the gastrointestinal device acts as an artificial gut. For example, the gastrointestinal device can provide a microbial environment in the form of the plurality of the at least one type of commensal microbe that interacts with ingested food or chyme or with the gastrointestinal wall. In an aspect, the gastrointestinal device includes a plurality of at least one type of commensal microbes that replaces the digestive and/or nutritional functions of endogenous microbes that are otherwise covered by a portion of the gastrointestinal device. In an aspect, the plurality of the at least one type of commensal microbe forms a microbiome.

In an aspect, the at least one type of commensal microbe is beneficial to the subject. In an aspect, the at least one type of commensal microbe is beneficial to the immune system of the subject. For example, the at least type of commensal microbe can include *Bacteroides thetaiotaomicron* which has been demonstrated to attenuate *Salmonella enterica*-induced inflammation. See, e.g., Wu & Wu (2012) *Gut Microbes* 3:1, 4-14, which is incorporated herein by reference. In an aspect, the at least one type of commensal microbe is beneficial to a dietary condition of the subject. In an aspect, the dietary condition of the subject includes a dietary need of the subject (e.g., a nutritional need), weight control of the subject (e.g., obesity), or a food sensitivity of the subject (e.g., a gluten sensitivity or inability to digest lactose). For example, the at least one type of commensal microbe can be a source of digestive enzyme needed to break down complex carbohydrates. For example, several bacterial genera, e.g., *Bacteroides, Bifidobacterium*, and *Enterococcus*, are known to synthesize vitamins, e.g., thiamine, folate, biotin, riboflavin, and pathothenic acid. See, e.g., Morowitz et al. (2011) *Surg. Clin. North Am.* 91:771-785, which is incorporated herein by reference. For example, the at least one type of commensal microbe can include *Lactobacillus gasseri* SBT2005, which has been shown to regulate abdominal adiposity in adults with obese tendencies. See, e.g., Kadooka et al. (2010) *Eur. J. Clin. Nutr.* 64:636-643, which is incorporated herein by reference. For example, the at least one type of commensal microbe can include *Bifidobacterium lactis* HN019 and/or *Lactobacillus acidophilus* NCFM, which have been shown to alleviate lactose intolerance. See, e.g., Grover et al. (2012) *Gut Pathogens* 4:15, which is incorporated herein by reference.

In an aspect, the at least one type of commensal microbe is beneficial to a medical condition of the subject. In an aspect, the medical condition includes diabetes, metabolic syndrome, obesity, cancer, colitis, inflammatory bowel disease, irritable bowel syndrome, autoimmune disorder, ischemia, a microbial infection, or a microbial deficit. In an aspect, the at least one type of commensal microbe is beneficial to the subject with a *Clostridium difficile* infection. In an aspect, the at least one type of commensal microbe is beneficial to the subject with Crohn's disease. See, e.g., Baxter et al. (2014) *Microbiome* 2:20; Moreno-Indias et al. (2014) *Front. Microbiol.* 5:190; Allegretti & Hamilton (2014) *World J. Gastroenterol.* 20:3468-3474, which are incorporated herein by reference.

In an aspect, the plurality of the at least one type of commensal microbe forms a coating on the at least a portion of the at least one of the inner surface and the outer surface of the flexible tubular structure. In an aspect, the plurality of the at least one type of commensal microbe forms a biofilm on the at least a portion of the at least one of the inner surface and the outer surface of the flexible tubular structure.

In an aspect, the plurality of the at least one type of commensal microbe is associated with a coating material on the at least a portion of the at least one of the inner surface and the outer surface of the flexible tubular structure. For example, the plurality of the at least one type of commensal microbe can be combined with a coating material prior to application to the flexible tubular structure. For example, the plurality of the at least one type of commensal microbe can be applied to the flexible tubular structure followed by application of a coating material. For example, a coating material can be applied to at least a portion of the at least one of the inner surface and the outer surface followed by application of the plurality of the at least one type of commensal microbe. In an aspect, the coating material includes at least one of a degradable coating material, a matrix coating material, a fibrous coating material, a hydrogel coating material, or a mucus coating material.

In an aspect, the plurality of the at least one type of commensal microbe is incorporated into a degradable coating on the at least a portion of the at least one of the inner surface and the outer surface of the flexible tubular structure.

In an aspect, coating material includes a matrix coating material. In an aspect, the matrix coating material includes proteins associated with extracellular matrix and/or connective tissue. For example, the matrix coating material can include collagen, fibronectin, fibrin, and/or elastin fibers derived from natural sources or from genetic engineering. See, e.g., Gomes et al. (2012) *Prog. Polym Sci.* 37:1-17, which is incorporated herein by reference.

In an aspect, the coating material includes a fibrous coating material. For example, the coating material can include a fibrous material configured to allow the plurality of the at least one type of commensal microbe to diffuse into and out of the coating material. In an aspect, the fibrous coating material includes cellulose. In an aspect, the fibrous coating material includes a polymer. See, e.g., U.S. Patent Application No. 2013/0131756 to Arnholt et al. titled "Fibrous Matrix Coating Material," which is incorporated herein by reference.

In an aspect, the coating material includes a hydrogel coating material. In an aspect, the hydrogel coating material includes one or more natural polymers, one or more synthetic monomers, or a combination there of. Non-limiting examples of natural polymers for use in forming hydrogels include chitosan, alginate, fibrin, collagen, gelatin, hyaluronic acid, and dextran. Non-limiting examples of synthetic monomers for use in forming hydrogels include hydroxyethyl methacrylate (HEMA), N-(2-hydroxypropyl) methacrylate (HPMA), N-vinyl-2-pyrrolidone (NVP), N-isopropyl acrylamide (NIPAAm), vinyl acetate (VAc), acrylic acid (AA), methacrylic acid (MAA), polyethylene glycol acrylate/methacrylate (PEGA/PEGMA), polyethylene glycol diacrylate/dimethacrylate (PEGDA/PEGDMA). See, e.g., Lin & Metters (2006) *Adv. Drug Deliv. Res.* 58:1379-1408, which is incorporated herein by reference.

In an aspect, the coating includes a mucus coating material. In an aspect, the mucus coating material includes a natural mucus coating material. For example, the plurality of the at least one type of commensal microbe can be associated with a natural mucus coating on the inner surface and/or outer surface of the flexible tubular structure. For example, natural mucus can be isolated from a mammalian tissue, e.g., intestinal tissue, by gently scraping the mucosal layer off of a resected piece of tissue and rinsing in buffer. Natural mucus can also be isolated from feces and/or ileostomy effluent. See, e.g., Ouwehand et al. (2001) *Methods Enzymol.* 337:200-212, which is incorporated herein by reference.

In an aspect, the mucus coating material includes a synthetic mucus coating material. For example, the synthetic mucus coating material can be formed in vitro from one or more common components of mucus, e.g., mucin glycoproteins. For example, the synthetic mucus coating material can include mucin MUC2. For example, the synthetic mucus coating material can include at least one secreted mucin including at least one of MUC2, MUC5AC, MUC5B, MUC6, MUC7, MUC 8, or MUC19. For example, the synthetic mucus coating material can include at least one membrane-bound mucin including least one of MUC1, MUC3A, MUC3B, MUC4, MUC12, MUC13, MUC15, MUC16, MUC17, or MUC20. In an aspect, the synthetic mucus coating material is formed from mucins proteins or any of a group of protein-containing glycoconjugates with high sialic acid or sulfated polysaccharide content that compose the chief constituent of mucus. In an aspect, the synthetic mucus coating material includes a wide variety of glycoconjugates, including mucoproteins, glycoproteins, glycosaminoglycans, and glycolipids.

In an aspect, the mucus coating material is derived from cultured epithelial cells. For example, the cultured epithelial cells can include cultured intestinal epithelial cells. For example, the epithelial cells can include stem cells, e.g., embryonic or mesenchymal stem cells. For example, various lineages of intestinal epithelial cells can be derived from crypt base columnar cells isolated from the bottom of intestinal crypts. See, e.g., Fujii & Sato (2014) *Frontiers in Genetics*, volume 5, article 169, published June 2014, which is incorporated herein by reference. In an aspect, the mucus coating material is produced by a monolayer of cells, e.g., intestinal submucosal cells or cultured intestinal epithelial cells, grown on the inner surface and/or outer surface of the flexible tubular structure.

In an aspect, the plurality of the at least one type of commensal microbe is bound to the at least a portion of the at least one of the inner surface and the outer surface of the flexible tubular structure. In an aspect, at least one of the plurality of the at least one type of commensal microbe is bound through at least one selective binding agent to the at least a portion of the at least one of the inner surface and the outer surface of the flexible tubular structure. For example, the at least one type of commensal microbe may be bound to the inner and/or outer surface of the flexible tubular structure through an antibody, aptamer, or other selective binding agent that selectively recognizes and binds components expressed on the exterior of the at least on type of commensal microbe. In an aspect, at least one of the plurality of the at least one type of commensal microbe is bound through at least one non-selective binding agent to the at least a portion of the at least one of the inner surface and the outer surface of the flexible tubular structure. For example, the at least one type of commensal microbe may be bound to the inner and/or outer surface of the flexible tubular structure through an absorbent, an adsorbent, an adhesive, a gel, or a matrix.

In an aspect, the plurality of the at least one type of commensal microbe is non-covalently attached to the at least a portion of the at least one of the inner surface and the outer surface of the flexible tubular structure. Non-limiting examples of non-covalent interactions include hydrogen bonds, ionic bonds, van der Waals forces, and hydrophobic interactions. In an aspect, the plurality of the at least one type of commensal microbe is non-covalently attached to the substrate through protein-protein interactions, e.g., an avidin/biotin protein interaction. For example, the at least one type of commensal microbe can be modified with biotin and non-covalently attached to a surface of the flexible tubular structure that includes streptavidin or avidin. Other non-limiting examples non-covalent interactions include interactions between ligands and receptors. In an aspect, the plurality of the at least one type of commensal microbe is recognizes and binds to an antibody or other binding ligand/receptor associated with at least a portion of the inner surface and/or the outer surface of the flexible tubular structure.

In an aspect, the plurality of the at least one type of commensal microbe is irreversibly associated with at least a portion of at least one of the inner surface and the outer surface of the flexible tubular structure. For example, the plurality of the at least one type of commensal microbe can be trapped on the inner and/or outer surface of the flexible tubular structure. For example, the plurality of the at least one type of commensal microbe can be trapped in an enclosure, e.g., a layered wall, associated with the inner and/or outer surface of the flexible tubular structure. For example, the plurality of at least one type of commensal microbe can be trapped in an alginate enclosure. For example, the plurality of at least one type of commensal microbe can be trapped in a mesh enclosure.

In an aspect, the plurality of at least one type of commensal microbe is reversibly associated with the inner and/or outer surface of the flexible tubular structure. In an aspect, at least one of the plurality of the at least one type of commensal microbe migrates or diffuses from the inner and/or outer surface of the flexible tubular structure with the flow of the ingested contents of the gastrointestinal tract, for example, with the natural turn-over that occurs with the growth of a microbial population. In an aspect, the plurality of at least one type of commensal microbe is associated with a fibrous, porous, or gel matrix. In an aspect, the plurality of at least one type of commensal microbe is associated with a fibrous, porous, or gel matrix from which a portion of the at least one type of commensal microbe is able to diffuse over time. In an aspect, the plurality of at least one type of commensal microbe is encased in a degradable material, e.g., a pH degradable material, that breaks down over time, slowly exposing a portion of the at least one type of commensal microbe from the inner and/or outer surface of the flexible tubular structure.

In an aspect, the plurality of the at least one type of commensal microbe is incorporated into a coating. In an aspect, the plurality of the at least one type of commensal microbe is incorporated into a degradable coating on the at least a portion of the at least one of the inner surface and the outer surface of the flexible tubular structure. For example, the plurality of the at least one type of commensal microbe can be incorporated into a coating material that degrades over time to expose the at least one type of commensal microbe. For example, the degradable coating can further include prebiotics, therapeutic agents, or bioactive agents that are released as the coating degrades. In an aspect, the plurality of the at least one type of commensal microbe is incorporated into a stimulus-responsive degradable coating on the at least a portion of the at least one of the inner surface and the outer surface of the flexible tubular structure. For example, the plurality of the at least one type of commensal microbe can be incorporated into a coating material that degrades in response to a stimulus, e.g., time, moisture, temperature, pH, or chemicals.

In an aspect, the stimulus-responsive degradable coating includes at least one of a time-responsive degradable coating, a moisture-responsive degradable coating, a temperature-responsive degradable coating, a pH-responsive degradable coating, or a chemical-responsive degradable coating. In an aspect, the stimulus-responsive degradable coating includes a time-responsive degradable coating. For example, the plurality of the at least one type of commensal microbe can be incorporated into a time-responsive degradable coating that degrades over time to expose the at least one type of commensal microbe. In an aspect, the stimulus-responsive degradable coating includes a moisture-responsive degradable coating. For example, the plurality of the at least one type of commensal microbe can be incorporated into a moisture-responsive degradable coating that degrades over time in responsive to moisture associated with the gastrointestinal tract to expose the at least one type of commensal microbe.

In an aspect, the stimulus-responsive degradable coating includes a temperature-responsive degradable coating. For example, the plurality of the at least one type of commensal microbe can be incorporated into a temperature-responsive degradable coating that degrades over time in response to body heat, e.g., 37 degrees centigrade, associated with the gastrointestinal tract to expose the at least one type of commensal microbe. For example, the plurality of the at least one type commensal microbe can be incorporated into a pH-responsive degradable coating that degrades over time in response to pH changes in the gastrointestinal tract as ingested material moves from the stomach (pH 1.0-3.0) into the upper (pH 4.8-8.2) and the lower (pH 7.0-7.5) intestinal tract to expose the at least one type of commensal microbe.

Non-limiting examples of temperature-responsive and pH-responsive polymers are described in Schmaljohann (2006) Adv. Drug Deliv. Rev. 58:1655-1670, which is incorporated herein by reference.

In an aspect, the stimulus-responsive degradable coating includes a chemical-responsive degradable coating. For example, the plurality of the at least one type of commensal microbe can be incorporated into a chemical-responsive degradable coating that degrades in response to either an endogenous chemical or an administered/ingested chemical to expose the at least one type of commensal microbe. For example, the chemical-responsive degradable coating can include a hydrogel that is responsive to a chemical, e.g., glucose, a protein, an antibody, or an aptamer. See, e.g., Yang et al. (2008) J. Am. Chem. Soc. 130:6320-6321; Miyata et al. (2006) Proc. Natl. Acad. Sci. 103:1190-1193, which are incorporated herein by reference.

In an aspect, the device further includes a plurality of at least one first type of commensal microbe in a first degradable coating and a plurality of at least one second type of commensal microbe in a second degradable coating. In an aspect, the first degradable coating and the second degradable coating degrade at different rates. For example, the plurality of the at least one first type of commensal microbe can be in a first time-responsive degradable coating configured to degrade at a first rate and the plurality of the at least one second type of commensal microbe can be in a second time-responsive degradable coating configured to degrade at a second rate. For example, the plurality of the at least one first type of commensal microbe can be in a first stimulus-responsive degradable coating and the plurality of the at least one second type of commensal microbe in a second stimulus-responsive degradable coating, the first stimulus-responsive degradable coating degrading at a different pH or temperature than the second stimulus-responsive degradable coating. For example, the plurality of the at least one first type of commensal microbe can be in a first chemical-responsive degradable coating and the plurality of the at least one second type of commensal microbe in a second chemical-responsive degradable coating, the first chemical-responsive degradable coating degrading in response to a first chemical and the second chemical-responsive degradable coating degrading in response to a second chemical.

Anchoring Mechanism

The gastrointestinal device includes at least one anchor structure associated with the flexible tubular structure, the at least one anchor structure including one or more gastric wall-engaging components. In an aspect, the at least one anchor structure is attached to the proximal end of the flexible tubular structure. In an aspect, the at least one anchor structure is attached to the distal end of the flexible tubular structure. In an aspect, the at least one anchor structure includes a space occupying ring, an inflatable balloon, a self-expanding anchor, or frame, barbs, hooks, springs, coils, disks, or any combination thereof. In an aspect, the gastric wall-engaging component includes an outer surface of a space occupying ring, inflatable balloon, springs, coils, and/or disks that engages a wall of the gastrointestinal tract by exerting an outward or radial force on the wall. In an aspect, the gastric wall-engaging component includes a barb, a hook, a surgical staple, or other component that engages a wall of the gastrointestinal tract by grabbing, e.g., hooking onto, the wall. In an aspect, the gastric wall-engaging component includes a chemical wall-engaging component, e.g., a surgical adhesive. In an aspect, the gastric wall-engaging component includes a clip. In an aspect, the one or more gastric wall-engaging components are configured to engage the wall of the esophagus. In an aspect, the one or more gastric wall-engaging components are configured to engage the wall of the stomach. In an aspect, the one or more gastric wall-engaging components are configured to engage the wall of the pylorus. In an aspect, the one or more gastric wall-engaging components are configured to engage the wall of the pyloric sphincter. For example, the one or more gastric wall-engaging components can include components on each side of the pyloric sphincter. See, e.g., U.S. Patent Application No. 2012/0184893 to Thompson et al. titled "Anchors and Methods for Intestinal Bypass Sleeves," which is incorporated herein by reference. In an aspect, the one or more gastric wall-engaging components are engaged with the wall of the duodenum. In an aspect, the one or more gastric wall-engaging components are engaged with the wall of the jejunum. In an aspect, the one or more gastric wall-engaging components are engaged with the wall of the colon and/or rectum.

In an aspect, the at least one anchor structure includes a flow conduit continuous with the flow conduit formed by the proximal and distal ends of the flexible tubular structure. For example, the at least one anchor structure can include a ring structure defining a central aperture contiguous with the flow conduit of the flexible tubular structure and including one or more gastric wall-engaging components for engaging the wall of the gastrointestinal tract and anchoring the gastrointestinal device. For example, the at least one anchor structure can be toroid in shape, e.g., donut-shaped, with the outer portion of the toroid pressed radially against the wall of a portion of the gastrointestinal tract. See, e.g., U.S. Patent Application No. 2014/0012178 to Chin titled "Systems and Methods for Bariatric Therapy." For example, a donut shaped anchor structure can define a central hole through which food or partially digested food can pass into the flexible tubular structure.

Figure 5A:
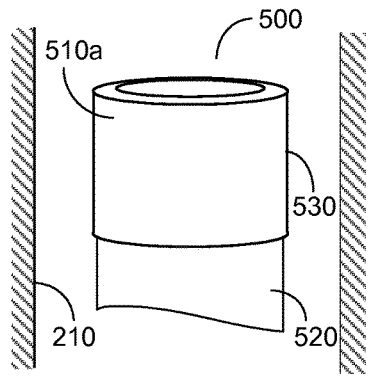
FIG. 5A is a schematic of an anchor structure for a gastrointestinal device in a retracted state.
Figure 5B:
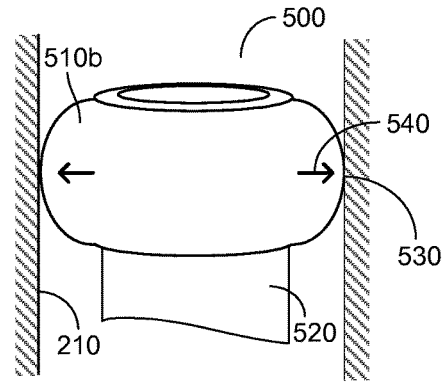
FIG. 5B is a schematic of an anchor structure for a gastrointestinal device in an expanded state.

FIGS. 5A and 5B illustrate aspects of an inflatable anchor structure. FIG. 5A shows a schematic of gastrointestinal device 500 placed in proximity to the gastrointestinal wall 210. Gastrointestinal device 500 includes anchor structure 510a and flexible tubular structure 520. Anchor structure 510a is an inflatable anchor structure and includes one or more gastric wall-engaging components 530 (i.e., the outer surface of the inflatable anchor). FIG. 5B shows gastrointestinal device 500 including anchor structure 510b and flexible tubular structure 520. Anchor structure 510b is an inflated form of anchor structure 510a shown in FIG. 5A which pushes out laterally as shown by arrows 540. Gastric wall-engaging component 530 of anchor structure 510b is now shown touching the gastrointestinal wall 210, anchoring gastrointestinal device 500 in the gastrointestinal tract.

In an aspect, the at least one anchor structure is inflatable. For example, the anchor structure can include an inflatable balloon or donut-shaped structure which when inflated expands radially to engage the wall of the gastrointestinal tract. See, e.g., U.S. Patent Application No. 2014/0012178 to Chin titled "Systems and Methods for Bariatric Therapy," which is incorporated herein by reference. In an aspect, the at least one anchor structure is formed from a thin-walled material. For example, the anchor structure can be formed from an expandable thin sheet of nylon or latex. In an aspect, the at least one anchor structure is formed from a biocompatible material. In an aspect, the at least one anchor structure is formed from a degradable material (e.g., a degradable polymer).

Figure 6A:
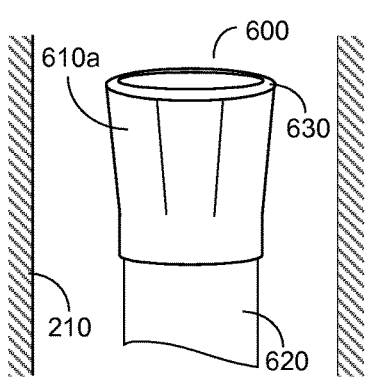
FIG. 6A is a schematic of an anchor structure for a gastrointestinal device in a retracted state.
Figure 6B:
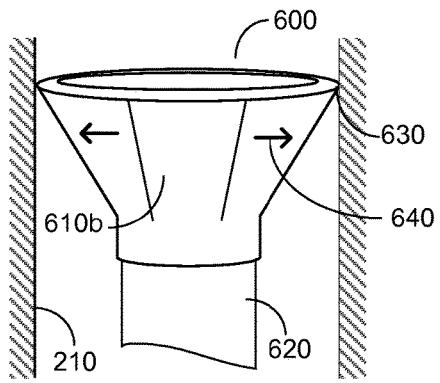
FIG. 6B is a schematic of an anchor structure for a gastrointestinal device in an expanded state.

FIGS. 6A and 6B illustrate aspects of an unfoldable anchor structure. FIG. 6A shows a schematic of gastrointestinal device 600 placed in proximity to the gastrointestinal wall 210. Gastrointestinal device 600 includes anchor structure 610a and flexible tubular structure 620. Anchor structure 610a is an unfoldable anchor structure and includes one or more gastric wall-engaging components 630 (e.g., at least a portion of the outer surface of the unfoldable anchor structure). FIG. 6B shows gastrointestinal device 600 includes anchor structure 610b and flexible tubular structure 620. Anchor structure 610b is an unfolded form of anchor structure 610a shown in FIG. 6A which pushes out laterally as shown by arrows 640. Gastric wall-engaging component 640 of anchor structure 610b is now shown touching the gastrointestinal wall 210, anchoring gastrointestinal device 600 in the gastrointestinal tract.

In an aspect, the at least one anchor structure is expandable. For example, the at least one anchor structure can include an expandable anchor structure that expands upon placement into the gastrointestinal tract. In an aspect, the expandable anchor structure is self-expanding, being formed from an elastic polymer or shape-memory alloy. In an aspect, the at least one anchor structure includes a compressible or collapsible anchor which expands upon placement into the gastrointestinal tract. For example, the at least one anchor structure can include a structure having coils or springs that expand to engage a wall of the gastrointestinal tract. For example, the at least one anchor structure can include expandable disks or rings that expand to engage a wall of the gastrointestinal tract. See, e.g., U.S. Patent Application No. 2012/0184893 to Thompson et al. titled "Anchors and Methods for Intestinal Bypass Sleeves," which is incorporated herein by reference. In an aspect, the at least one anchor structure expands to exert a force against the gastrointestinal wall, anchoring the gastrointestinal device in the gastrointestinal tract. See, e.g., U.S. Pat. No. 7,976,488 to Levine & Melanson titled "Gastrointestinal Anchor Compliance," which is incorporated herein by reference.

In an aspect, the at least one anchor structure is a self-expanding. In an aspect, the self-expanding anchor structure includes a self-expanding cone-shaped anchor structure, a non-limiting example of which is shown in FIGS. 6A and 6B. In an aspect, the self-expanding anchor structure includes two or more arms or wings that spring out radially to engage the wall of the gastrointestinal tract. See, e.g., U.S. Patent Application No. 2014/0012178 to Chin titled "Systems and Methods for Bariatric Therapy," which is incorporated herein by reference. In an aspect, the self-expanding anchor structure includes a stent-like anchor structure to which the flexible tubular structure is attached. See, e.g., U.S. Pat. No. 7,025,791 to Levine et al. titled "Bariatric Sleeve," which is incorporated herein by reference.

Figures 7A, 7B:
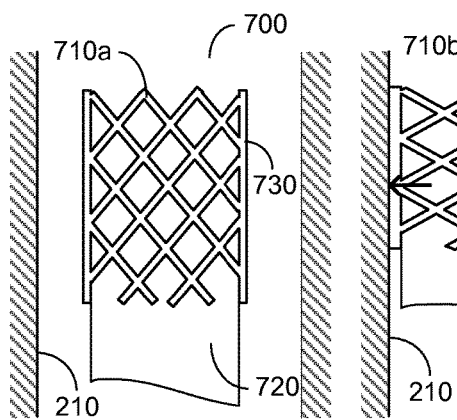
FIG. 7A is a schematic of an anchor structure for a gastrointestinal device in a retracted state.
FIG. 7B is a schematic of an anchor structure for a gastrointestinal device in an expanded state.

FIGS. 7A and 7B illustrate aspects of an expandable anchor structure. FIG. 7A shows a schematic of gastrointestinal device 700 placed in proximity to the gastrointestinal wall 210. Gastrointestinal device 700 includes anchor structure 710a and flexible tubular structure 720. Anchor structure 710a is an expandable stent-like anchor structure and includes one or more gastric wall-engaging components 730 (e.g., at least a portion of the outer surface of the expandable stent-like anchor structure). FIG. 7B shows gastrointestinal device 700 includes anchor structure 710b and flexible tubular structure 720. Anchor structure 710b is an expanded form of anchor structure 710a shown in FIG. 7A which pushes out laterally as shown by arrows 740. Gastric wall-engaging component 740 of anchor structure

710*b* is now shown touching the gastrointestinal wall 210, anchoring gastrointestinal device 700 in the gastrointestinal tract.

Figure 8:
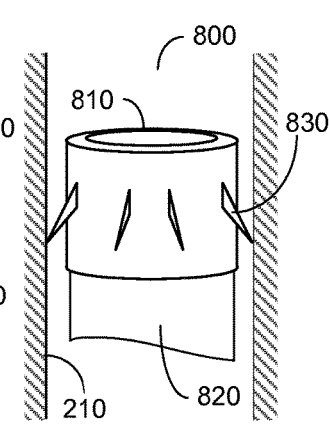
FIG. 8 is a schematic of an anchor structure for a gastrointestinal device with gastric wall-engaging components.

FIG. 8 illustrates aspects of an anchor structure including one or more hooks or barbs. Gastrointestinal device 800 is shown anchored in the gastrointestinal wall 210. Gastrointestinal device 800 includes anchor structure 810 and flexible tubular structure 820. Anchor structure 810 further includes one or more gastric wall-engaging components 830 (e.g., hooks or barbs). The one or more gastric wall-engaging components 830 are shown engaged with the gastrointestinal wall 210, anchoring gastrointestinal device 800 into the gastrointestinal tract.

In an aspect, the anchor structure includes one or more hooks or barbs for engaging the wall of the gastrointestinal tract. In an aspect, the one or more hooks or barbs extend out from the outer surface of the anchor structure. For example, the one or more hooks or barbs can extend about 2 mm or greater from the outer surface of the anchor structure to engage the wall of the gastrointestinal tract. In an aspect, the one or more hooks or barbs engage, e.g., extend into, the musculature of the gastrointestinal tract. In an aspect, the one or more hooks or barbs are positioned so as to point in the direction of forward peristaltic motion. In an aspect, the one or more hooks or barbs are bi-directional to prevent movement of the gastrointestinal device in either direction within the gastrointestinal tract. For example, one or more of the hooks or barbs can be pointed in the direction of forward peristalsis, i.e., the normal flow of ingested food through the gastrointestinal tract, while one or more of the hooks or barbs are pointed in the opposite direction to secure the gastrointestinal device against reverse motion in the gastrointestinal tract. In an aspect, the one or more hooks or barbs are retractable. In an aspect, the one or more hooks or barbs are formed from a degradable material, degrading over a period of time and allowing the gastrointestinal device to dislodge from the wall and to pass through the remainder of the gastrointestinal tract.

In an aspect, the at least one anchor structure is attached to the proximal end of the flexible tubular structure. In an aspect, the at least one anchor structure is attached to the distal end of the flexible tubular structure. In an aspect, the gastrointestinal device includes at least one second anchor structure. In an aspect, the gastrointestinal device includes a second anchor structure associated with the distal end of the flexible tubular structure. In an aspect, at least one anchor structure is attached to the proximal end of the flexible tubular structure and at least one anchor structure is attached to the distal end of the flexible tubular structure.

FIG. 9 illustrates a non-limiting example of a gastrointestinal device with two anchor structures. Shown is gastrointestinal device 900 positioned in the gastrointestinal tract 210 of a subject. Gastrointestinal device 900 includes a flexible tubular structure 910 including an anchor structure 920 at the proximal end 930 of the flexible tubular structure 910 and an anchor structure 920 at the distal end 940 of the flexible tubular structure 910. The gastric wall-engaging portions of anchor structures 920 are shown engaging the wall of gastrointestinal tract 210.

In an aspect, the gastrointestinal device includes one or more gastric wall-engaging components positioned along at least a portion of the flexible tubular structure. In an aspect, the gastrointestinal device includes one or more anchor structures associated with positions along the length of the flexible tubular structure. For example, the gastrointestinal device can include a series of expandable rings running the length of the flexible tubular structure, each of the expandable rings expanding radially to engage the wall of the gastrointestinal tract. In an aspect, the gastrointestinal device includes one or more gastric wall-engaging components positioned laterally to at least a portion of the flexible tubular structure. In an aspect, the gastrointestinal device includes one or more gastric wall-engaging components positioned longitudinally to at least a portion of the flexible tubular structure. In an aspect, the gastrointestinal device includes one or more gastric wall-engaging components positioned along the length of at least a portion of the flexible tubular structure.

FIG. 10 illustrates a non-limiting example of a gastrointestinal device with multiple anchor structures. Shown is gastrointestinal device 1000 positioned in the gastrointestinal tract 210 of a subject. Gastrointestinal device 1000 includes a flexible tubular structure 1010 and anchor structures 1020 positioned along at least a portion of flexible tubular structure 1010. The gastric wall-engaging components of anchor structures 1020 are shown engaging the wall of gastrointestinal tract 210.

In an aspect, the anchor structure is associated with the proximal end of the flexible tubular structure and is engaged with the wall of the stomach, but the flexible tubular structure extends through the pylorus and into the duodenum. In an aspect, the anchor structure, by virtue of size and/or shape, anchors the gastrointestinal device in a portion of the gastrointestinal tract. FIG. 11 illustrates a non-limiting example of a gastrointestinal device spanning the distance between the stomach and the duodenum. Shown is gastrointestinal device 1100 positioned in the gastrointestinal tract of a subject. Gastrointestinal device 1100 includes anchor structure 1120 attached to the proximal end of flexible tubular structure 1110. Anchor structure 1120 is shown engaged with the wall of the stomach 1130. Flexible tubular structure 1110 extends through the pylorus 1140 and into the duodenum 1150. The size and shape of anchor structure 1120 prevents gastrointestinal device 1100 from passing entirely through pylorus 1140.

In an aspect, the at least one anchor structure is incorporated into the flexible tubular structure. In an aspect, the entirety of the flexible tubular structure is an anchor structure. For example, the flexible tubular structure of the gastrointestinal device can include an expandable stent, radial extension of which engages the walls of the gastrointestinal tract and fixes the gastrointestinal device in place.

In an aspect, the one or more gastric wall-engaging components include an adhesive or an adherent. For example, the one or more gastric wall-engaging components can include a surgical adhesive. For example, the adhesive or adherent can include at least one of cyanoacrylate, octyl-2-cyanoacrylate, or n-butyl-cyanoacrylate. For example, the adhesive or adherent can include fibrin glue. For example, the adhesive or adherent can include collagen-based compounds. For example, the adhesive or adherent can include glutaraldehyde glues. For example, the adhesive or adherent can include synthetic polyethylene glycols.

In an aspect, the at least one anchor structure is integral with the proximal end of the flexible tubular structure, being formed from the same material. In an aspect, the at least one anchor structure is formed independently from the flexible tubular structure and subsequently coupled to the flexible tubular structure. In an aspect, the at least one anchor structure is formed independently from the flexible tubular structure and subsequently coupled to the flexible tubular structure during or after insertion. For example, the at least one anchor structure can include at least one clip, e.g., an endoscopic clip.

In an aspect, at least a portion of the at least one anchor structure is formed from a shape memory alloy, e.g., nickel titanium alloys (Nitinol). In an aspect, at least a portion of the at least one anchor structure is formed from any of a number of other suitable alloys or metals, non-limiting examples of which include stainless steel alloys (e.g., 304, 316L, BioDur® 108 Alloy, Pyromet® Alloy CTX-909, Pyromet® Alloy CTX-3, Pyromet® Alloy 31, Pyromet® Alloy CTX-1, 21Cr-6Ni-9Mn Stainless, 21Cr-6Ni-9Mn stainless, Pyromet® Alloy 350, 18Cr-2Ni-12Mn Stainless, Custom 630 (17Cr-4Ni) Stainless, Custom 465® Stainless, Custom 455® Stainless, Custom 450® Stainless, Carpenter 13-8 Stainless, Type 440C Stainless, cobalt chromium alloys—MP35N, Elgiloy, L605, Biodur® Carpenter CCM alloy, Titanium and titanium alloys, Ti-6Al-4V/ELI and Ti-6Al-7Nb, Ti-15Mo, Tantalum, Tungsten and tungsten alloys, pure platinum, platinum-iridium alloys, platinum-nickel alloys, niobium, iridium, conichrome, gold and gold alloys.

In an aspect, at least a portion of the at least one anchor structure is formed from an absorbable metal, nonlimiting examples of which include pure iron and magnesium alloys.

In an aspect, at least a portion of the at least one anchor structure is formed from one or more plastics, nonlimiting examples of which include polyetheretherketone (PEEK), polycarbonate, polyolefins, polyethylenes, polyether block amides (PEBAX), nylon 6, 6-6, 12, polypropylene, polyesters, polyurethanes, polytetrafluoroethylene (PTFE), poly (phenylene sulfide) (PPS), poly(butylene terephthalate) PBT, polysulfone, polyamide, polyimide, poly(p-phenylene oxide) PPO, acrylonitrile butadiene styrene (ABS), polystyrene, poly(methyl methacrylate) (PMMA), polyoxymethylene (POM), ethylene vinyl acetate, styrene acrylonitrile resin, or polybutylene.

In an aspect, at least a portion of the at least one anchor structure is formed from an absorbable polymer, non-limiting examples of which include polyglycolic acid (PGA), polylactide (PLA), poly(.epsilon.-caprolactone), poly(dioxanone), or poly(lactide-co-glycolide).

In an aspect, the at least one anchor structure is formed from and/or includes radiopaque and/or sonoreflective materials and/or includes one or more radiopaque and/or sonoreflective markers for enhanced imaging by X-ray, fluoroscopy, and/or ultrasonic imaging so that the position and functional state of the anchor structure can be verified noninvasively. In an aspect, the radiopaque material includes a radiopacifier or a material with a higher electron density compared to the surrounding tissue so that it absorbs X-rays. In an aspect, the radiopaque material or radiopacifier includes at least one of gold, tungsten, zirconium oxide, barium sulphate, or bismuth. For example, the anchor structure can be formed from a polymer mixed with a radiopaque filler, e.g., barium sulfate, bismuth compounds, or tungsten. In an aspect, the sonoreflective marker includes reflective "beads." For example, the sonoreflective marker can include reflective beads formed from stainless steel, Nitinol, titanium, and the like. See, e.g., U.S. Patent Application No. 2011/0021888 to Sing titled "Apparatus, Systems, and Methods for Localizing Markers or Tissue Structures within a Body," which is incorporated herein by reference. In an aspect, the sonoreflective marker includes a piezoelectric marker that generates electrical signals when scanned by ultrasound. See, e.g., U.S. Pat. No. 8,282,561 to Towe titled "Piezo Micro-markers for Ultrasound Medical Diagnostics," which is incorporated herein by reference.

Figure 12:
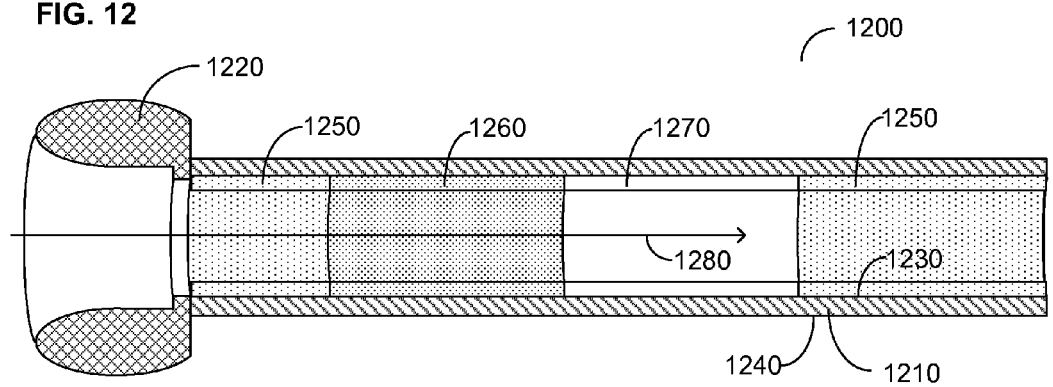
FIG. 12 is a schematic of a cross-section through gastrointestinal device including multiple types of microbes on an inner surface.
Figure 13:
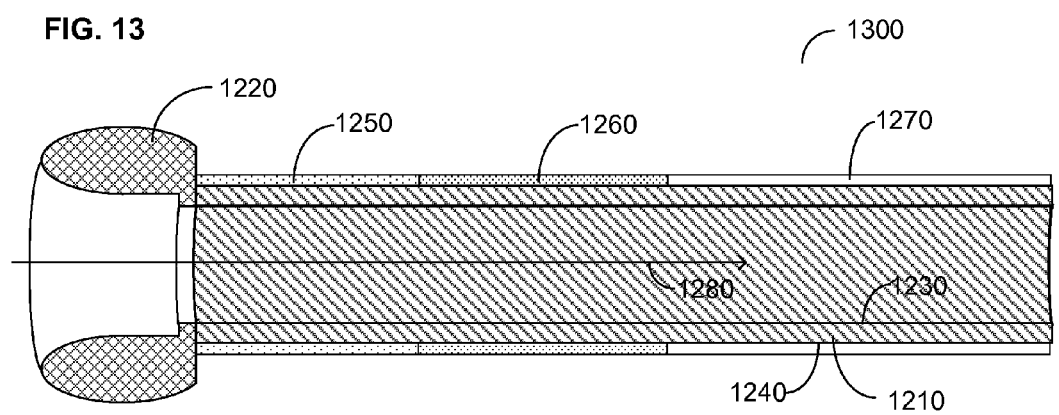
FIG. 13 is a schematic of a cross-section through a gastrointestinal device including multiple types of microbes on an outer surface.
Figure 14:
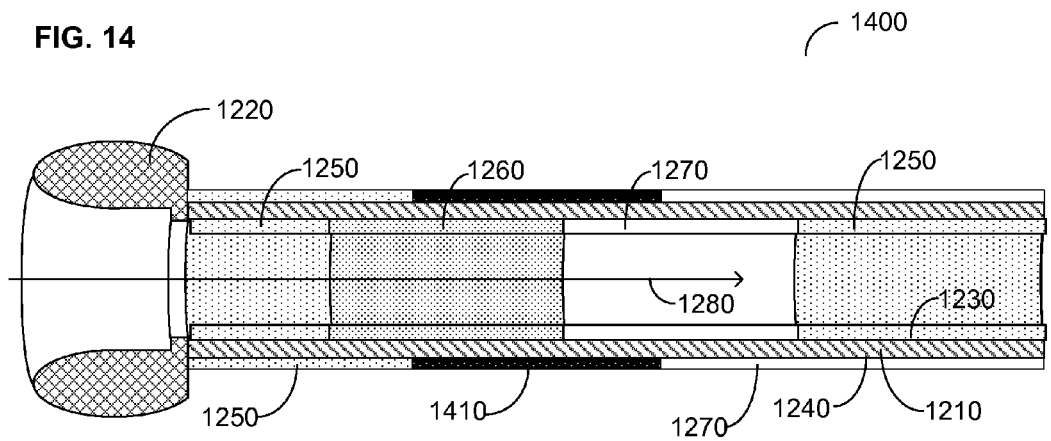
FIG. 14 is a schematic of a cross-section through a gastrointestinal device including multiple types of microbes on an inner surface and outer surface.

FIGS. 12-14 illustrate further aspects of a gastrointestinal device. In an aspect, the plurality of at least one type of commensal microbe associated with at least one of the inner surface and the outer surface of the flexible tubular structure includes one type of commensal microbe uniformly distributed along at least a portion of at least one of the inner surface and the outer surface of the flexible tubular structure. In an aspect, the plurality of at least one type of commensal microbe associated with at least one of the inner surface and the outer surface of the flexible tubular structure includes two or more types of commensal microbes uniformly distributed along at least a portion of at least one of the inner surface and the outer surface of the flexible tubular structure. For example, the flexible tubular structure can include a coating that includes a mixture of two or more types of commensal microbes. Alternatively, different portions of the flexible tubular structure can include different types or different proportions of commensal microbes. In an aspect, the flexible tubular structure includes a plurality of at least one first type of commensal microbe on at least one first portion of the flexible tubular structure and a plurality of at least one second type of commensal microbe on at least one second portion of the flexible tubular structure. In an aspect, the plurality of the at least one type of commensal microbe includes at least one first type of commensal microbe on at least one first portion of the flexible tubular structure and at least one second type of commensal microbe on at least one second portion of the flexible tubular structure.

In an aspect, at least a portion of the inner surface of a flexible tubular structure associated with a gastrointestinal device is lined with two or more types of commensal microbes. FIG. 12 shows a longitudinal cross-section through gastrointestinal device 1200. Gastrointestinal device 1200 includes flexible tubular structure 1210 (diagonal pattern) and anchor structure 1220. In this non-limiting example, anchor structure 1220 is inflatable, expanding radially to engage the wall of the gastrointestinal tract. Flexible tubular structure 1210 includes an inner surface 1230 and an outer surface 1240. The flexible tubular structure 1210 includes a plurality of two or more types of commensal microbes on inner surface 1230. Flexible tubular structure 1210 includes a plurality of at least one first type of commensal microbe 1250 on a first portion of the inner surface 1230, a plurality of at least one second type of commensal microbe 1260 on a second portion of the inner surface 1230, at least one third type of commensal microbe 1270 on a third portion of the inner surface 1230, and a plurality of the at least one first type of commensal microbe 1250 on a fourth portion of the inner surface 1230. The proximal and distal ends of flexible tubular structure 1210 form flow conduit 1280 (arrow) through the flexible tubular structure 1210.

In an aspect, at least a portion of the outer surface of a flexible tubular structure associated with a gastrointestinal device is covered with two or more types of commensal microbe. FIG. 13 shows a longitudinal cross-section through gastrointestinal device 1300. Gastrointestinal device 1300 includes flexible tubular structure 1210 (diagonal pattern) and anchor structure 1220. Flexible tubular structure 1210 includes an inner surface 1230 and an outer surface 1240. The flexible tubular structure 1210 includes a plurality of two of more types of commensal microbes on outer surface 1240. Flexible tubular structure 1210 includes a plurality of at least one first type of commensal microbe 1250 on a first portion of the outer surface 1240, a plurality of at least one second type of commensal microbe 1260 on a second portion of the outer surface 1240, and a plurality of at least one third type of commensal microbe 1270 on a third portion of the outer surface 1240. The proximal and distal ends of flexible tubular structure 1210 form flow conduit 1280 through the flexible tubular structure 1210.

In an aspect, at least a portion of the inner surface and at least a portion of the outer surface of a flexible tubular structure associated with a gastrointestinal device is covered with two or more types of commensal microbes. FIG. 14 shows a longitudinal cross-section through gastrointestinal device 1400. Gastrointestinal device 1400 includes flexible tubular structure 1210 (diagonal pattern) and anchor structure 1220. Flexible tubular structure 1210 includes an inner surface 1230 and an outer surface 1240. The flexible tubular structure 1210 includes a plurality of two or more types of commensal microbes on inner surface 1230 and outer surface 1240. Flexible tubular structure 1400 includes a plurality of at least one first type of commensal microbe 1250 on a first portion of the inner surface 1230, a plurality of at least one second type of commensal microbe 1260 on a second portion of the inner surface 1230, a plurality of at least one third type of commensal microbe 1270 on a third portion of the inner surface 1230, a second plurality of the at least one first type of commensal microbe 1250 on a fourth portion of the inner surface 1230, a third plurality of the at least one first type of commensal microbe 1250 on a first portion of the outer surface 1240, a plurality of the at least one second type of commensal microbe 1270 on a second portion of the outer surface 1240, and a plurality of at least one fourth type of commensal microbe 1410 on a third portion of the outer surface 1240.

In an aspect, the plurality of the at least one type of commensal microbe forms a gradient on the at least a portion of the at least one of the inner surface and the outer surface of the flexible tubular structure. For example, the plurality of the at least one type of commensal microbe can be distributed in a gradient along the length of at least a portion of the inner surface and/or the outer surface of the flexible tubular structure. For example, the concentration of the at least one type of commensal microbe can be greater at the proximal end of the flexible tubular structure than at the distal end of the flexible tubular structure. For example, the concentration of the at least one type of commensal microbe can be greater at the distal end of the flexible tubular structure than at the proximal end of the flexible tubular structure.

In an aspect, the plurality of the at least one first type of commensal microbe and the at least one second type of commensal microbe form a gradient on the flexible tubular structure. For example, the plurality of the at least one first type of commensal microbe forms a gradient from the proximal end to the distal end of the flexible tubular structure while the plurality of the at least one second type of commensal microbe forms a gradient from the distal end to the proximal end of the flexible tubular structure.

In an aspect, different combinations and/or concentrations of commensal microbes can be incorporated at different positions along the length of the flexible tubular structure to allow for temporal and spatial interaction between the commensal microbes and ingested products flowing through the device. In an aspect, different combinations and/or concentrations of commensal microbes can be incorporated at different positions along the length of the flexible tubular structure to allow for temporal and spatial interaction between the commensal microbes and components of the gastrointestinal wall.

Controllable Valve

In an aspect, the gastrointestinal device further includes at least one controllable valve. In an aspect, the at least one controllable valve controls flow of at least a portion of the gastrointestinal contents into the proximal end of the gastrointestinal device. In an aspect, the at least one controllable valve controls flow of at least a portion of the gastrointestinal contents out of the distal end of the gastrointestinal device. In an aspect, the at least one controllable valve prevents gastric reflexing. In an aspect, the at least one controllable valve is attached to the proximal and/or distal end of the flexible tubular structure. In an aspect, the at least one controllable valve is attached to and/or incorporated into the at least one anchor structure. See, e.g., U.S. Pat. No. 7,037,344 to Kagan et al. titled "Apparatus and Methods for Treatment of Morbid Obesity," which is incorporated herein by reference. For example, the controllable valve can include a toroidal structure made from a swellable material, e.g., a hydrogel.

Prebiotic Agents

In an aspect, the gastrointestinal device further includes at least one prebiotic agent. In an aspect, the at least one prebiotic agent promotes growth and/or maintenance of the at least one type of commensal microbe associated with the flexible tubular structure of the gastrointestinal device. In an aspect, the at least one prebiotic agents promotes growth and/or maintenance of microbes, e.g., bacteria, resident in the gastrointestinal tract. For example, the at least one type of prebiotic agent can include dietary fiber (e.g., polysaccharides and oligosaccharides) that promotes the growth of at least one type of commensal microbe, e.g., a probiotic, enhancing the beneficial effect of the at least one type of commensal microbe. For example, the at least one prebiotic agent can induce endogenous or administered microbes to generate short chain fatty acids (SCFAs). For example, the at least one prebiotic agent can induce endogenous or administered microbes to excrete an end product inhibitory to pathogenic bacteria. For example, the at least one prebiotic agent can promote a host-mediated attack against tumor sites and/or promote certain strains of *Lactobacillus* that have immune-modulating activity, enhancing phagocyte activity in the blood. For example, the at least one prebiotic agent may also affect the production of certain bacterial enzymes, such as decreasing glucosidase that is associated with the absorption of intestinal cholesterol. See, e.g., U.S. Pat. No. 7,101,565 to Monte titled "Probiotic/Prebiotic Composition and Delivery Method," which is incorporated herein by reference.

In an aspect, the at least one prebiotic agent is complimentary to the at least one type of commensal microbe associated with the flexible tubular structure. In an aspect, the at least one prebiotic agent is incorporated into the flexible tubular structure, e.g., formulated with the plurality of the at least one type of commensal microbe. In an aspect, the at least one prebiotic agent is administered separately, e.g., as an oral supplement.

In an aspect, the at least one prebiotic agent includes at least one of a mucopolysaccharide, a chitin, a carrageenan, arabinogalactin, a starch polysaccharide, an oligosaccharide, a fructo-oligosaccharide, or inulin. In an aspect, the at least one prebiotic agent includes one or more of an oligosaccharide, a fructo-oligosaccharide (e.g., soy fructo-oligosaccharide, inulin or banana fiber), a pectin or pectic polysaccharide, a mannan (e.g., guar gum, locust bean gum, konjac, or xanthan gum), a pentosan, beta-glucan, arabinan and galactan, such as larch arabinogalactan, and/or mixtures thereof. For example, the at least one prebiotic agent can include a long-chain polysaccharide comprised primarily of fructose monosaccharides (e.g., soy fructo-oligosaccharide, inulin or banana fiber), non-limiting sources of which include honey, beer, onion, asparagus, maple sugar, oats, and Jerusalem artichoke. For example, the at least one prebiotic agent can include pectin and/or pectic polysaccharides including galacturonans or rhamnogalacturonans having various side chains (e.g., D-galactose, L-arabinose, D-xylose, and, less frequently, L-frucose and D-glucuronic acid). For example, the at least one prebiotic agent can include a polysaccharides including neutral pectic polymers such as galactans and arabinans, xyloglucans, and galactomannans. In an aspect, the at least one prebiotic agent includes a form a non-starch polysaccharide, e.g., an arabingalactans. Additional non-limiting examples of prebiotic agents are described in U.S. Pat. No. 7,101,565 to Monte titled "Probiotic/Prebiotic Composition and Delivery Method," which is incorporated herein by reference.

In an aspect, the at least one prebiotic agent includes at least one of a protein, a peptide, a lipid, a nutrient, a vitamin, a mineral, or a salt. For example, the at least one prebiotic agent can include a buffering agent to alter a pH of the gastrointestinal tract. For example, the flexible tubular structure may include a buffer to neutralize the low pH of the chyme coming from the stomach, e.g., to replace or supplement a neutralizing function that is normally carried out by the bile. For example, the flexible tubular structure may include a buffer to alter a pH condition of the gastrointestinal tract to promote growth of commensal bacteria and/or to inhibit growth of pathogenic bacteria.

Other Agents

In an aspect, the gastrointestinal device further includes at least one therapeutic agent. In an aspect, the at least one therapeutic agent includes at least one agent of benefit to a gastrointestinal condition. For example, the at least one therapeutic agent can include at least one agent to treat an infection (e.g., bacterial infection), inflammation (e.g., inflammatory bowel disorder), ulcerative colitis, cancer, food sensitivity, muscle contraction, pain, or other condition of the gastrointestinal tract. In an aspect, the at least one therapeutic agent includes at least one antimicrobial agent (e.g., antibiotic, antifungal, antiparasitic, or antiviral agent), anti-inflammatory agent, or chemotherapy agent. In an aspect, the at least one therapeutic agent includes at least one muscle relaxant or anti-spasmodic. In an aspect, the at least one therapeutic agent includes at least one analgesic.

In an aspect, the gastrointestinal device further includes at least one bioactive agent. For example, the at least one bioactive agent can include at least one digestive enzyme or hormone for breaking down ingested products. Non-limiting examples of digestive enzymes and hormones include pepsin, trypsinogen, chymotrypsinogen, carboxypeptidase, pancreatic lipase, sterol esterase, phospholipase, nucleases, sucrose, lactase, maltase, gastrin, somatostatin, secretin, or cholecystokinin.

In an aspect, the at least one prebiotic agent, therapeutic agent, or bioactive agent is in a coating associated with at least a portion of at least one of the inner surface and the outer surface of the flexible tubular structure. In an aspect, the at least one prebiotic agent, therapeutic agent, or bioactive agent is in a degradable coating. In an aspect, the at least one prebiotic agent, therapeutic agent, or bioactive agent is in a degradable matrix. In an aspect, the degradable coating or matrix includes a stimulus-responsive degradable coating or matrix, non-limiting examples of which have been described above herein.

In an aspect, at least one first prebiotic agent, therapeutic agent, and/or bioactive agent is in a first degradable coating and at least one second prebiotic agent, therapeutic agent, and/or bioactive agent is in a second degradable coating. In an aspect, the first degradable coating and the second degradable coating degrade at different rates. For example, a gastrointestinal device may include a first degradable coating including at least one first prebiotic agent, therapeutic agent, and/or bioactive agent that degrades more rapidly than a second degradable coating including at least one second prebiotic agent, therapeutic agent, and/or bioactive agent, releasing the at least one first prebiotic agent, therapeutic agent, and/or bioactive agent more rapidly into the system than the at least one second prebiotic agent, therapeutic agent, and/or bioactive agent.

In an aspect, the plurality of the at least one type of commensal microbe is in a first degradable coating or matrix and at least one of a prebiotic agent, a therapeutic agent, or a bioactive agents is in a second degradable coating or matrix. In an aspect, the first degradable coating or matrix and the second degradable coating or matrix degrade at different rates. Non-limiting examples of degradable coatings and/or matrices have been described above herein.

In an aspect, the gastrointestinal device further includes at least one therapeutic apparatus. In an aspect, the gastrointestinal device further includes at least one therapeutic apparatus for delivering or activating an agent, e.g., a drug. In an aspect, the gastrointestinal device further includes at least one therapeutic apparatus for treating a tissue. In an aspect, the gastrointestinal device further includes at least one of an electronic apparatus, a photogenic apparatus, a magnetic apparatus, an acoustic apparatus.

Gastrointestinal Device with a Layered Wall Encasing a Plurality of at Least One Type of Commensal Microbe A gastrointestinal device is described that includes a flexible tubular structure including a layered wall, the flexible tubular structure including a plurality of at least one type of commensal microbe encased in the layered wall, the layered wall configured to allow an interaction between the plurality of the at least one type of commensal microbe and an ingested product within the flexible tubular structure; and a proximal and a distal end, the proximal end and the distal end forming a flow conduit through the flexible tubular structure; and at least one anchor structure including one or more gastric wall-engaging components configured to engage a wall of the gastrointestinal tract of a subject.

Figure 15:
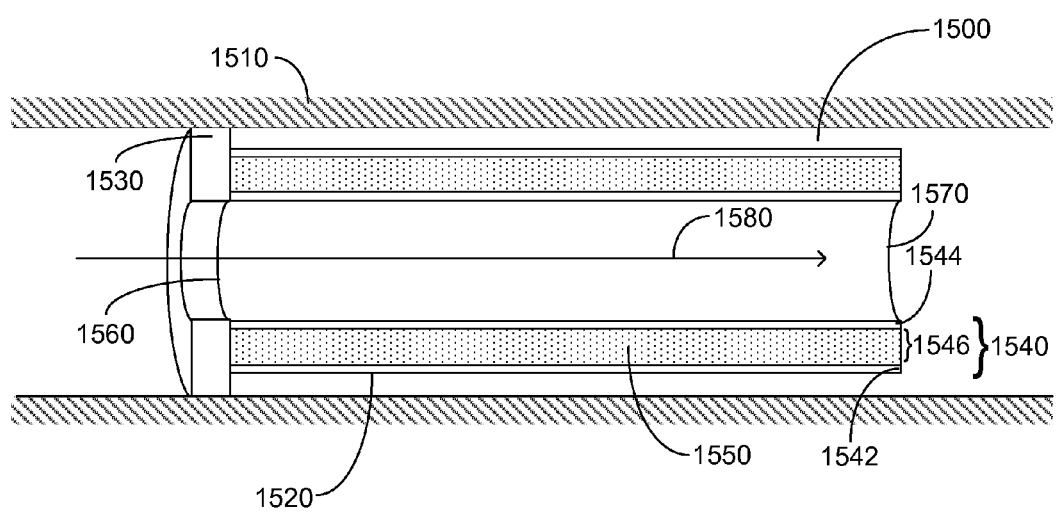
FIG. 15 is a schematic of a cross-section through a gastrointestinal device including a layered wall encasing a plurality of at least one type of commensal microbe.

With reference to FIG. 15, shown is an embodiment of a gastrointestinal device including a flexible tubular structure, a layered wall, and at least one anchor structure. FIG. 15 shows a longitudinal cross-section through gastrointestinal device 1500 positioned in the gastrointestinal tract 1510 of a subject. Gastrointestinal device 1500 includes flexible tubular structure 1520 and at least one anchor structure 1530. Flexible tubular structure 1520 includes layered wall 1540. Flexible tubular structure 1520 further includes a plurality of at least one type of commensal microbe 1550 encased in layered wall 1540. Flexible tubular structure 1520 further includes a proximal end 1560 and a distal end 1570 forming a flow conduit 1580 through the flexible tubular structure 1520. Gastrointestinal device 1500 further includes an anchor structure 1530 including one or more gastric wall-engaging components configured to engage a wall of the gastrointestinal tract 1510 of a subject.

In an aspect, the layered wall 1540 of flexible tubular structure 1520 includes an outer layer 1542, an inner layer 1544, and an internal space 1546. Outer layer 1542 is proximal to the wall of the gastrointestinal tract 1510. Inner layer 1544 is proximal to the flow conduit 1580 through the flexible tubular structure 1520. Internal space 1546 is positioned between the outer layer 1542 and the inner layer 1544 and includes the plurality of the at least one type of commensal microbe 1550.

The layered wall 1540 of gastrointestinal device 1500 is configured to allow an interaction between the plurality of the at least one type of commensal microbe and an ingested product within the flexible tubular structure. For example, the layered wall is configured to allow components of the food or chyme flowing through the flexible tubular structure to come in contact with the plurality of the at least one type of commensal microbe encased or entrapped in the layered wall. For example, the layered wall is configured to allow components secreted by the at least one type of commensal microbe to interact with an ingested product, e.g., one or more components of the food or chyme.

In an aspect, gastrointestinal device 1500 is configured to allow an interaction between the plurality of the at least one type of commensal microbe and components of the gastrointestinal wall. For example, products secreted from the at least one type of commensal microbe encased in the layered wall can interact with the mucosal or cells layers of the gastrointestinal tract.

In an aspect, gastrointestinal device 1500 including flexible tubular structure 1520 and at least one anchor structure 1530 is sized for placement in a portion of the gastrointestinal tract. In an aspect, at least a portion of gastrointestinal device 1500 is sized for placement in a mouth, esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof.

In an aspect, flexible tubular structure 1520 is a sleeve, a liner, or a stent. In an aspect, flexible tubular structure 1520 is sized for placement in a mouth, esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof. Non-limiting examples of dimensions for a flexible tubular structure, for example, have been described above here.

In an aspect, flexible tubular structure 1520 is of a type to treat a medical condition of the subject. In an aspect, the medical condition of the subject includes at least one of diabetes, obesity, metabolic syndrome, colitis, cancer, inflammatory bowel disease, irritable bowel syndrome, an autoimmune disorder, trauma, stricture, microbial infection, or microbial deficit.

In an aspect, at least one of the outer layer and the inner layer is formed from a semi-permeable material. In an aspect, the semi-permeable material is selectively permeable. In an aspect, the semi-permeable material is selectively permeable based on at least one of size, hydrophobicity, or charge. In an aspect, the semi-permeable material includes a plurality of pores. In an aspect, the outer layer or the inner layer is formed from a substantially impermeable material. Non-limiting examples of semi-permeable and substantially impermeable materials have been described above herein.

In an aspect, the layered wall of the flexible tubular structure of the gastrointestinal device includes an attachment mechanism for holding the outer layer and the inner layer together. In an aspect, the attachment mechanism includes a material, e.g., an adhesive, adherent, gel, or matrix, in the internal space that holds the outer layer and the inner layer together. For example, the internal space including the plurality of the at least one type of commensal microbe can include a material, e.g., an adhesive, adherent, gel, or matrix, to which the outer layer and the inner layer adhere. In an aspect, the attachment mechanism includes one or more staples, stitches, pins, or like mechanism for holding the outer layer and the inner layer together. For example, layered wall can include staples that hold the inner layer and the outer layer together. For example, the inner layer and the outer layer can be stitched together with a form of biocompatible thread, e.g., suture thread. In an aspect, the inner layer and the outer layer are fused together at specific points along the length of the flexible tubular structure in response to a stimulus, e.g., pressure, heat, or chemical stimulus. In an aspect, the attachment mechanism is degradable. For example, an adhesive may lose adhesive strength overtime. For example, the layered wall may include degradable staples or sutures. In an aspect, the inner layer and the outer layer are held together through the at least one anchor structure. For example, the inner layer and the outer layer of the layered wall of the flexible tubular structure can be separately attached to at least one anchor structure, e.g., at the proximal and/or distal ends of the flexible tubular structure.

Figure 16:
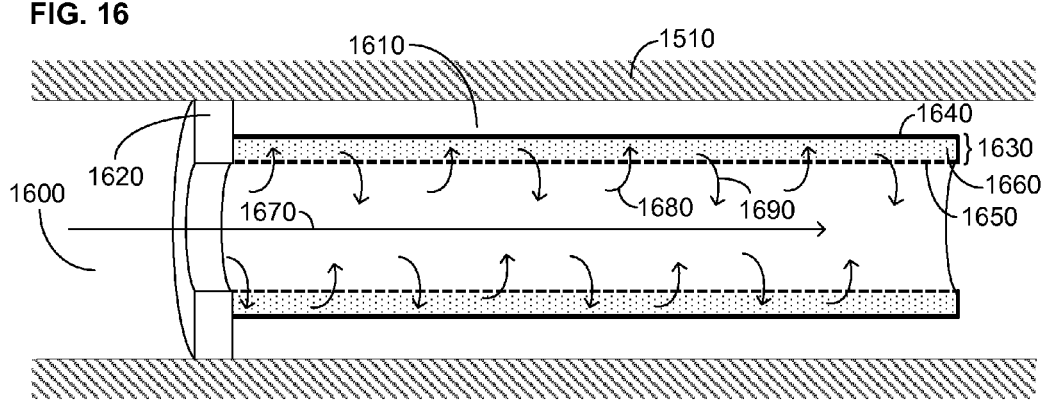
FIG. 16 is a schematic of a cross-section through a gastrointestinal device including a layered wall with an inner layer formed from a semi-permeable material.
Figure 17:
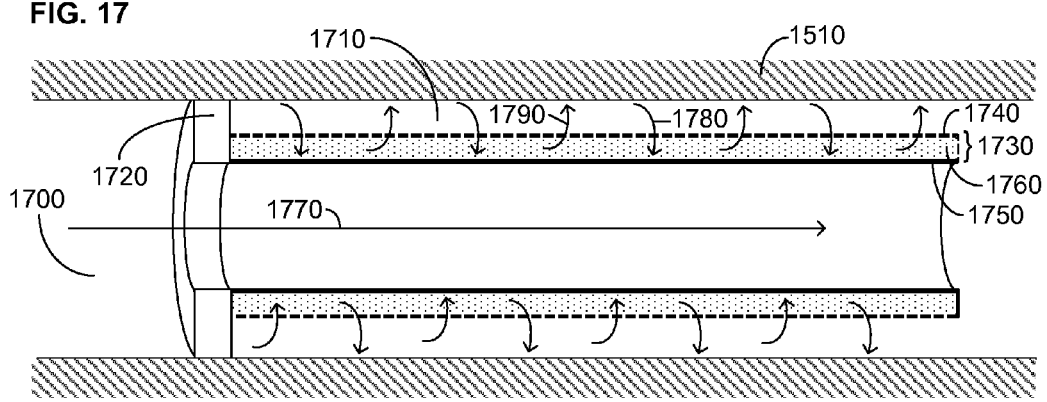
FIG. 17 is a schematic of a cross-section through a gastrointestinal device including a layered wall with an outer layer formed from a semi-permeable material.
Figure 18:
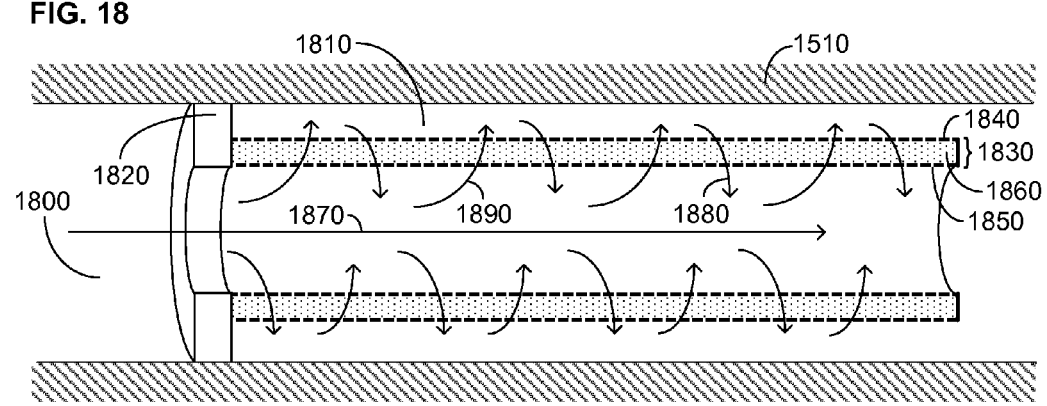
FIG. 18 is a schematic of a cross-section through a gastrointestinal device including a layered wall with an inner layer and an outer layer formed from a semi-permeable material.

FIGS. 16-18 show non-limiting embodiments of a gastrointestinal device including a flexible tubular structure with a layered wall. In an aspect, the layered wall of the flexible tubular structure includes an outer layer that is substantially impermeable and an inner layer that is at least semi-permeable, as illustrated in FIG. 16. FIG. 16 shows a cross-sectional view through gastrointestinal device 1600 positioned in the gastrointestinal tract 1510 of a subject. Gastrointestinal device 1600 includes flexible tubular structure 1610 and at least one anchor structure 1620. Flexible tubular structure 1610 includes a layered wall 1630. Layered wall 1630 includes an outer layer 1640 formed from a substantially impermeable material and an inner layer 1650 formed from a semi-permeable material. Layered wall 1630 further includes internal space 1660 including a plurality of at least one type of commensal microbe. Flexible tubular structure 1610 includes flow conduit 1670 through which ingested products are able to flow. Layered wall 1630 is configured to allow flow inward 1680 of ingested products through the semi-permeable inner layer 1650 but not through substantially impermeable outer layer 1640. Layered wall 1630 is further configured to allow flow outward 1690 from the internal space 1660 through the semi-permeable inner layer 1650.

In an aspect, the layered wall of the flexible tubular structure includes an outer layer that is at least semi-permeable and an inner layer that is substantially impermeable, as illustrated in FIG. 17. FIG. 17 shows a cross-sectional view through gastrointestinal device 1700 positioned in the gastrointestinal tract 1510 of a subject. Gastrointestinal device 1700 includes flexible tubular structure 1710 and at least one anchor structure 1720. Flexible tubular structure 1710 includes a layered wall 1730. Layered wall 1730 includes an outer layer 1740 formed from a semi-permeable material and an inner layer 1750 formed from a substantially impermeable material. Layered wall 1730 further includes internal space 1760 including a plurality of at least one type of commensal microbe. Flexible tubular structure 1710 includes flow conduit 1770 through which ingested products are able to flow. Layered wall 1730 is configured to allow flow inward 1780 of components from the gastrointestinal tract, e.g., digestive enzymes through the semi-permeable outer layer 1740. Layered wall 1730 is further configured to allow flow outward 1790 through outer layer 1740. In this configuration, the layered wall 1730 does not allow flow through the substantially impermeable inner layer to the flow conduit 1770.

In an aspect, the layered wall of the flexible tubular structure includes an outer layer that is semi-permeable and an inner layer that is semi-permeable, as illustrated in FIG. 18. FIG. 18 shows a cross-section through gastrointestinal device 1800 positioned in the gastrointestinal tract 1510 of a subject. Gastrointestinal device 1800 includes flexible tubular structure 1810 and at least one anchor structure 1820. Flexible tubular structure 1810 includes a layered wall 1830. Layered wall 1830 includes an outer layer 1840 formed from a semi-permeable material and an inner layer 1850 formed from a semi-permeable material. Layered wall 1830 further includes internal space 1860 including a plurality of at least one type of commensal microbe. Flexible tubular structure 1810 includes flow conduit 1870 through which ingested products are able to flow. Layered wall 1830 is configured to allow flow inward 1880 of components from the gastrointestinal tract, e.g., digestive enzymes through the semi-permeable outer layer 1840, the internal layer 1860, the inner layer 1850, and into the flow conduit 1870 of the flexible tubular structure 1810. Layered wall 1830 is further configured to allow flow outward 1880 from the flow conduit 1870 of the flexible tubular structure 1810, through inner layer 1850, internal space 1860, and outer layer 1840 to the wall region of the gastrointestinal tract 1510.

In an aspect, the layered wall of the flexible tubular structure includes an outer layer and an inner layer. In an aspect, the outer layer is formed from a first semi-permeable material and the inner layer is formed from a second semi-permeable material. In an aspect, the first semi-permeable material and the second semi-permeable material are the same semi-permeable material. In an aspect, the first semi-permeable material and the second semi-permeable material are different semi-permeable materials. In an aspect, the first semi-permeable material and the second semi-permeable material are selectively permeable. In an aspect, the at least one of the first semi-permeable material and the second semi-permeable material is selectively permeable based on at least one of size, hydrophobicity, or charge. For example, the first semi-permeable material may have a first size exclusion, e.g., 100,000 mw, and the second semi-permeable material may have a second size exclusion, e.g., 10,000 mw, allowing large ingested products to pass into the semi-permeable wall but only smaller ingest products to exit out the other side. In an aspect, at least one of the first semi-permeable material and the second semi-permeable material includes a plurality of pores. Non limiting examples of semi-permeable and substantially impermeable material have been described above herein.

In an aspect, the layered wall of the flexible tubular structure includes an internal space including the plurality of the at least one type of commensal microbe. In an aspect, the internal space including the plurality of the at least one type of commensal microbe includes a permeable material. In an aspect, the permeable material includes at least one of a mucus material, a gel material, a porous material, or a fibrous material.

In an aspect, at least a portion of the flexible tubular structure is degradable. In an aspect, at least a portion of the layered wall is degradable. For example, at least one of the inner layer, outer layer, and internal space can be formed from a degradable material configured to degrade over time. For example, at least one of the inner layer, outer layer, and internal space can be formed from a degradable material that degrades over time in response to temperature, moisture, pH, or a chemical. In an aspect, the flexible tubular structure is noncontiguous. For example, the flexible tubular structure can include two or more segments attached to one another through a degradable linker that degrades over time to release the two or more segments.

Gastrointestinal device 1500 includes a plurality of at least one type of commensal microbe encased in the layered wall of the flexible tubular structure. In an aspect, the plurality of the at least one type of commensal microbe includes at least one type of commensal gut microbe. For example, the at least one type of commensal gut microbe encased in the layered wall can include at least one type of Firmicutes or Bacteroidetes. In an aspect, the plurality of the at least one type of commensal microbe includes at least one type of genetically modified microbe. For example, the at least one type of genetically modified microbe encased in the layered wall can include at least one type of microbe genetically modified to express a digestive enzyme or therapeutic agent.

In an aspect, the plurality of the at least one type of commensal microbe includes at least one type of commensal microbe from a fecal sample. For example, at least one type of commensal microbe from a fecal sample can be encased in the layered wall of the gastrointestinal device. In an aspect, the at least one type of commensal microbe from the fecal sample includes at least one type of commensal microbe from a fecal sample from at least the subject or one or more other individuals. In an aspect, the at least one type of commensal microbe from the fecal sample from one or more other individuals includes at least one type of commensal microbe from a fecal sample from at least one of a relative of the subject, a healthy donor, or a preferred donor.

In an aspect, the plurality of the at least one type of commensal microbe includes at least part of a gut microbiota. For example, at least part of a gut microbiota can be encased in the layered wall of the gastrointestinal device. In an aspect, the at least part of the gut microbiota includes at least part of a gut microbiota of the subject. In an aspect, the at least part of the gut microbiota includes at least part of a gut microbiota of at least one other individual. In an aspect, the at least part of the gut microbiota includes at least part of a health microbiota, a preferred microbiota, or a theoretical microbiota. In an aspect, the at least part of the gut microbiota is derived from a fecal sample. In an aspect, the at least part of the gut microbiota is derived from in vitro culture of one or more types of commensal gut microbes.

In an aspect, the plurality of the at least one type of commensal microbe forms a microbiome. For example, the at least one type of commensal microbe can contribute directly or indirectly to the ecological community of the gastrointestinal tract.

In an aspect, a gastrointestinal device with the at least one type of commensal microbe is beneficial to a subject having a medical condition. In an aspect, the medical condition of the subject includes at least one of diabetes, obesity, metabolic syndrome, colitis, cancer, inflammatory bowel disease, irritable bowel syndrome, an autoimmune disorder, or a microbial infection. In an aspect, the medical condition includes a *Clostridium difficile* infection. In an aspect, the medical condition includes Crohn's disease. In an aspect, the medical condition includes ischemia in a portion of the gastrointestinal tract. In an aspect, the medical condition includes a stricture (e.g., in a patient with Crohn's disease). In an aspect, the medical condition includes an obstruction (e.g., a benign or malignant growth). In an aspect, the medical condition includes an irritation or damage to a portion of the gastrointestinal tract. In an aspect, the medical condition includes trauma to a portion of the gastrointestinal tract, for example trauma from injury or due to surgery (e.g., excision of tissue or recision of a portion of the gastrointestinal tract).

In an aspect, the at least one type of commensal microbe associated with the gastrointestinal device is beneficial to a medical condition of the subject. In an aspect, the at least one type of commensal microbe is beneficial to the immune system of the subject. In an aspect, the at least one type of commensal microbe is beneficial to a dietary condition of the subject. In an aspect, the dietary condition of the subject includes a dietary need of the subject (e.g., a nutritional need), weight control of the subject (e.g., obesity), or a food sensitivity of the subject (e.g., a gluten sensitivity or inability to digest lactose).

In an aspect, the plurality of the at least one type of commensal microbe includes at least one type of probiotic. Non-limiting examples of probiotics have been described above herein.

In an aspect, the plurality of the at least one type of commensal microbe includes at least one type of *Bifidobacterium*. In an aspect, the at least one type of *Bifidobacterium* includes at least one type of *B. adolescentis*. In an aspect, the plurality of the at least one type of commensal microbe includes at least one type of *Bacteroides*. In an aspect, the plurality of the at least one type of commensal microbe includes at least one type of *Lactobacillus*. In an aspect, the at least one type of *Lactobacillus* includes one or more of *L. acidophilus, L. casei, L. fermentum, L. salivaroes, L. brevis, L. leichmannii, L. plantarum*, or *L. cellobiosius*.

In an aspect, the internal space including the plurality of the at least one type of commensal microbe includes a permeable material. For example, the internal space of the layered wall of the gastrointestinal device can include a material that allows for free flow of fluid and materials through the internal space within the confines of the outer layer and inner layer of the layered wall. In an aspect, the plurality of the at least one type of commensal microbe is associated with at least one of a porous material, a fibrous material, a mucus material, or a gel material in the layered wall. In an aspect, the plurality of the at least one type of commensal microbe is immobilized in the layered wall. For example, the plurality of at least one type of commensal microbe can adhere to materials (e.g., fibers) or pores associated with an internal space of the layered wall. For example, the at least one type of commensal microbe can line an exposed surface of a pore, allowing for interaction between the at least one type of commensal microbe and an ingested product. In an aspect, the plurality of the at least one type of commensal microbe is diffusible from the layered wall. For example, at least one of the inner layer or the outer layer can be formed from a material sufficiently porous enough to allow passage of the at least one type of commensal microbe.

FIG. 19 illustrates further aspects of a gastrointestinal device including a layered wall. In an aspect, the plurality of the at least one type of commensal microbe includes a plurality of at least one first type of commensal microbe in a first portion of the layered wall and a plurality of at least one second type of commensal microbe in a second portion of the layered wall. FIG. 19 shows a cross-section through gastrointestinal device 1900 positioned in gastrointestinal tract 1510 of a subject. Gastrointestinal device 1900 includes a flexible tubular structure 1910 and at least one anchor structure 1920. Flexible tubular structure 1910 includes layered wall 1930 and flow conduit 1960. Flexible tubular structure 1910 further includes a plurality of at least one first type of microbe 1940 in a first portion of the layered wall 1930 and a plurality of at least one second type of microbe 1950 in a second portion of the layered wall.

FIG. 20 illustrates further aspects of a gastrointestinal device including a layered wall. In an aspect, the plurality of the at least one type of commensal microbe forms a gradient within the layered wall. FIG. 20 shows a cross-section through gastrointestinal device 2000 positioned in gastrointestinal tract 1510 of a subject. Gastrointestinal device 2000 includes a flexible tubular structure 2010 and at least one anchor structure 2020. Flexible tubular structure 2010 includes layered wall 2030 and flow conduit 2080. Flexible tubular structure further includes a first concentration 2040 of a plurality of at least one type of commensal microbe in a first position of layered wall 2030, a second concentration 2050 of the plurality of the at least one type of commensal microbe in a second position of layered wall 2030, a third concentration 2060 of the plurality of the at least one type of commensal microbe at a third position of layered wall 2030, and a fourth concentration 2070 of the plurality of the at least one type of commensal microbe in a fourth position of layered wall 2030.

In an aspect, gastrointestinal device 1500 further includes at least one prebiotic agent. In an aspect, the at least one prebiotic agent includes at least one of a mucopolysaccharide, a chitin, a carrageenan, arabinogalactan, a starch polysaccharide, an oligosaccharide, a fructo-oligosaccharide, or inulin. In an aspect, the at least one prebiotic agent includes at least one of a protein, a peptide, a lipid, a nutrient, a vitamin, a mineral, or a salt. Non-limiting examples of other prebiotic agents have been described above therein. In an aspect, the at least one prebiotic agent is associated with the outer layer and/or the inner layer of the layered wall of the flexible tubular structure. In an aspect, the at least one prebiotic agent is associated with the internal space of the layered wall of the flexible tubular structure. In an aspect, the at least one prebiotic agent is associated with the at least one anchor structure. In an aspect, the at least one prebiotic agent is included in a degradable coating or matrix associated with outer layer and/or the inner layer of the flexible tubular structure. In an aspect, the at least one prebiotic agent is included in a degradable coating or matrix associated with the internal space of the layered wall of the flexible tubular structure. In an aspect, the at least one prebiotic agent is included in a degradable coating or matrix associated with the at least one anchor structure.

In an aspect, gastrointestinal device 1500 further includes at least one therapeutic agent. For example, the gastrointestinal device can include at least one antibiotic. In an aspect, gastrointestinal device 1500 includes at least one bioactive agent. For example, the gastrointestinal device can include at least one digestive enzyme. Other non-limiting examples of therapeutic agents and bioactive agents have been described above herein. In an aspect, the at least one therapeutic agent and/or the at least one bioactive agent is associated with the outer layer and/or the inner layer of the layered wall of the flexible tubular structure. In an aspect, the at least one therapeutic agent and/or the at least one bioactive agent is associated with the internal space of the layered wall of the flexible tubular structure. In an aspect, the at least one therapeutic agent and/or the at least one bioactive agent is associated with the at least one anchor structure. In an aspect, the at least one therapeutic agent and/or the at least one bioactive agent is included in a degradable coating or matrix associated with outer layer and/or the inner layer of the flexible tubular structure. In an aspect, the at least one therapeutic agent and/or the at least one bioactive agent is included in a degradable coating or matrix associated with the internal space of the layered wall of the flexible tubular structure.

Gastrointestinal device 1500 includes at least one anchor structure including one or more gastric wall-engaging components configured to engage a wall of the gastrointestinal tract of a subject. In an aspect, the at least one anchor structure is attached to the proximal end of the flexible tubular structure. In an aspect, the at least one anchor structure is attached to the distal end of the flexible tubular structure. In an aspect, the at least one anchor structure is incorporated into the flexible tubular structure. In an aspect, the at least one anchor structure includes one or more gastric wall-engaging components positioned along at least a portion of the flexible tubular structure. In an aspect, the one or more gastric wall-engaging components include one or more barbs or one or more hooks. In an aspect, the one or more gastric wall-engaging components include an adhesive or an adherent. In an aspect, the at least one anchor structure is inflatable. In an aspect, the at least one anchor structure is expandable. Non-limiting examples of anchor structures have been described above herein.

Gastrointestinal Device Including at Least One Microbe-Promoting Agent

An embodiment of a gastrointestinal device is described herein including a flexible tubular structure including an inner surface and an outer surface, at least one microbe-promoting agent associated with at least one of the inner surface and the outer surface, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more gastric wall-engaging components configured to engage a wall of the gastrointestinal tract of a subject.

In an aspect, the gastrointestinal device including the at least one microbe-promoting agent is sized for placement in a portion of the gastrointestinal tract of the subject. In an aspect, the gastrointestinal device including the at least one microbe-promoting agent is sized for placement in a mouth, esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof. In an aspect, the flexible tubular structure associated with the gastrointestinal device including the at least one microbe-promoting agent is sized for placement in a portion of the gastrointestinal tract of the subject. In an aspect, the flexible tubular structure is sized for placement in a mouth, esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof.

In an aspect, the flexible tubular structure is of a type configured to treat a medical condition of the subject. In an aspect, the flexible tubular structure including at least one microbe-promoting agent is configured to treat a medical condition of the subject. In an aspect, the flexible tubular structure including at least one microbe-promoting agent is configured to treat at least one of diabetes, obesity, metabolic syndrome, colitis, cancer, inflammatory bowel disease, irritable bowel syndrome, an autoimmune disorder, or a microbial infection. In an aspect, the medical condition includes a *Clostridium difficile* infection. In an aspect, the medical condition includes Crohn's disease. In an aspect, the medical condition includes ischemia in a portion of the gastrointestinal tract. In an aspect, the medical condition includes a stricture (e.g., in a patient with Crohn's disease). In an aspect, the medical condition includes an obstruction (e.g., a benign or malignant growth). In an aspect, the medical condition includes an irritation or damage to a portion of the gastrointestinal tract. In an aspect, the medical condition includes trauma to a portion of the gastrointestinal tract, for example trauma from injury or due to surgery (e.g., excision of tissue or recision of a portion of the gastrointestinal tract).

FIGS. 21-23 illustrate aspects of a gastrointestinal device including at least one microbe-promoting agent associated with at least one of the inner surface and the outer surface of the flexible tubular structure. FIG. 21 shows a cross-section through gastrointestinal device 2100 positioned in gastrointestinal tract 2110 of a subject. Gastrointestinal device 2100 includes flexible tubular structure 2120 and at least one anchor structure 2130. Flexible tubular structure 2120 includes an inner surface 2140 and an outer surface 2150. Flexible tubular structure 2120 further includes at least one microbe-promoting agent 2160 (stippled pattern) associated with the outer surface 2150 of flexible tubular structure 2120. Flexible tubular structure 2120 of gastrointestinal device 2100 further includes a proximal end 2170 and a distal end 2180 forming a flow conduit 2190 through flexible tubular structure 2120.

FIG. 22 shows a cross-section through gastrointestinal device 2200 positioned in gastrointestinal tract 2110 of a subject. Gastrointestinal device 2200 includes a flexible tubular structure 2120 and at least one anchor structure 2130. Flexible tubular structure 2120 of gastrointestinal device 2200 includes at least one microbe-promoting agent 2210 (stippled pattern) associated with the inner surface 2140 of flexible tubular structure 2120. Flexible tubular structure 2120 of gastrointestinal device 2200 further includes a proximal end 2170 and a distal end 2180 forming a flow conduit 2190 through flexible tubular structure 2120.

FIG. 23 shows a cross-section through gastrointestinal device 2300 positioned in gastrointestinal tract 2110 of a subject. Gastrointestinal device 2300 includes flexible tubular structure 2120 and at least one anchor structure 2130. Flexible tubular structure 2120 of gastrointestinal device 2300 includes at least one microbe-promoting agent 2310 (stippled pattern) on the inner surface 2140 and the outer surface 2150 of the flexible tubular structure 2120. Flexible tubular structure 2120 of gastrointestinal device 2300 further includes a proximal end 2170 and a distal end 2180 forming a flow conduit 2190 through flexible tubular structure 2120.

In an aspect, flexible tubular structure 2120 is formed from a semi-permeable material. For example, the flexible tubular structure can be formed from a material that permits laterally transit of certain ingested products, e.g., water and vitamins, from the interior of the flexible tubular structure through to the gastrointestinal wall but prevents transit of other ingested products, e.g., carbohydrates and/or fats. In an aspect, the at least one microbe-promoting agent is associated with the inner surface of the semi-permeable material. In an aspect, the at least one microbe-promoting agent is associated with the outer surface of the semi-permeable material. In an aspect, the at least one microbe-promoting agent is associated with the inner surface and the outer surface of the semi-permeable material of the flexible tubular structure.

In an aspect, the semi-permeable material is selectively permeable. In an aspect, the semi-permeable material is selectively permeable based on size. In an aspect, the semi-permeable material is selectively permeable based on hydrophobicity. In an aspect, the semi-permeable material is selectively permeable based on charge. In an aspect, the semi-permeable material includes a plurality of pores. In an aspect, the semi-permeable material includes a fibrous material. Non-limiting examples of semi-permeable materials have been described above herein.

In an aspect, the flexible tubular structure 2120 is formed from a substantially impermeable material. For example, the flexible tubular structure can be formed from an impermeable material (e.g., an impermeable plastic) that prevents lateral transit of ingested products from the interior of the flexible tubular structure through to the gastrointestinal wall. In an aspect, the at least one microbe-promoting agent is associated with the inner surface of a flexible tubular structure formed from a substantially impermeable material. In an aspect, the at least one microbe-promoting agent is associated with the outer surface of a flexible tubular structure formed from a substantially impermeable material. In an aspect, the at least one microbe-promoting agent is associated with the inner surface and the outer surface of a flexible tubular structure formed from a substantially impermeable material. Non-limiting examples of substantially impermeable materials have been described above herein.

In an aspect, at least a portion of the flexible tubular structure is degradable. For example, the flexible tubular structure can be formed from a semi-permeable material that is degradable. For example, the flexible tubular structure can be formed from a substantially impermeable material that is degradable.

In an aspect, the flexible tubular structure is noncontiguous. For example, the flexible tubular structure may be formed from two or more segments. For example, the flexible tubular structure may be formed from two or more segment connected to one another through a degradable linkage.

A gastrointestinal device is described herein including at least one microbe-promoting agent configured to promote at least one of attraction, colonization, and growth of at least one type of commensal microbe. In an aspect, the at least one microbe-promoting agent is configured to promote at least one of attraction, colonization, and growth of at least one type of commensal gut microbe. In an aspect, the at least one microbe-promoting agent is configured to promote at least one of attraction, colonization, and growth of at least part of a gut microbiota. In an aspect, the at least one microbe-promoting agent is configured to promote at least one of attraction, colonization, and growth of at least one type of commensal microbe derived from a fecal sample. In an aspect, the at least one microbe-promoting agent is configured to promote at least one of attraction, colonization, and growth of at least one type of genetically engineered microbe. In an aspect, the at least one microbe-promoting agent is configured to promote at least one of attraction, colonization, and growth of at least one type of commensal microbe derived from in vitro culture. In an aspect, the at least one microbe-promoting agent is configured to promote at least one of attraction, colonization, and growth of at least one type of probiotic.

In an aspect, the at least one microbe-promoting agent is configured to promote at least one of attraction, colonization, and growth of at least one type of endogenous commensal microbe. For example, the at least one microbe-promoting agent can be configured to promote attraction, colonization, and/or growth of at least one type of commensal microbe resident in the gastrointestinal tract of the subject. In an aspect, the at least one microbe-promoting agent is configured to promote at least one of attraction, colonization, and growth of at least one type of administered commensal microbe. For example, the at least one microbe-promoting agent can be configured to promote attraction, colonization, and/or growth of an orally ingested commensal microbe, e.g., a commensal gut microbe, at least part of a gut microbiota, at least one type of commensal microbe from a fecal sample, a probiotic, a genetically engineered microbe, and/or a commensal microbe derived from in vitro culture. For example, the at least one microbe-promoting agent can be configured to promote attraction, colonization, and/or growth of an orally ingested commensal microbe administered in a dehydrated form (e.g., in powder, capsule, or pill form), liquid form, suspended form, or paste form.

In an aspect, the at least one microbe-promoting agent is configured to promote at least one of attraction, colonization, and growth of at least one type of commensal microbe beneficial to a subject. In an aspect, the at least one microbe-promoting agent is configured to promote at least one of attraction, colonization, and growth of at least one type of commensal microbe beneficial to a subject having a medical condition. In an aspect, the at least one microbe-promoting agent is configured to promote at least one of attraction, colonization, and growth of at least one type of commensal microbe beneficial to a subject having at least one of diabetes, obesity, metabolic syndrome, colitis, cancer, inflammatory bowel disease, irritable bowel syndrome, an autoimmune disorder, or a microbial infection. In an aspect, the at least one microbe-promoting agent is configured to promote at least one of attraction, colonization, and growth of at least one type of commensal microbe beneficial to the immune system of the subject. In an aspect, the at least one microbe-promoting agent is configured to promote at least one of attraction, colonization, and growth of at least one type of commensal microbe beneficial to a dietary condition of the subject. In an aspect, the dietary condition of the subject includes a dietary need of the subject (e.g., a nutritional need), weight control of the subject (e.g., obesity), or a food sensitivity of the subject (e.g., a gluten sensitivity or inability to digest lactose).

In an aspect, the at least one microbe-promoting agent is configured to promote formation of a microbiome. For example, the at least one microbe-promoting agent is configured to promote attraction, colonization, and growth of one or more types of microbes of the microbiome.

In an aspect, the at least one microbe-promoting agent includes at least one prebiotic agent. In an aspect, the at least one prebiotic agent includes at least one of a mucopolysaccharide, a chitin, a carrageenan, an arabinogalactin, a starch polysaccharide, an oligosaccharide, a fructo-oligosaccharide, or inulin. In an aspect, the at least one prebiotic agent includes at least one of a protein, a peptide, a lipid, a nutrient, a vitamin, a mineral, or a salt. Other non-limiting examples of prebiotic agents have been described above herein.

In an aspect, the at least one microbe-promoting agent includes at least one chemoattractant for attracting a microbe. In an aspect, the chemoattractant includes a ligand that interacts with microbial-chemoreceptors. For example, the chemoattractant can include sugars, e.g., D-maltose, D-ribose, or D-galactose. For example, the chemoattractant can include formyl peptides, e.g., di-, tri-, or tetrapeptides including a formyl group. See, e.g., Neumann et al (2010), *EMBO J.* 29:3484-3495, which is incorporated herein by reference. For example, the chemoattractant can include formyl peptides. For example, the chemoattractant can include chemokines. In an aspect, the at least one chemoattractant is in a coating. In an aspect, the at least one chemoattractant is in a degradable coating. For example, the at least one chemoattractant is slowly releasable from the degradable coating over time. For example at least two chemoattractants are releasable at different rates, e.g., chemoattractant that acts over longer distances is released first, and one that acts over shorter distances is subsequently released.

In an aspect, the at least one microbe-promoting agent includes a mucus. In an aspect, at least one of the inner surface and the outer surface of the flexible tubular structure includes a mucus layer to promote attraction, colonization, and growth of at least one type of commensal microbe. In an aspect, the mucus includes natural mucus. For example, the microbe-promoting agent can include components of natural mucus isolated from a mammalian gastrointestinal tract. In an aspect, the mucus includes synthetic mucus. For example, the microbe-promoting agent can include components of synthetic mucus, e.g., mucin glycoproteins. Other non-limiting examples of mucus and mucus components have been described above herein.

In an aspect, the at least one microbe-promoting agent includes one or more mucins, heavily glycosylated proteins naturally produced by epithelial tissues. In an aspect, the at least one microbe-promoting agent includes the gel-forming glycoprotein MUC2, the primary intestinal secreted mucin. In an aspect, the at least one microbe-promoting agent includes anti-bacterial proteins such as RegIIIγ, IgA, and IgM, constituents of mammalian mucus that inhibit pathogenic bacteria. In an aspect, the one or more mucins form an organized structure on at least one of the inner surface and the outer surface of the flexible tubular structure, the organized structure of mucins containing both a dense area and a loose layer, the loose layer amenable to infiltration by commensal bacteria. For example, probiotic *Lactobacillus* species are known to have mucus-binding proteins that facilitate association of *Lactobacillus* species with intestinal mucus. See, e.g., Van Tassell & Miller (2011) *Nutrition* 3:613-636, which is incorporated herein by reference. In an aspect, a probiotic species is provided to promote the expression and synthesis of mucins as part of a mucus layer. For example, addition of probiotic *Lactobacillus casei* can be used to up-regulate the expression of MUC2 in cultured intestinal cells. See, e.g., Mattar et al. (2002) *Pediatr. Surg. Int.* 18:586-590, which is incorporated herein by reference.

In an aspect, the mucus is produced by a monolayer of cells grown on at least one of the inner surface and the outer surface of the flexible tubular structure. In an aspect, at least one of the inner surface and the outer surface of the flexible tubular structure includes a type of epithelial cell. For example, the epithelial cells can include intestinal epithelial cells. For example, the epithelial cells can include primary epithelial cells, e.g., isolated from the subject. For example the epithelial cells can include cultured cells. Non-limiting examples of cultured intestinal epithelial cells are available from ATCC (American Type Culture Collection) Manassas, Va. In an aspect, the epithelial cells are derived from stem cells. For example, the epithelial cells can include stem cells, e.g., embryonic or mesenchymal stem cells. For example, various lineages of intestinal epithelial cells can be derived from crypt base columnar cells isolated from the bottom of intestinal crypts. See, e.g., Fujii & Sato (2014) *Frontiers in Genetics,* 5:169, which is incorporated herein by reference. For example, at least one of the inner surface and the outer surface of the flexible tubular structure can include a monolayer of intestinal submucosal cells.

In an aspect, the mucus layer further includes antiseptic enzymes, e.g., lysozyme, immunoglobulins, inorganic salts, and proteins, e.g., lactoferrin. In an aspect, the mucus layer is formed on a surface of the flexible tubular structure from a layer of mucus-producing cells cultured on or in the selectively permeable material of the flexible tubular structure. In an aspect, the artificial mucus layer includes a buffer to buffer the low pH of the chyme entering the small intestine from the stomach.

In an aspect, the at least one microbe-promoting agent includes a binding agent. For example, at least one surface of the flexible tubular structure of the gastrointestinal device can include a binding agent configured to bind at least one type of commensal microbe to promote attraction, colonization and/or growth of said at least one type of commensal microbe. For example, at least one surface of the flexible tubular structure of the gastrointestinal device can include a binding agent configured to bind at least one first type of commensal microbe to promote attraction, colonization and/or growth of at least one second type of commensal microbe. In an aspect, the binding agent is configured to hold the at least one type of commensal microbe in a specific position on the flexible tubular structure. In an aspect, the binding agent is configured to bind endogenous microbes. For example, the binding agent can be configured to bind endogenous commensal microbes. For example, the binding agent can be configured to bind pathogenic microbes, e.g., ingested pathogenic microbes. In an aspect, the binding agent is configured to bind administered microbes. For example, the binding agent can be configured to bind at least one type of orally administered commensal microbes, e.g., a commensal gut microbe, at least part of a gut microbiota, at least one type of commensal microbe from a fecal sample, a probiotic, a genetically engineered microbe, and/or a commensal microbe derived from in vitro culture. For example, the binding agent can be configured to bind at least one type of rectally administered commensal microbes, e.g., a commensal gut microbe, at least part of a gut microbiota, at least one type of commensal microbe from a fecal sample, a probiotic, a genetically engineered microbe, and/or a commensal microbe derived from in vitro culture.

In an aspect, the binding agent includes a non-selective binding agent. In an aspect, the non-selective binding agent includes an adhesive, an absorbent, an adsorbent, or a gel. In an aspect, the non-selective binding agent includes a biomolecule-binding polymer. For example, the non-selective binding agent can include a material, e.g., a gel, which non-selectively binds microbes to the flexible tubular structure of the gastrointestinal device. In an aspect, the at least one binding agent interacts with biomolecules on the outer surface of microbes, e.g., proteins, polysaccharides, carbohydrates, phospholipids, proteoglycans, and the like, non-limiting examples of which include poly-ionic surfaces, e.g., poly-cationic surfaces such as polyamino acids (e.g., polylysine), fibronectin, nitrocellulose, cellulose nitrate, hydrophobic polymers, polyvinylidene fluoride coating, nylon coating, streptavidin or biotin, proteins, peptides, Concanavalin A, epoxy for binding proteins and peptides, aldehydes for immobilizing amino modified oligos and cDNAs, native proteins, tissues, and cells, and amines for immobilizing long oligos and cDNAs. Other non-limiting examples include adhesives, absorbents, adsorbents, gels (e.g., hydrogels, colloids, agar, or gelatin), biomolecule-binding polymers (e.g., nitrocellulose or poly-L-lysine), and extracellular matrix components (e.g., collagen, laminin, fibronectin, mucopolysaccharides, heparin sulfate, hyaluronidate, and chondroitin sulfate).

In an aspect, the binding agent includes a selective binding agent. In an aspect, the selective binding agent is configured to selectively capture at least one type of commensal microbe. For example, the specific binding agent can be configured to recognize and bind a feature of a specific type of commensal microbe, e.g., a surface protein, lipopolysaccharide, carbohydrate, and the like. In an aspect, the selective binding agent includes an antibody, an aptamer, a DNA fragment, an RNA fragment, a protein, or a peptide. Other non-limiting examples of binding agents include antibody fragments, peptides, DNA, RNA, peptide nucleic acids, proteins, viruses, lipid, glycolipids, sphingolipids, phospholipids, carbohydrates, enzymes, receptors, lectins, peptide aptamers, bacteria, cells, cell fragments, inorganic molecules, organic molecules, artificial binding substrates (e.g., those formed by molecular imprinting), or combinations thereof.

In an aspect, the binding agent can include a ligand that specifically recognizes one or more microbes. For example, the binding agent can include CD14, which is a protein associated with monocyte/macrophages and known to bind lipopolysaccharide associated with Gram-negative bacteria as well as lipoteichoic acid associated with the Gram-positive bacteria *Bacillus subtilis* (see, e.g., Fan, et al. (1999) *Infect. Immun.* 67:2964-2968). In an aspect, the binding agent can include all or part of a pattern recognition receptor that recognizes microbe-specific molecules (e.g., bacterial carbohydrates, bacterial or viral DNA or RNA, bacterial peptides, peptidoglycans, lipoteichoic acids, N-formylmethionine, lipoproteins, and fungal glucans). Non-limiting examples of pattern recognition receptors with microbe-binding properties include toll-like receptors, C-type lectin receptors, NOD-like receptors, RIG-I-like receptors, RNA helicases, complement receptors, collectins, ficolins, pentraxins, C-reactive proteins, lipid transferases, and the like. See, e.g., Modlin (2012) *J. Invest. Dermatol.* 132:882-886; Gauglitz et al. (2012) *Acta Derm. Venereol.* 92:291-298, which are incorporated herein by reference.

In an aspect, the at least one microbe-promoting agent includes at least one lectin. Lectins include carbohydrate-binding proteins that bind cell surface glycoproteins and/or glycolipids. Non-limiting examples of lectins include algal lectins, e.g., b-prism lectin; animal lectins, e.g., tachylectin-2, C-type lectins, C-type lectin-like proteins, calnexin-calreticulin, capsid protein, chitin-binding protein, ficolins, fucolectin, H-type lectins, I-type lectins, sialoadhesin, siglec-5, siglec-7, micronemal protein, P-type lectins, pentrxin, b-trefoil, galectins, congerins, selenocosmia huwena lectin-I, Hcgp-39, Ym1; bacterial lectins, e.g., *Pseudomonas* PA-IL, *Burkholderia* lectins, *chromobacterium* CV-IIL, *Pseudomonas* PA IIL, *Ralstonia* RS-ILL, ADP-ribosylating toxin, *Ralstonia* lectin, *Clostridium* hemagglutinin, botulinum toxin, tetanus toxin, cyanobacterial lectins, FimH, GafD, PapG, *Staphylococcal* enterotoxin B, toxin SSL11, toxin SSL5; fungal and yeast lectins, e.g., *Aleuria aurantia* lectin, integrin-like lectin, *Agaricus* lectin, *Sclerotium* lectin, *Xerocomus* lectin, *Laetiporus* lectin, *Marasmius oreades* agglutinin, *agrocybe* galectin, *coprinus* galectin-2, Ig-like lectins, L-type lectins; plant lectins, e.g., alpha-D-mannose-specific plant lectins, *amaranthus* antimicrobial peptide, hevein, pokeweed lectin, *Urtica dioica* UD, wheat germ WGA-1, WGA-2, WGA-3, artocarpin, artocarpus hirsute AHL, banana lectin, Calsepa, heltuba, jacalin, *Maclura pomifera* MPA, MornigaM, Parkia lectins, abrin-a, abrus agglutinin, amaranthin, castor bean ricin B, ebulin, mistletoe lectin, TKL-1, cyanovirin-N homolog, and various legume lectins; and viral lectins, e.g., capsid protein, coat protein, fiber knob, hemagglutinin, and tailspike protein. See, e.g., Kumar & Mittal (2011) *Bioinformation* 6:134-136, which is incorporated herein by reference.

In an aspect, the at least one microbe-promoting agent comprises a coating on the at least one of the inner surface and the outer surface of the flexible tubular structure. For example, the at least one microbe-promoting agent can include a coating of mucin-like proteins to form an artificial mucus layer on one or more surfaces of the flexible tubular structure. In an aspect, the at least one microbe-promoting agent is embedded in the at least one of the inner surface and the outer surface of the flexible tubular structure. For example, the at least one microbe-promoting agent can be embedded into a degradable material forming the flexible tubular structure, e.g., a degradable polymer material.

In an aspect, the at least one microbe-promoting agent is covalently attached to the at least one of the inner surface and the outer surface of the flexible tubular structure. For example, the at least one microbe-promoting agent can be covalently attached to the flexible tubular structure through a crosslinking reagent, e.g., a homobifunctional, heterobifunctional, and/or photoreactive crosslinking reagent. For example, the at least one microbe-promoting agent can be cross-linked to at least a portion of the inner surface and/or the outer surface of the flexible tubular structure amine groups, carbohydrate groups, sulfhydryl groups, or combinations thereof associated with a surface component, e.g., a protein or carbohydrate, of the at least one type of commensal microbe. A variety of crosslinking reagents are known and available from commercial sources (from, e.g., Pierce-Thermo Fisher Scientific, Inc., Rockford, Ill.). In an aspect, the at least one microbe-promoting agent is non-covalently attached to the at least one of the inner surface and the outer surface of the flexible tubular structure.

In an aspect, the at least one microbe-promoting agent is incorporated into a degradable coating on the at least a portion of the at least one of the inner surface and the outer surface of the flexible tubular structure. For example, the at least one microbe-promoting agent can be incorporated into a coating material that degrades over time to release the at least one microbe-promoting agent. In an aspect, the at least one microbe-promoting agent is incorporated into a stimulus-responsive degradable coating on the at least a portion of the at least one of the inner surface and the outer surface of the flexible tubular structure. For example, the at least one microbe-promoting agent can be incorporated into a coating material that degrades in response to a stimulus, e.g., time, moisture, temperature, pH, or chemicals.

In an aspect, the stimulus-responsive degradable coating includes at least one of a time-responsive degradable coating, a moisture-responsive degradable coating, a temperature-responsive degradable coating, a pH-responsive degradable coating, or a chemical-responsive degradable coating. In an aspect, the stimulus-responsive degradable coating includes a time-responsive degradable coating. For example, the at least one microbe-promoting agent can be incorporated into a time-responsive degradable coating that degrades over time to release the at least one microbe-promoting agent. In an aspect, the stimulus-responsive degradable coating includes a moisture-responsive degradable coating. For example, the at least one microbe-promoting agent can be incorporated into a moisture-responsive degradable coating that degrades over time in responsive to moisture associated with the gastrointestinal tract to release the at least one microbe-promoting agent.

In an aspect, the stimulus-responsive degradable coating includes a temperature-responsive degradable coating. For example, the at least one microbe-promoting agent can be incorporated into a temperature-responsive degradable coating that degrades over time in response to body heat, e.g., 37 degrees centigrade, associated with the gastrointestinal tract to release the at least one microbe-promoting agent. For example, the at least one microbe-promoting agent can be incorporated into a pH-responsive degradable coating that degrades over time in response to pH changes in the gastrointestinal tract as ingested material moves from the stomach (pH 1.0-3.0) into the upper (pH 4.8-8.2) and the lower (pH 7.0-7.5) intestinal tract to release the at least one microbe-promoting agent. Non-limiting examples of temperature-responsive and pH-responsive polymers are described in Schmaljohann (2006) *Adv. Drug Deliv. Rev.* 58:1655-1670, which is incorporated herein by reference.

In an aspect, the stimulus-responsive degradable coating includes a chemical-responsive degradable coating. For example, the at least one microbe-promoting agent can be incorporated into a chemical-responsive degradable coating that degrades in response to either an endogenous chemical or an administered/ingested chemical to release the at least one microbe-promoting agent. For example, the chemical-responsive degradable coating can include a hydrogel that is responsive to a chemical, e.g., glucose, a protein, an antibody, or an aptamer. See, e.g., Yang et al. (2008) *J. Am. Chem. Soc.* 130:6320-6321; Miyata et al. (2006) *Proc. Natl. Acad. Sci.* 103:1190-1193, which are incorporated herein by reference.

In an aspect, the gastrointestinal device includes at least one first microbe-promoting agent in a first degradable coating and at least one second microbe-promoting agent in a second degradable coating. In an aspect, the first degradable coating and the second degradable coating degrade at different rates. For example, the at least one first microbe-promoting agent can be in a first time-responsive degradable coating configured to degrade at a first rate and the at least one second microbe-promoting agent can be in a second time-responsive degradable coating configured to degrade at a second rate. For example, the at least one first microbe-promoting agent can be in a first stimulus-responsive degradable coating and the at least one second microbe-promoting agent in a second stimulus-responsive degradable coating, the first stimulus-responsive degradable coating degrading at a different pH or temperature than the second stimulus-responsive degradable coating. For example, the at least one first microbe-promoting agent can be in a first chemical-responsive degradable coating and the at least one second microbe-promoting agent in a second chemical-responsive degradable coating, the first chemical-responsive degradable coating degrading in response to a first chemical and the second chemical-responsive degradable coating degrading in response to a second chemical.

In an aspect, a gastrointestinal device including at least one microbe-promoting agent further includes at least one therapeutic agent. For example, the gastrointestinal device including the at least one microbe-promoting agent can include at least one anti-inflammatory agent, chemotherapeutic agent, or antimicrobial agent. In an aspect, a gastrointestinal device including at least one microbe-promoting agent further includes at least one bioactive agent. For example, the gastrointestinal device including the at least one microbe-promoting agent can include at least one digestive enzyme. For example, the at least one bioactive agent can further include antiseptic enzymes (e.g., lysozyme) immunoglobulins, inorganic salts, and proteins (e.g., lactoferrin). Non-limiting examples of therapeutic agents and bioactive agents have been described above herein.

The gastrointestinal device having a flexible tubular structure including at least one microbial-promoting agent further includes at least one anchor structure including one or more gastric wall-engaging components. In an aspect, the at least one anchor structure is attached to the proximal end of the flexible tubular structure. In an aspect, the at least one anchor structure is attached to the distal end of the flexible tubular structure. In an aspect, the at least one anchor structure is incorporated into the flexible tubular structure. In an aspect, the at least one anchor structure includes one or more gastric wall-engaging components positioned along at least a portion of the flexible tubular structure. In an aspect, the one or more gastric wall-engaging components include one or more barbs or one or more hooks. In an aspect, the one or more gastric wall-engaging components include an adhesive or an adherent. In an aspect, the one or more gastric wall-engaging components include a clip. In an aspect, the at least one anchor structure is inflatable. In an aspect, the at least one anchor structure is expandable. Non-limiting examples of anchor structures have been described above herein.

Figure 24:
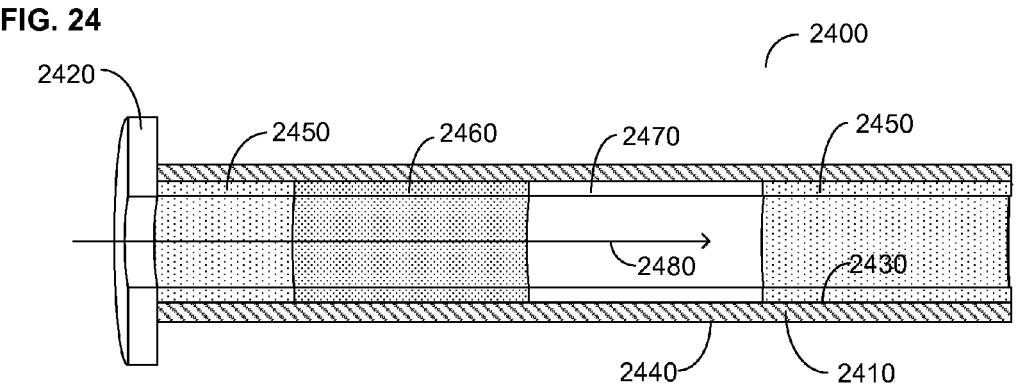
FIG. 24 is a schematic of a cross-section through gastrointestinal device including multiple types of microbe-promoting agents on an inner surface.
Figure 25:
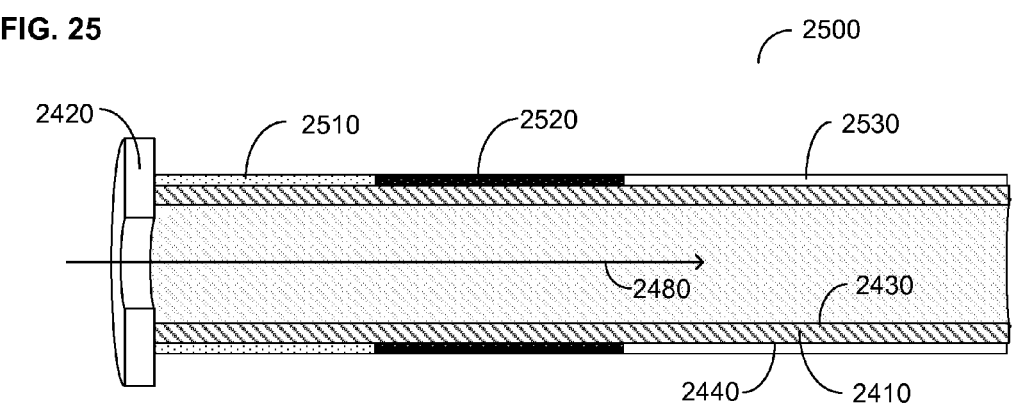
FIG. 25 is a schematic of a cross-section through a gastrointestinal device including multiple types of microbe-promoting agents on an outer surface.
Figure 26:
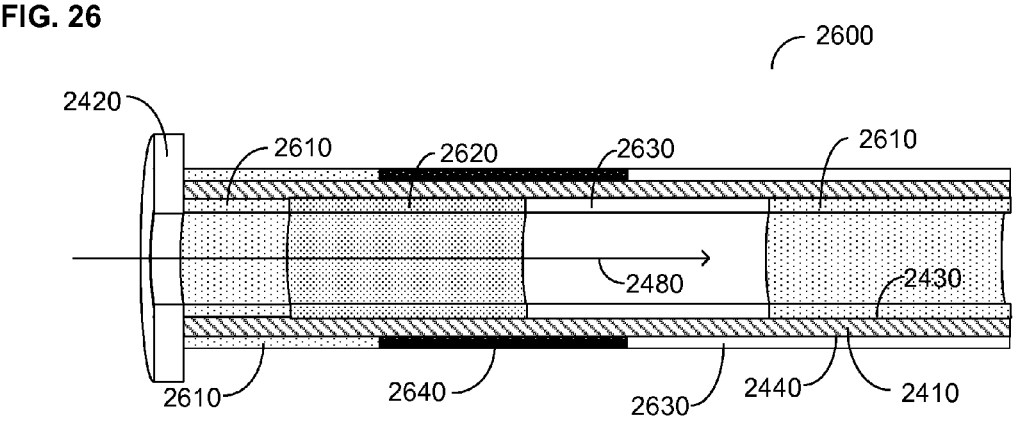
FIG. 26 is a schematic of a cross-section through a gastrointestinal device including multiple types of microbe-promoting agents on an inner surface and outer surface.

In an aspect, a gastrointestinal device includes at least one first microbe-promoting agent associated with at least one first portion of the flexible tubular structure and at least one second microbe-promoting agent associated with at least one second portion of the flexible tubular structure. In an aspect, a gastrointestinal device includes at least one first microbe-promoting agent on a first portion of the flexible tubular structure and at least one second microbe-promoting agent on a second portion of the flexible tubular structure. FIGS. 24-26 illustrate aspects of a gastrointestinal device including at least one first microbe-promoting agent and at least one second microbe-promoting agent associated with at least one of the inner surface and the outer surface of a flexible tubular structure. FIG. 24 shows a cross-section through gastrointestinal device 2400. Gastrointestinal device 2400 includes flexible tubular structure 2410 (diagonal pattern) and at least one anchor structure 2420. Flexible tubular structure 2410 includes an inner surface 2430, an outer surface 2440, and a flow conduit 2480. Flexible tubular structure 2410 further includes at least one first microbe-promoting agent 2450 on a first portion of inner surface 2430, at least one second microbe-promoting agent 2460 on a second portion of inner surface 2430, at least one third microbe-promoting agent 2470 on a third portion of inner surface 2430, and the at least one first microbe-promoting agent 2450 on a fourth portion of inner surface 2430.

FIG. 25 shows a cross-section through gastrointestinal device 2500. Gastrointestinal device 2500 includes flexible tubular structure 2410 (diagonal pattern) and at least one anchor structure 2420. Flexible tubular structure 2410 includes an inner surface 2430, an outer surface 2440, and a flow conduit 2480. Flexible tubular structure 2410 further includes at least one first microbe-promoting agent 2510 on a first portion of outer surface 2440, at least one second microbe-promoting agent 2520 on a second portion of outer surface 2440, and at least one third microbe-promoting agent 2530 on a third portion of outer surface 2440.

FIG. 26 shows a cross-section through gastrointestinal device 2600. Gastrointestinal device 2600 includes flexible tubular structure 2410 (diagonal pattern) and at least one anchor structure 2420. Flexible tubular structure 2410 includes an inner surface 2430, an outer surface 2440, and a flow conduit 2480. Flexible tubular structure 2410 further includes at least one first microbe-promoting agent 2610 on a first portion of inner surface 2430, at least one second microbe-promoting agent 2620 on a second portion of inner surface 2430, at least one third microbe-promoting agent 2630 on a third portion of inner surface 2430, the at least one first microbe-promoting agent 2610 on a fourth portion of inner surface 2430, at least one first microbe-promoting agent 2610 on a first portion of outer surface 2440, at least one fourth microbe-promoting agent 2640 on a second portion of outer surface 2440, and the at least one third microbe-promoting agent 2630 on a third portion of outer surface 2440.

Gastrointestinal Device with a Layered Wall Encasing at Least One Microbe-Promoting Agent A gastrointestinal device is described that includes a layered wall encasing at least one microbe-promoting agent. In an aspect, a gastrointestinal device includes a flexible tubular structure including a layered wall, the flexible tubular structure including at least one microbe-promoting agent encased in the layered wall of the flexible tubular structure, the at least one microbe-promoting agent configured to promote at least one of attraction, colonization, and growth of at least one type of commensal microbe; and a proximal and a distal end, the proximal end and the distal end forming a flow conduit through the flexible tubular structure; and at least one anchor structure including one or more gastric wall-engaging components configured to engage a wall of the gastrointestinal tract of a subject.

Figure 27:
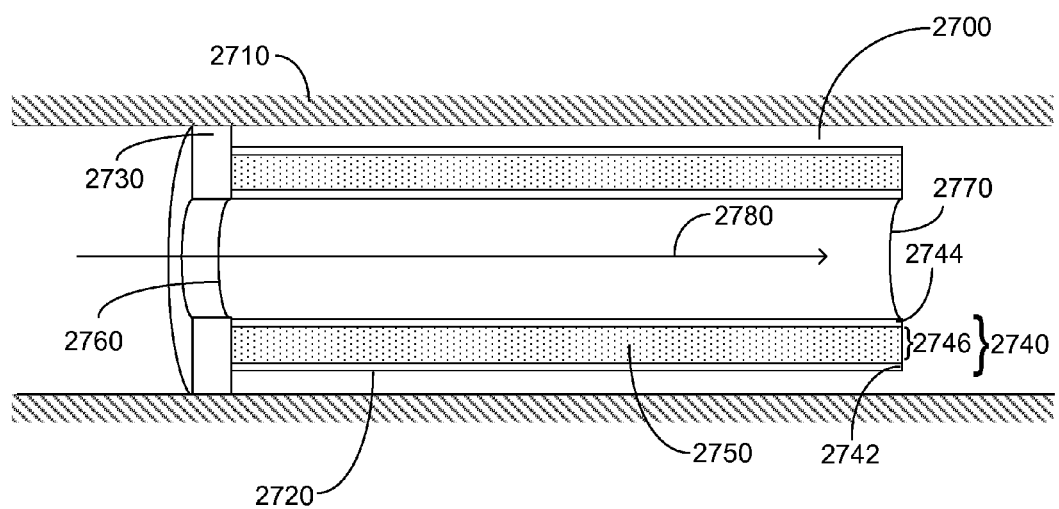
FIG. 27 is a schematic of a cross-section through a gastrointestinal device including a layered wall encasing at least one microbe-promoting agent.

FIG. 27 shows a cross-sectional view through gastrointestinal device 2700 including a flexible tubular structure 2710 including a layered wall 2740, the flexible tubular structure 2710 including at least one microbe-promoting agent encased in the layered wall 2740, the layered wall 2740 configured to allow interaction between the at least one microbe-promoting agent 2750 and at least one of the gastrointestinal wall 2710 and an ingested product within the flexible tubular structure; a proximal end 2760 and a distal end 2770, the proximal end 2760 and the distal end 2770 forming a flow conduit 2780 through the flexible tubular structure 2710; and at least one anchor structure 2730 including one or more gastric wall-engaging components configured to engage a wall of the gastrointestinal tract of a subject. In an aspect, the layered wall 2740 includes an outer layer 2742, an inner layer 2744, and an internal space 2746, the outer layer 2742 proximal to the wall of the gastrointestinal tract 2710, the inner layer 2744 proximal to the flow conduit 2780 through the flexible tubular structure, and the internal space 2746 positioned between the outer layer 2742 and the inner layer 2744 and including the at least one microbe-promoting agent 2750. In an aspect, at least one of the outer layer 2742 and the inner layer 2744 is semi-permeable.

In an aspect, at least one of the outer layer 2742 and the inner layer 2744 of gastrointestinal device 2700 is permeable to at least one type of commensal microbe. In an aspect, at least one of the outer layer and the inner layer of the gastrointestinal device is permeable to at least one type of commensal microbe from ingested material, e.g., orally administered commensal microbes, or pathogenic microbes in a food product). In an aspect, at least one of the outer layer and the inner layer of the gastrointestinal device is permeable to at least one type of commensal microbe from the gastrointestinal wall. In an aspect, at least one of the outer layer and the inner layer of the gastrointestinal device is permeable to at least one type of pathogenic microbe from the gastrointestinal wall.

In an aspect, the layered wall of the flexible tubular structure of gastrointestinal device 2700 is configured to allow an interaction between the at least one microbe-promoting agent and one or more ingested components within the flexible tubular structure. For example, the layered wall may include a semi-permeable inner layer that permits lateral movement of one or more ingest components (e.g., ingested commensal microbes) within the flexible tubular structure to transit into and/or through the layered wall and come into contact with the at least one microbe-promoting agent. For example, the flexible tubular structure can include a layered wall having at least one microbe-promoting agent configured to promote at least one of attraction, colonization, and/or growth of at least one type of administered (e.g., orally administered) commensal microbe within the layered wall.

In an aspect, the layered wall of the flexible tubular structure of gastrointestinal device 2700 is configured to allow an interaction between the at least one microbe-promoting agent and one or more components of the gastrointestinal tract. For example, the flexible tubular structure can include a layered wall having at least one microbe-promoting agent configured to promote at least one of attraction, colonization, and/or growth of at least one type of commensal microbe within the layered wall. For example, the flexible tubular structure can include a layered wall having at least one microbe-promoting agent configured to promote at least one of attraction, colonization, and/or growth of at least one type of endogenous commensal microbe within the layered wall.

In an aspect, at least one of the outer layer 2742 and the inner layer 2744 of gastrointestinal device 2700 is permeable to the at least one microbe-promoting agent. In an aspect, gastrointestinal device 2700 is configured to deliver at least one microbe-promoting agent to the gastrointestinal wall. For example, the outer layer of the layered wall may be permeable to the at least one microbe-promoting agent, permitting the at least one microbe-promoting agent to move laterally out towards the gastrointestinal wall. In an aspect, gastrointestinal device 2700 is configured to deliver at least one microbe-promoting agent to the interior portion of the flexible tubular structure. For example, the inner layer of the layered wall may be permeable to at least one microbe-promoting agent, permitting the at least one microbe-promoting agent to move laterally out towards the interior of the flexible tubular structure to interact with ingested contents within the flexible tubular structure or with ingested contents and/or gastrointestinal components downstream from the position of the gastrointestinal device.

In an aspect, gastrointestinal device 2700 including flexible tubular structure 2720 and at least one anchor structure 2730 is sized for placement in a portion of the gastrointestinal tract. In an aspect, at least a portion of gastrointestinal device 2700 is sized for placement in a mouth, esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof.

In an aspect, flexible tubular structure 2720 is a sleeve, a liner, or a stent. In an aspect, flexible tubular structure 2720 is sized for placement in a mouth, esophagus, a stomach, a pylorus, a duodenum, a jejunum, an ileum, a caecum, a sphincter, a duct, a biliary duct, a pancreatic duct, a gland, an ascending colon, a transverse colon, a descending colon, a sigmoid colon, a rectum, an anus, or a combination thereof. Non-limiting examples of dimensions for a flexible tubular structure, for example, have been described above here.

In an aspect, flexible tubular structure 2720 is of a type to treat a medical condition of the subject. In an aspect, the medical condition of the subject includes at least one of diabetes, obesity, metabolic syndrome, colitis, cancer, inflammatory bowel disease, irritable bowel syndrome, an autoimmune disorder, trauma, stricture, microbial infection, or microbial deficit.

In an aspect, at least one of the outer layer and the inner layer is formed from a semi-permeable material. In an aspect, the semi-permeable material is selectively permeable. In an aspect, the semi-permeable material is selectively permeable based on at least one of size, hydrophobicity, or charge. In an aspect, the semi-permeable material includes a plurality of pores. In an aspect, the outer layer or the inner layer is formed from a substantially impermeable material. Non-limiting examples of semi-permeable and substantially impermeable materials have been described above herein.

In an aspect, the layered wall of the flexible tubular structure of the gastrointestinal device includes an attachment mechanism for holding the outer layer and the inner layer together. In an aspect, the attachment mechanism includes a material, e.g., an adhesive, adherent, gel, or matrix, in the internal space that holds the outer layer and the inner layer together. For example, the internal space including the at least one microbe-promoting agent can include a material, e.g., an adhesive, adherent, gel, or matrix, to which the outer layer and the inner layer adhere. In an aspect, the attachment mechanism includes one or more staples, stitches, pins, or like mechanism for holding the outer layer and the inner layer together. In an aspect, the inner layer and the outer layer are fused together at specific points along the length of the flexible tubular structure in response to a stimulus, e.g., pressure, heat, or chemical stimulus. In an aspect, the attachment mechanism is degradable. In an aspect, the inner layer and the outer layer are held together through the at least one anchor structure. For example, the inner layer and the outer layer of the layered wall of the flexible tubular structure can be separately attached to at least one anchor structure, e.g., at the proximal and/or distal ends of the flexible tubular structure.

Figure 28:
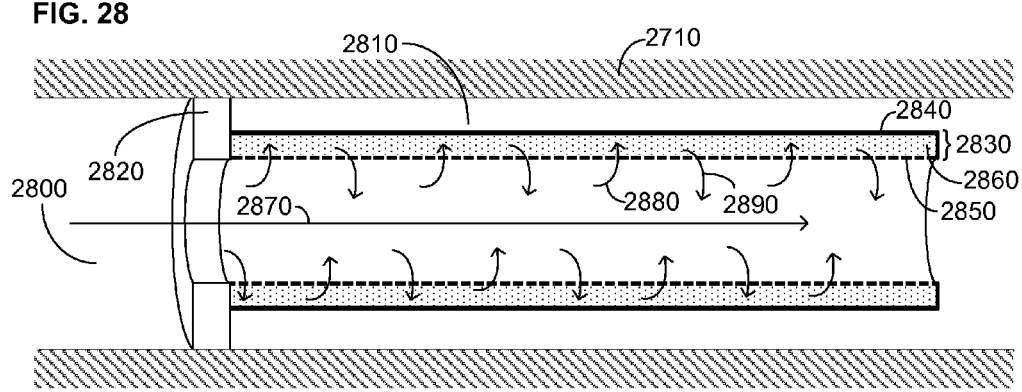
FIG. 28 is a schematic of a cross-section through a gastrointestinal device including a layered wall encasing at least one microbe-promoting agent and including an inner layer formed from a semi-permeable material.
Figure 29:
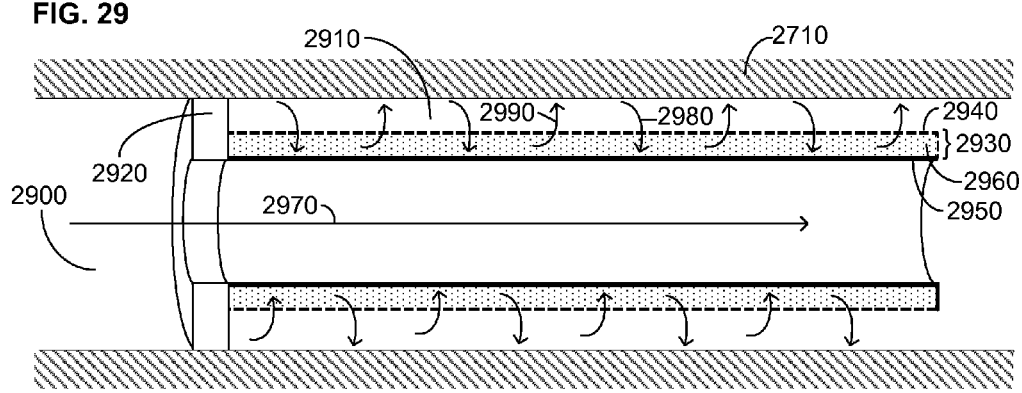
FIG. 29 is a schematic of a cross-section through a gastrointestinal device including a layered wall encasing at least one microbe-promoting agent and including an outer layer formed from a semi-permeable material.
Figure 30:
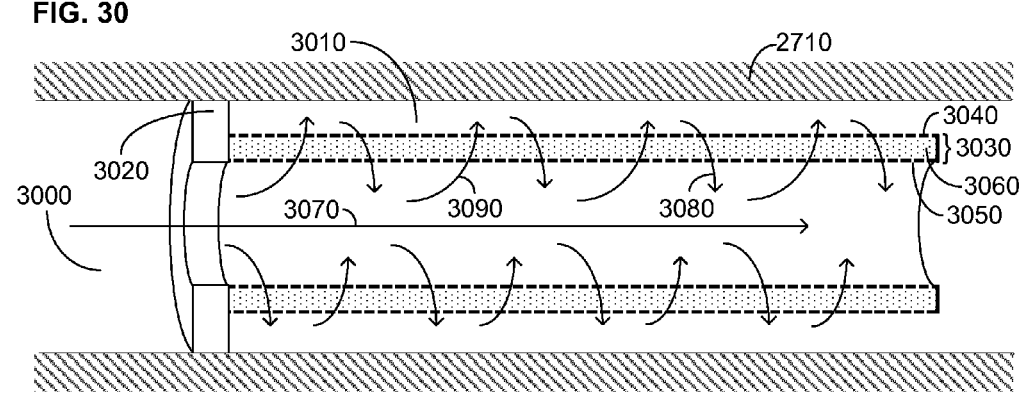
FIG. 30 is a schematic of a cross-section through a gastrointestinal device including a layered wall encasing at least one microbe-promoting agent and including an inner layer and an outer layer formed from a semi-permeable material.

FIGS. 28-30 show non-limiting embodiments of a gastrointestinal device including a flexible tubular structure with a layered wall encasing at least one microbe-promoting agent. In an aspect, the layered wall of the flexible tubular structure includes an outer layer that is substantially impermeable and an inner layer that is at least semi-permeable, as illustrated in FIG. 28. FIG. 28 shows a cross-sectional view through gastrointestinal device 2800 positioned in the gastrointestinal tract 2710 of a subject. Gastrointestinal device 2800 includes flexible tubular structure 2810 and at least one anchor structure 2820. Flexible tubular structure 2810 includes a layered wall 2830. Layered wall 2830 includes an outer layer 2840 formed from a substantially impermeable material and an inner layer 2850 formed from a semi-permeable material. Layered wall 2830 further includes internal space 2860 including at least one microbe-promoting agent. Flexible tubular structure 2810 includes flow conduit 2870 through which ingested products are able to flow. Layered wall 2830 is configured to allow flow inward 2880 of ingested products through the semi-permeable inner layer 2850 but not through substantially impermeable outer layer 2840. Layered wall 2830 is further configured to allow flow outward 2890 from the internal space 2860 through the semi-permeable inner layer 2850.

In an aspect, the layered wall of the flexible tubular structure includes an outer layer that is at least semi-permeable and an inner layer that is substantially impermeable, as illustrated in FIG. 29. FIG. 29 shows a cross-sectional view through gastrointestinal device 2900 positioned in the gastrointestinal tract 2710 of a subject. Gastrointestinal device 2900 includes flexible tubular structure 2910 and at least one anchor structure 2920. Flexible tubular structure 2910 includes a layered wall 2930. Layered wall 2930 includes an outer layer 2940 formed from a semi-permeable material and an inner layer 2950 formed from a substantially impermeable material. Layered wall 2930 further includes internal space 2960 including at least one microbe-promoting agent. Flexible tubular structure 2910 includes flow conduit 2970 through which ingested products are able to flow. Layered wall 2930 is configured to allow flow inward 2980 of components from the gastrointestinal tract, e.g., digestive enzymes and/or resident microbes, through the semi-permeable outer layer 2940. Layered wall 2930 is further configured to allow flow outward 2990 through outer layer 2940. In this configuration, the layered wall 2930 does not allow flow through the substantially impermeable inner layer to the flow conduit 2970.

In an aspect, the layered wall of the flexible tubular structure includes an outer layer that is semi-permeable and an inner layer that is semi-permeable, as illustrated in FIG. 30. FIG. 30 shows a cross-section through gastrointestinal device 3000 positioned in the gastrointestinal tract 2710 of a subject. Gastrointestinal device 3000 includes flexible tubular structure 3010 and at least one anchor structure 3020. Flexible tubular structure 3010 includes a layered wall 3030. Layered wall 3030 includes an outer layer 3040 formed from a semi-permeable material and an inner layer 3050 formed from a semi-permeable material. Layered wall 3030 further includes internal space 3060 including at least one microbe-promoting agent. Flexible tubular structure 3010 includes flow conduit 3070 through which ingested products are able to flow. Layered wall 3030 is configured to allow flow inward 3080 of components from the gastrointestinal tract, e.g., digestive enzymes and/or resident microbes, through the semi-permeable outer layer 3040, the internal layer 3060, the inner layer 3050, and into the flow conduit 3070 of the flexible tubular structure 3010. Layered wall 3030 is further configured to allow flow outward 3080 from the flow conduit 3070 of the flexible tubular structure 3010, through inner layer 3050, internal space 3060, and outer layer 3040 to the wall region of the gastrointestinal tract 2710.

In an aspect, the layered wall of the flexible tubular structure includes an outer layer and an inner layer. In an aspect, the outer layer is formed from a first semi-permeable material and the inner layer is formed from a second semi-permeable material. In an aspect, the first semi-permeable material and the second semi-permeable material are the same semi-permeable material. In an aspect, the first semi-permeable material and the second semi-permeable material are different semi-permeable materials. In an aspect, the first semi-permeable material and the second semi-permeable material are selectively permeable. In an aspect, the at least one of the first semi-permeable material and the second semi-permeable material is selectively permeable based on at least one of size, hydrophobicity, or charge. For example, the first semi-permeable material may have a first size exclusion, e.g., 100,000 mw, and the second semi-permeable material may have a second size exclusion, e.g., 10,000 mw, allowing large ingested products to pass into the semi-permeable wall but only smaller ingest products to exit out the other side. In an aspect, at least one of the first semi-permeable material and the second semi-permeable material includes a plurality of pores. For example, the first semi-permeable material may include pores sized to allow transit of at least one type of commensal microbe and the second semi-permeable material may include pores sized to exclude the at least one type of commensal microbe, the first semi-permeable material allowing the at least one type of commensal microbe to pass into the layered wall through the first semi-permeable material to colonize and grow in response to the at least one microbe-promoting agent, the second semi-permeable material prohibiting the at least one type of commensal microbe from passing through the layered wall. Non limiting examples of semi-permeable and substantially impermeable material have been described above herein.

In an aspect, the layered wall of the flexible tubular structure includes an internal space including the at least one microbe-promoting agent. In an aspect, the internal space including the at least one microbe-promoting agent includes a permeable material. In an aspect, the permeable material includes at least one of a mucus material, a gel material, a porous material, a matrix material, or a fibrous material. In an aspect, the at least one microbe-promoting agent is associated with a permeable material. For example, the internal space of the layered wall can include a material that allows for unhindered movement/diffusion of the at least one microbe-promoting agent or any ingested components or gastrointestinal components that have moved into the layered wall. For example, the internal space of the layered wall of the gastrointestinal device can include a material that allows for free flow of fluid and materials through the internal space within the confines of the outer layer and inner layer of the layered wall. In an aspect, the at least one microbe-promoting agent is associated with at least one of a porous material, a fibrous material, a mucus material, or a gel material in the layered wall. In an aspect, the at least one microbe-promoting agent is immobilized in the layered wall. For example, the at least one microbe-promoting agent can adhere to materials (e.g., fibers) or pores associated with an internal space of the layered wall. For example, the at least one microbe-promoting agent can line an exposed surface of a pore, allowing for interaction between the at least one microbe-promoting agent and an ingested product and/or gastrointestinal component. In an aspect, the at least one microbe-promoting agent is diffusible from the layered wall. For example, at least one of the inner layer or the outer layer can be formed from a material sufficiently porous enough to allow passage of the at least one microbe-promoting agent.

In an aspect, the at least one microbe-promoting agent is included in a degradable coating or matrix associated with the internal space of the layered wall of the flexible tubular structure. In an aspect, the at least one microbe-promoting agent is included in a stimulus-responsive degradable coating or matrix associated with the internal space of the layered wall of the flexible tubular structure. For example, the at least one microbe-promoting agent can be associated with a time, moisture, pH, temperature, or chemical responsive degradable coating or matrix associated with the internal space of the layered wall of the flexible tubular structure.

In an aspect, at least a portion of the flexible tubular structure is degradable. In an aspect, at least a portion of the layered wall is degradable. For example, at least one of the inner layer, outer layer, and internal space can be formed from a degradable material configured to degrade over time. For example, at least one of the inner layer, outer layer, and internal space can be formed from a degradable material that degrades over time in response to temperature, moisture, pH, or a chemical. In an aspect, the flexible tubular structure is noncontiguous. For example, the flexible tubular structure can include two or more segments attached to one another through a degradable linker that degrades over time to release the two or more segments.

Gastrointestinal device 2700 includes at least one microbe-promoting agent encased in the layered wall of the flexible tubular structure, the at least one microbe-promoting agent configured to promote at least one of attraction, colonization, and growth of at least one type of commensal microbe. In an aspect, the at least one microbe-promoting agent is configured to promote at least one of attraction, colonization, and growth of at least one type of endogenous commensal microbe. For example, the at least one microbe-promoting agent can be configured to promote attraction, colonization, and/or growth of at least one type of commensal microbe resident in the gastrointestinal tract of the subject. In an aspect, the at least one microbe-promoting agent is configured to promote at least one of attraction, colonization, and growth of at least one type of commensal gut microbe. In an aspect, the at least one microbe-promoting agent is configured to promote at least one of attraction, colonization, and growth of at least part of a gut microbiota.

In an aspect, the at least one microbe-promoting agent is configured to promote at least one of attraction, colonization, and growth of at least one type of administered commensal microbe. In an aspect, the at least one microbe-promoting agent is configured to promote at least one of attraction, colonization, and growth of at least one type of commensal microbe derived from a fecal sample. In an aspect, the at least one microbe-promoting agent is configured to promote at least one of attraction, colonization, and growth of at least one type of genetically engineered microbe. In an aspect, the at least one microbe-promoting agent is configured to promote at least one of attraction, colonization, and growth of at least one type of commensal microbe derived from in vitro culture. In an aspect, the at least one microbe-promoting agent is configured to promote at least one of attraction, colonization, and growth of at least one type of probiotic. For example, the at least one microbe-promoting agent can be configured to promote attraction, colonization, and/or growth of an orally ingested commensal microbe, e.g., a commensal gut microbe, at least part of a gut microbiota, at least one type of commensal microbe from a fecal sample, a probiotic, a genetically engineered microbe, and/or a commensal microbe derived from in vitro culture. For example, the at least one microbe-promoting agent can be configured to promote attraction, colonization, and/or growth of an orally ingested commensal microbe administered in a dehydrated form (e.g., in powder, capsule, or pill form), liquid form, suspended form, or paste form.

In an aspect, the layered wall of the flexible tubular structure includes at least one microbe-promoting agent configured to promote at least one of attraction, colonization, and growth of at least one type of commensal microbe beneficial to a subject. In an aspect, the at least one microbe-promoting agent is configured to promote at least one of attraction, colonization, and growth of at least one type of commensal microbe beneficial to a subject having a medical condition. In an aspect, the at least one microbe-promoting agent is configured to promote at least one of attraction, colonization, and growth of at least one type of commensal microbe beneficial to a subject having at least one of diabetes, obesity, metabolic syndrome, colitis, cancer, inflammatory bowel disease, irritable bowel syndrome, an autoimmune disorder, a microbial infection, or a microbial deficit. In an aspect, the at least one microbe-promoting agent is configured to promote at least one of attraction, colonization, and growth of at least one type of commensal microbe beneficial to the immune system of the subject. In an aspect, the at least one microbe-promoting agent is configured to promote at least one of attraction, colonization, and growth of at least one type of commensal microbe beneficial to a dietary condition of the subject. In an aspect, the dietary condition of the subject includes a dietary need of the subject (e.g., a nutritional need), weight control of the subject (e.g., obesity), or a food sensitivity of the subject (e.g., a gluten sensitivity or inability to digest lactose).

In an aspect, the at least one microbe-promoting agent is configured to promote formation of a microbiome. For example, the at least one microbe-promoting agent is configured to promote attraction, colonization, and growth of one or more types of microbes of the microbiome.

In an aspect, the at least one microbe-promoting agent encased in the layered wall includes at least one prebiotic agent. In an aspect, the at least one prebiotic agent includes at least one of a mucopolysaccharide, a chitin, a carrageenan, an arabinogalactin, a starch polysaccharide, an oligosaccharide, a fructo-oligosaccharide, or inulin. In an aspect, the at least one prebiotic agent includes at least one of a protein, a peptide, a lipid, a nutrient, a vitamin, a mineral, or a salt. Other non-limiting examples of prebiotic agents have been described above herein.

In an aspect, the at least one microbe-promoting agent encased in the layered wall includes at least one chemoattractant for attracting a microbe. In an aspect, the chemoattractant includes a ligand that interacts with microbial-chemoreceptors. For example, the chemoattractant can include sugars, e.g., D-maltose, D-ribose, or D-galactose. For example, the chemoattractant can include formyl peptides, e.g., di-, tri-, or tetrapeptides including a formyl group. Non-limiting examples of chemoattractants have been described above herein.

In an aspect, the at least one microbe-promoting agent encased in the layered wall includes mucus. In an aspect, the internal space of the layered wall includes mucus configured to promote at least one of attraction, colonization, and growth of at least one type of commensal microbe. In an aspect, the mucus includes natural mucus. For example, the microbe-promoting agent can include components of natural mucus isolated from a mammalian gastrointestinal tract. In an aspect, the mucus includes synthetic mucus. For example, the microbe-promoting agent can include components of synthetic mucus, e.g., mucin glycoproteins. Other non-limiting examples of mucus and mucus components have been described above herein.

In an aspect, the mucus is produced by cells (e.g., epithelial cells) encased in the layered wall. In an aspect, the mucus produced by the encased epithelial cells remains in the internal space of the layered wall to form a mucus layer. In an aspect, the mucus produced by the encased epithelial cells moves out of the internal space of the layered wall to replenish mucus on the gastrointestinal wall, e.g., that portion of the gastrointestinal wall covered by the gastrointestinal device. For example, the epithelial cells can include intestinal epithelial cells. For example, the epithelial cells can include primary epithelial cells, e.g., isolated from the subject. For example the epithelial cells can include cultured cells. In an aspect, the epithelial cells are derived from stem cells. For example, the epithelial cells can include stem cells, e.g., embryonic or mesenchymal stem cells. For example, various lineages of intestinal epithelial cells can be derived from crypt base columnar cells isolated from the bottom of intestinal crypts. See, e.g., Fujii & Sato (2014) *Frontiers in Genetics*, 5:169, which is incorporated herein by reference.

In an aspect, the at least one microbe-promoting agent encased in the layered wall includes a binding agent. For example, the internal space of the layered wall can include a binding agent configured to bind at least one type of commensal microbe to promote attraction, colonization, and/or growth of said at least one type of commensal microbe. In an aspect, the binding agent is configured to bind at least one first type of commensal microbe, e.g., a probiotic, to promote attraction, colonization, and/or growth of at least one second type of commensal microbe. In an aspect, the binding agent is configured to hold the at least one type of commensal microbe in a specific position, e.g., within the internal space of the layered wall. In an aspect, the binding agent is configured to bind endogenous microbes. For example, the binding agent can be configured to bind endogenous commensal microbes that have migrated from the gastrointestinal wall. For example, the binding agent can be configured to bind pathogenic microbes that have migrated from the gastrointestinal wall. For example, the binding agent can be configured to bind pathogenic microbes, e.g., ingested pathogenic microbes. In an aspect, the binding agent is configured to bind administered microbes. For example, the binding agent can be configured to bind at least one type of orally administered commensal microbes, e.g., a commensal gut microbe, at least part of a gut microbiota, at least one type of commensal microbe from a fecal sample, a probiotic, a genetically engineered microbe, and/or a commensal microbe derived from in vitro culture. For example, the binding agent can be configured to bind at least one type of rectally administered commensal microbes, e.g., a commensal gut microbe, at least part of a gut microbiota, at least one type of commensal microbe from a fecal sample, a probiotic, a genetically engineered microbe, and/or a commensal microbe derived from in vitro culture.

In an aspect, the binding agent includes a non-selective binding agent. In an aspect, the non-selective binding agent includes an adhesive, an absorbent, an adsorbent, or a gel. In an aspect, the non-selective binding agent includes a biomolecule-binding polymer. For example, the internal space of the layered wall can include a material, e.g., a gel, which non-selectively binds microbes to the flexible tubular structure of the gastrointestinal device. In an aspect, the binding agent includes a selective binding agent. In an aspect, the selective binding agent is configured to selectively capture at least one type of commensal microbe. For example, the internal space of the layered wall can include a specific binding agent configured to recognize and bind a feature of a specific type of commensal microbe, e.g., a surface protein, lipopolysaccharide, carbohydrate, and the like. In an aspect, the selective binding agent includes an antibody, an aptamer, a DNA fragment, an RNA fragment, a protein, or a peptide. In an aspect, the selective binding agent can include a ligand that specifically recognizes and binds at least one type of commensal microbe. Non-limiting examples of non-selective and selective binding agents have been described above herein.

In an aspect, the at least one microbe-promoting agent includes at least one lectin. For example, the internal space of the layered wall can include one or more lectins, e.g., carbohydrate-binding proteins that bind glycoproteins and/or glycolipids on the surface of microbes. Non-limiting examples of lectins have been described above herein.

In an aspect, a gastrointestinal device includes a flexible tubular structure with at least one first microbe-promoting agent in a first portion of a layered wall and at least one second microbe-promoting agent in a second portion of the layered wall. FIG. 31 shows a cross-section through gastrointestinal device 3100 positioned in gastrointestinal tract 2710 of a subject. Gastrointestinal device 3100 includes a flexible tubular structure 3110 and at least one anchor structure 3120. Flexible tubular structure 3110 includes layered wall 3130 and flow conduit 3160. Flexible tubular structure 3110 further includes at least one first microbe-promoting agent 3140 in a first portion of the layered wall 3130 and at least one second microbe-promoting agent 3150 in a second portion of the layered wall.

In an aspect, a gastrointestinal device includes a flexible tubular structure with at least one microbe-promoting agent forming a gradient in a layered wall of the flexible tubular structure. FIG. 32 illustrates further aspects of a gastrointestinal device including a layered wall. In an aspect, the at least one microbe-promoting agent forms a gradient within the layered wall. FIG. 32 shows a cross-section through gastrointestinal device 3200 positioned in gastrointestinal tract 2710 of a subject. Gastrointestinal device 3200 includes a flexible tubular structure 3210 and at least one anchor structure 3220. Flexible tubular structure 3210 includes layered wall 3230 and flow conduit 3280. Flexible tubular structure further includes a first concentration 3240 of at least one microbe-promoting agent in a first position of layered wall 3230, a second concentration 3250 of the at least one microbe-promoting agent in a second position of layered wall 3230, a third concentration 3260 of the at least one microbe-promoting agent in a third position of layered wall 3230, and a fourth concentration 3270 of the at least one microbe-promoting agent in a fourth position of layered wall 3230.

In an aspect, gastrointestinal device 2700 further includes at least one therapeutic agent. For example, the gastrointestinal device can include at least one antibiotic. In an aspect, gastrointestinal device 2700 includes at least one bioactive agent. For example, the gastrointestinal device can include at least one digestive enzyme. Other non-limiting examples of therapeutic agents and bioactive agents have been described above herein. In an aspect, the at least one therapeutic agent and/or the at least one bioactive agent is associated with the outer layer and/or the inner layer of the layered wall of the flexible tubular structure. In an aspect, the at least one therapeutic agent and/or the at least one bioactive agent is associated with the internal space of the layered wall of the flexible tubular structure. In an aspect, the at least one therapeutic agent and/or the at least one bioactive agent is associated with the at least one anchor structure. In an aspect, the at least one therapeutic agent and/or the at least one bioactive agent is included in a degradable coating or matrix associated with outer layer and/or the inner layer of the flexible tubular structure. In an aspect, the at least one therapeutic agent and/or the at least one bioactive agent is included in a degradable coating or matrix associated with the internal space of the layered wall of the flexible tubular structure.

Gastrointestinal device 2700 includes at least one anchor structure including one or more gastric wall-engaging components configured to engage a wall of the gastrointestinal tract of a subject. In an aspect, the at least one anchor structure is attached to the proximal end of the flexible tubular structure. In an aspect, the at least one anchor structure is attached to the distal end of the flexible tubular structure. In an aspect, the at least one anchor structure is incorporated into the flexible tubular structure. In an aspect, the at least one anchor structure includes one or more gastric wall-engaging components positioned along at least a portion of the flexible tubular structure. In an aspect, the one or more gastric wall-engaging components include one or more barbs or one or more hooks. In an aspect, the one or more gastric wall-engaging components include an adhesive or an adherent. In an aspect, the at least one anchor structure is inflatable. In an aspect, the at least one anchor structure is expandable. Non-limiting examples of anchor structures have been described above herein.

Figure 33:
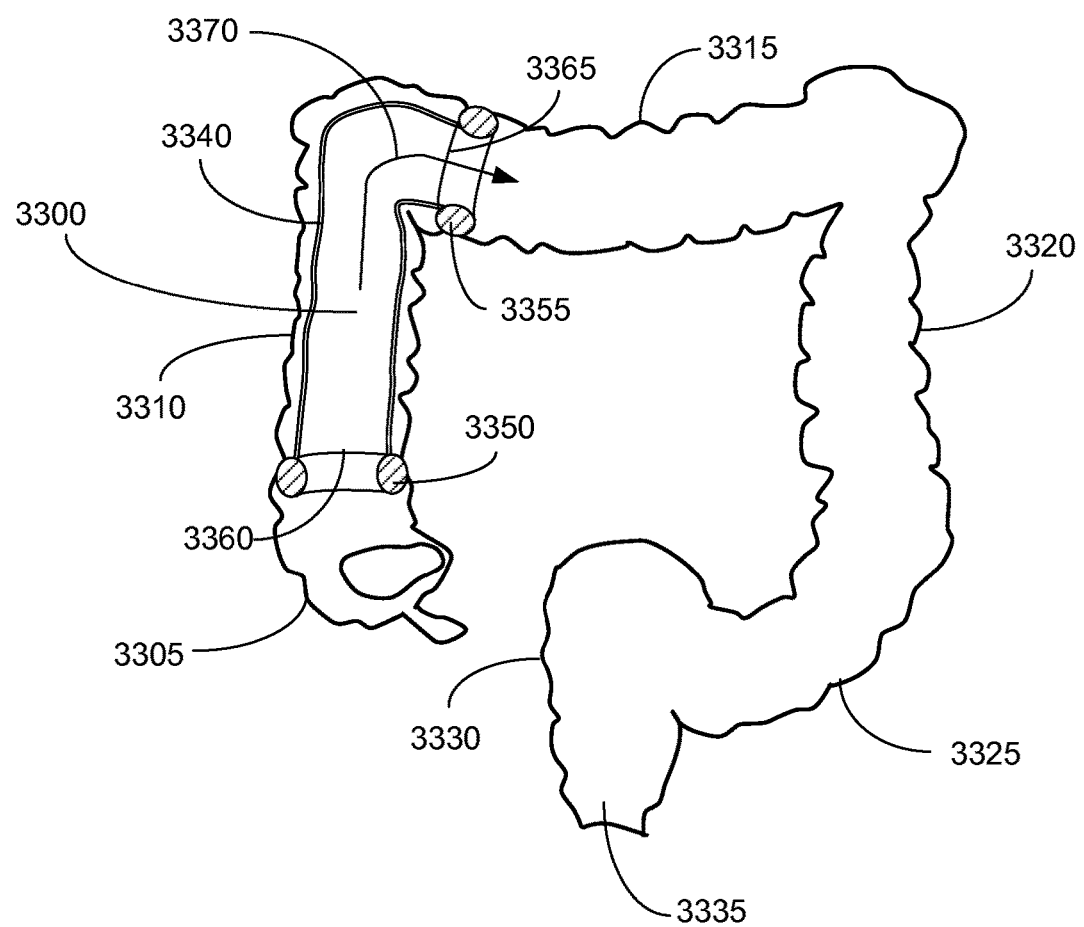
FIG. 33 is a schematic of a gastrointestinal device positioned in the large intestine.

FIG. 33 illustrates an example of a gastrointestinal device 3300 positioned in the lower gastrointestinal tract of a subject. During digestion, ingested material leaves the stomach and is further processed in the small intestine. From the small intestine, the ingested material enters the large intestine, passing through the cecum 3305, ascending colon 3310, transverse colon 3315, descending colon 3320, sigmoid colon 3325, rectum 3330, and out the anus 3335. Gastrointestinal device 3300 includes flexible tubular structure 3340 and at least one anchor structure 3350. In this embodiment, a first anchor structure 3350 is engaging the wall of the ascending colon 3310 and a second anchor structure 3355 is engaging the wall of the transverse colon. In an embodiment, flexible tubular structure 3340 includes an inner surface and an outer surface, a plurality of at least one type of commensal microbe associated with at least a portion of at least one of the inner surface and the outer surface, and a proximal end 3360 and a distal end 3365 forming a flow conduit 3370 through the flexible tubular structure 3340.

In an embodiment, flexible tubular structure 3340 includes a layered wall, a plurality of at least one type of commensal microbe encased in the layered wall, the layered wall configured to allow an interaction between the plurality of the at least one type of commensal microbe and an ingested product within the flexible tubular structure.

In an embodiment, flexible tubular structure 3340 includes an inner surface and an outer surface, at least one microbe-promoting agent associated with at least one of the inner surface and the outer surface, the at least one microbe-promoting agent configured to promote at least one of attraction, colonization, and growth of at least one type of commensal microbe.

In an embodiment, flexible tubular structure 3340 includes a layered wall, a least one microbe-promoting agent encased in the layered wall, the at least one microbe-promoting agent configured to promote at least one of attraction, colonization, and growth of at least one type of commensal microbe.

Methods

FIGS. 34-38 show block flow diagrams describing aspects of a method for generating a gastrointestinal device including a plurality of at least one type of commensal microbe. FIG. 34 shows a block diagram of a method, the method including in block 3400 obtaining a gastrointestinal device, the gastrointestinal device including a flexible tubular structure including an inner surface and an outer surface; a proximal end and an distal end, the proximal end and the distal end forming a flow conduit through the flexible tubular structure; and at least one anchor structure including one or more gastric wall-engaging components configured to engage a wall of the gastrointestinal tract of a subject; and in block 3410, distributing on at least a portion of at least one of the inner surface and the outer surface of the flexible tubular structure a plurality of at least one type of commensal microbe.

FIG. 35 shows further aspects of a method of generating a gastrointestinal device such as described in FIG. 34. The method includes obtaining a gastrointestinal device. In an aspect, the method includes in block 3500 manufacturing the gastrointestinal device. For example, the method can include manufacturing a sleeve, liner, or stent sized for placement in the gastrointestinal tract, including the esophagus. See, e.g., U.S. Pat. No. 7,025,791 to Levine et al. titled "Bariatric Sleeve;" U.S. Pat. No. 7,037,344 to Kagan et al. titled "Apparatus and Methods for Treatment of Morbid Obesity;" U.S. Pat. No. 7,976,488 to Levine & Melanson titled "Gastrointestinal Anchor Compliance;" U.S. Patent Application No. 2012/0158026 to Behan titled "Gastrointestinal Implant Device;" U.S. Patent Application No. 2021/0184893 to Thompson et al. titled "Anchors and Methods for Intestinal Bypass Sleeves;" U.S. Patent Application No. 2013/0281911 to Babkes et al. titled "Anchored Non-Piercing Duodenal Sleeve and Delivery Systems;" U.S. Patent Application No. 2013/0331759 to Neisz et al. titled "Devices and Methods for Gastrointestinal Bypass;" U.S. Patent Application No. 2014/0012178 to Chin titled "Systems and Methods for Bariatric Therapy;" all of which are incorporated herein by reference. In an aspect, the method includes using a commercially available gastrointestinal device. For example, the method can include using a commercially available intestinal sleeve, e.g., the EndoBarrier® gastrointestinal liner from GI Dynamics, Inc., Lexington, Mass. See, e.g., Rohde et al. (2013) *BMJ Open* 3:e003417, which is incorporated herein by reference.

The method further includes distributing on at least a portion of at least one of the inner surface and the outer surface of the flexible tubular structure a plurality of at least one type of commensal microbe. In an aspect, the flexible tubular structure is formed from a semi-permeable material, as shown in block 3510. In an aspect, the flexible tubular structure is formed from a substantially impermeable material, as shown in block 3520. Non-limiting examples of flexible tubular structures formed from semi-permeable material or substantially impermeable material have been described above herein. In an aspect, the flexible tubular structure is noncontiguous, as shown in block 3530.

In an aspect, the method includes coating the at least a portion of the at least one of the inner surface and the outer surface of the flexible tubular structure with the plurality of the at least one type of commensal microbe, as shown in block 3540. For example, the method can include coating at least a portion of the inner surface of the flexible tubular structure with a plurality of at least one type of commensal microbe. For example, the method can include coating at least a portion of the outer surface of the flexible tubular structure with the plurality of the at least one type of commensal microbe. For example, the method can include coating at least a portion of the inner surface and at least a portion of the outer surface of the flexible tubular structure with the plurality of the at least one type of commensal microbe. In an aspect, coating includes spraying the at least a portion of the at least one of the inner surface and the outer surface of the flexible tubular structure with a composition including the plurality of the at least one type of commensal microbe. In an aspect, coating includes dipping the at least a portion of the at least one of the inner surface and the outer surface of the flexible tubular structure into a composition including the plurality of the at least one type of commensal microbe. In an aspect, coating includes spreading a composition including the plurality of the at least one type of microbe onto the at least a portion of the at least one of the inner surface and the outer surface of the flexible tubular structure.

In an aspect, a method of generating a gastrointestinal device such as shown in FIG. 34 includes distributing on the at least a portion of the at least one of the inner surface and the outer surface of the flexible tubular structure the plurality of the at least one type of commensal microbe in a coating material, as shown in block 3550. In an aspect, the coating material includes at least one of a degradable coating material, a matrix coating material, a fibrous coating material, a hydrogel coating material, or a mucus coating material, as shown in block 3560. Non-limiting examples of coating materials have been described above herein.

In an aspect, the plurality of the at least one type of commensal microbe and the coating material are applied to at least one of the inner surface and the outer surface of the flexible tubular structure simultaneously. In an aspect, the plurality of the at least one type of commensal microbe and the coating material are applied to at least one of the inner surface and the outer surface of the flexible tubular structure simultaneously from a common source, e.g., a reservoir containing the combination. In an aspect, the plurality of the at least one type of commensal microbe and the coating material are applied to at least one of the inner surface and the outer surface of the flexible tubular structure simultaneously from different sources, e.g., one source, e.g., a first reservoir, providing the plurality of the at least one type of commensal microbe and a second source, e.g., a second reservoir, providing the coating material. In an aspect, the plurality of the at least one type of commensal microbe and the coating material are applied to at least one of the inner surface and the outer surface of the flexible tubular structure sequentially. For example, the plurality of the at least one type of commensal microbe can be applied first to at least one of the inner surface and the outer surface of the flexible tubular structure followed by application of the coating material. For example, the plurality of the at least one type of commensal microbe can be applied to at least one of the inner surface and the outer surface of the flexible tubular structure to which a coating material has already been applied.

In an aspect, the method includes distributing on the at least a portion of the at least one of the inner surface and the outer surface of the flexible tubular structure the plurality of the at least one type of commensal microbe in a stimulus-responsive coating material, as shown in block 3570. In an aspect, the stimulus-responsive coating material includes at least one of a time-responsive coating material, a moisture-responsive coating material, a temperature-responsive coating material, a pH-responsive coating material, or a chemical-responsive coating material, as shown in block 3580.

In an aspect, the method further includes coating at least a portion of at least one of the inner surface and the outer surface of the flexible tubular structure with a coating material, as shown in block 3590. In an aspect, the coating material includes a degradable coating material, a matrix coating material, a fibrous coating material, a hydrogel coating material, or a mucus coating material. In an aspect, the method includes coating the at least a portion of the at least one of the inner surface and the outer surface of the flexible tubular structure with a coating material, and adding the plurality of the at least one type of commensal microbe to the coated portion of the at one of the inner surface and the outer surface of the flexible tubular structure. For example, at least a portion of the inner surface and/or outer surface of the flexible tubular structure can be coated with a coating material to which at least one type of commensal microbe is capable of binding to. In an aspect, the method includes coating at least a portion of at least one of the inner surface and the outer surface of the flexible tubular structure with a non-selective binding material, e.g., an adhesive, an absorbent, an adsorbent, a gel, a matrix, or a biopolymer. In an aspect, the method includes coating at least a portion of at least one of the inner surface and the outer surface of the flexible tubular structure with a selective-binding agent, e.g., an antibody, an aptamer, an oligonucleotide, ligand, a receptor, or a lectin. In an aspect, the method includes distributing a plurality of at least one type of commensal microbe on at least a portion of at least one of the inner surface and the outer surface of a flexible tubular structure coated with a coating material.

FIG. 36 illustrates further aspects of a method such as shown in FIG. 34. In an aspect, the method includes binding on the at least a portion of the at least one of the inner surface and the outer surface of the flexible tubular structure the plurality of the at least one type of commensal microbe, as shown in block 3600. In an aspect, the method includes binding on the at least a portion of the at least one of the inner surface and the outer surface of the flexible tubular structure the plurality of the at least one type of commensal microbe with at least one selective binding agent or non-selective binding agent, as shown in block 3610. In an aspect, the at least one selective binding agent includes an antibody, a protein, a peptide, a DNA fragment, an RNA fragment, a lectin, or an aptamer, as shown in block 3620. For example, the method can include binding the plurality of the at least one type of commensal microbe to an antibody cross-linked to the flexible tubular structure, the antibody configured to recognize and bind a component of the surface of the at least one type of commensal microbe. In an aspect, the at least one non-selective binding agent includes at least one of an adhesive, an absorbent, an adsorbent, a gel, or a matrix, as shown in block 3630.

In an aspect, the method includes impregnating the at least a portion of the at least one of the inner surface and the outer surface of the flexible tubular structure with the plurality of the at least one type of commensal microbe, as shown in block 3640. For example, the method can include impregnating the inner and/or outer surface of a porous or fibrous material forming the flexible tubular structure with the plurality of the at least one type of commensal microbe. In an aspect, the method includes embedding into the at least a portion of the at least one of the inner surface and the outer surface of the flexible tubular structure the plurality of the at least one type of commensal microbe, as shown in block 3650. In an aspect, the method includes adsorbing, absorbing, covalently binding, or non-covalently binding to the at least a portion of the at least one of the inner surface and the outer surface of the flexible tubular structure the plurality of the at least one type of commensal microbe, as shown in block 3660. In an aspect, the method includes embedding the plurality of the at least one type of commensal microbe into the flexible tubular structure at the time of manufacture, as shown in block 3670. For example, the plurality of the at least one type of commensal microbe can be incorporated into a polymer during a liquid or gel phase prior to forming a solid phase.

FIG. 37 shows further aspects of a method for generating a gastrointestinal device such as shown in FIG. 34. The method includes distributing on the at least a portion of the at least one of the inner surface and the outer surface of the flexible tubular structure the plurality of the at least one type of commensal microbe. In an aspect, the plurality of the at least one type of commensal microbe includes at least one type of gut microbe, as shown in block 3700. In an aspect, the at least one type of gut microbe includes at least one type of commensal gut microbe. For example, the method can include coating the flexible tubular structure with a plurality of at least one type of Firmicutes (e.g., one or more representatives of *Lactobacillus*), Bacteroidetes, Actinobacteria (e.g., one or more representatives of *Bifidobacterium*) and/or Proteobacteria. Non-limiting examples of gut microbes have been described above herein.

In an aspect, the plurality of the at least one type of commensal microbe includes at least one type of genetically modified microbe, as shown in block 3710. For example, the method can include coating the flexible tubular structure with a plurality of a type of microbe genetically modified to produce a specific digestive enzyme or therapeutic agent.

In an aspect, the plurality of the at least one type of commensal microbe includes at least one type of commensal microbe from a fecal sample, as shown in block 3720. For example, the method can include distributing on at least one surface of the flexible tubular structure at least one type of commensal microbe from a fecal sample derived from the subject, a relative, or a healthy donor.

In an aspect, the plurality of the at least one type of commensal microbe includes at least part of a gut microbiota, as shown in block 3730. In an aspect, the at least part of the gut microbiota includes at least part of a gut microbiota of the subject, as shown in block 3740. In an aspect, the at least part of the gut microbiota includes at least part of a gut microbiota of one or more other individuals, as shown in block 3750. In an aspect, the at least part of the gut microbiota includes at least part of a healthy gut microbiota, a preferred gut microbiota, or a theoretical gut microbiota, as shown in block 3760. In an aspect, the method includes preparing the at least part of the gut microbiota from a fecal sample, as shown in block 3770. In an aspect, the method includes preparing the at least part of the gut microbiota from in vitro culture of one or more types of gut microbes, as shown in block 3780

FIG. 38 shows further aspects of a method for generating a gastrointestinal device such as shown in FIG. 34. The method includes distributing on the at least a portion of the at least one of the inner surface and the outer surface of the flexible tubular structure a plurality of at least one type of commensal microbe. In an aspect, the plurality of the at least one type of commensal microbe includes a phylogentically diverse mini-microbiota, as shown in block 3800. In an aspect, the plurality of the at least one type of commensal microbe includes a plurality of at least one type of probiotic, as shown in block 3810. Non-limiting examples of probiotics have been described above herein. In an aspect, the at least one type of commensal microbe is beneficial to the subject, as shown in block 3820. In an aspect, the at least one type of commensal microbe is beneficial to at least one of the immune system of the subject, a dietary condition of the subject, or a medical condition of the subject, as shown in block 3830. For example, the method can include distributing on at least one surface of the flexible tubular structure a plurality of at least one type of genetically modified microbe configured to secrete a digestive enzyme or therapeutic agent beneficial to a condition of the subject. In an aspect, the at least one type of commensal microbe is beneficial to the subject with a *Clostridium difficile* infection. In an aspect, the at least one type of commensal microbe is beneficial to the subject with Crohn's disease.

In an aspect, the method further includes distributing on at least a portion of the at least one of the inner surface and the outer surface of the flexible tubular structure at least one of a prebiotic agent, a therapeutic agent, or a bioactive agent, as shown in block 3840. For example, the method can include distributing on at least one surface of the flexible tubular structure an oligosaccharide prebiotic agent. For example, the method can include distributing on at least one surface of the flexible tubular structure an antibiotic. For example, the method can include distributing on at least one surface of the flexible tubular structure a digestive enzyme.

Non-limiting example of prebiotic agents, therapeutic agents, and bioactive agents have been described above herein.

In an aspect, the method includes distributing on at least a portion of the inner surface of the flexible tubular structure at least one of a prebiotic agent, a therapeutic agent, or a bioactive agent. In an aspect, the method includes distributing on at least a portion of the outer surface of the flexible tubular structure at least one of a prebiotic agent, a therapeutic agent, or a bioactive agent. In an aspect, the method includes distributing on at least a portion of both the inner surface and the outer surface of the flexible tubular structure with at least one of a prebiotic agent, a therapeutic agent, or a bioactive agent. In an aspect, the method includes distributing on at least a portion of at least one of the inner surface and the outer surface of the flexible tubular structure at least one first prebiotic agent, therapeutic agent, or bioactive agent and at least one second prebiotic agent, therapeutic agent, or bioactive agent. In an aspect, the method includes distributing on at least a portion of at least one of the inner surface and the outer surface of the flexible tubular structure at least one of a prebiotic agent, a therapeutic agent, or a bioactive agent in a coating material. In an aspect, the coating material includes at least one of a degradable coating material, a matrix coating material, a fibrous coating material, a hydrogel coating material, a mucus coating material, or a stimulus-responsive coating material.

FIGS. 39-43 show block flow diagrams of a method for generating a gastrointestinal device including at least one microbe-promoting agent. FIG. 39 shows a flow diagram of a method including obtaining a gastrointestinal device, the gastrointestinal device including a flexible tubular structure including an inner surface and an outer surface; and a proximal end and a distal end, the proximal end and the distal end forming a flow conduit through the flexible tubular structure; and at least one anchor structure including one or more gastric wall-engaging components configured to engage a wall of the gastrointestinal tract of a subject, in block 3900; and distributing on at least one of the inner surface and the outer surface of the flexible tubular structure at least one microbe-promoting agent, the at least one microbe-promoting agent configured to promote at least one of attraction, colonization, and growth of at least one type of commensal microbe, in block 3910.

FIG. 40 shows further aspects of a method of generating a gastrointestinal device with at least one microbe-promoting agent such as described in FIG. 39. The method includes obtaining a gastrointestinal device. In an aspect, the method includes manufacturing the gastrointestinal device, as shown in block 4000. In an aspect, the method includes using a commercially available gastrointestinal device.

The method further includes distributing on at least one of the inner surface and the outer surface of the flexible tubular structure at least one microbe-promoting agent. In an aspect, the flexible tubular structure is formed from a semi-permeable material, as shown in block 4010. In an aspect, the flexible tubular structure is formed from a substantially impermeable material, as shown in block 4020. Non-limiting examples of flexible tubular structures formed from semi-permeable material or substantially impermeable material have been described above herein. In an aspect, the flexible tubular structure is noncontiguous, as shown in block 4030.

In an aspect, the method includes coating the at least one of the inner surface and the outer surface of the flexible tubular structure with the at least one microbe-promoting agent, as shown in block 4040. For example, the method can include coating at least a portion of the inner surface of the flexible tubular structure with at least one microbe-promoting agent. For example, the method can include coating at least a portion of the outer surface of the flexible tubular structure with at least one microbe-promoting agent. For example, the method can include coating at least a portion of the inner surface and at least a portion of the outer surface of the flexible tubular structure with at least one microbe-promoting agent. In an aspect, coating includes spraying the at least one of the inner surface and the outer surface of the flexible tubular structure with a composition including the at least one microbe-promoting agent. In an aspect, coating includes dipping the at least one of the inner surface and the outer surface of the flexible tubular structure into a composition including the at least one microbe-promoting agent. In an aspect, coating includes spreading a composition including the at least one microbe-promoting agent onto at least one of the inner surface and the outer surface of the flexible tubular structure.

In an aspect, the method includes distributing on the at least one of the inner surface and the outer surface of the flexible tubular structure the at least one microbe-promoting agent in a coating material, as shown in block 4050. In an aspect, the coating material includes at least one of a degradable coating material, a matrix coating material, a fibrous coating material, a hydrogel coating material, or a mucus coating material, as shown in block 4060.

In an aspect, the at least one microbe-promoting agent and the coating material are applied to at least one of the inner surface and the outer surface of the flexible tubular structure simultaneously. In an aspect, the at least one microbe-promoting agent and the coating material are applied to at least one of the inner surface and the outer surface of the flexible tubular structure simultaneously from a common source, e.g., a reservoir containing the combination. In an aspect, the at least one microbe-promoting agent and the coating material are applied to at least one of the inner surface and the outer surface of the flexible tubular structure simultaneously from different sources, e.g., one source, e.g., a first reservoir, providing the plurality of the at least one type of commensal microbe and a second source, e.g., a second reservoir, providing the coating material. In an aspect, the at least one microbe-promoting agent and the coating material are applied to at least one of the inner surface and the outer surface of the flexible tubular structure sequentially. For example, the at least one microbe-promoting agent can be applied first to at least one of the inner surface and the outer surface of the flexible tubular structure followed by application of the coating material. For example, the at least one microbe-promoting agent can be applied to at least one of the inner surface and the outer surface of the flexible tubular structure to which a coating material has already been applied.

In an aspect, the method includes distributing on the at least one of the inner surface and the outer surface of the flexible tubular structure the at least one microbe-promoting agent in a stimulus-responsive coating material, as shown in block 4070. In an aspect, the stimulus-responsive coating material includes at least one of a time-responsive coating material, a moisture-responsive coating material, a temperature-responsive coating material, a pH-responsive coating material, or a chemical-responsive coating material, as shown in block 4080.

In an aspect, the method further includes coating at least a portion of at least one of the inner surface and the outer surface of the flexible tubular structure with a coating material. In an aspect, the coating material includes a degradable coating material, a matrix coating material, a fibrous coating material, a hydrogel coating material, or a mucus coating material. In an aspect, the method includes coating the at least a portion of the at least one of the inner surface and the outer surface of the flexible tubular structure with a coating material, and adding the at least one microbe-promoting agent to the coated portion of the at one of the inner surface and the outer surface of the flexible tubular structure.

FIG. 41 illustrates further aspects of a method such as shown in FIG. 39. In an aspect, the method includes binding on the at least one of the inner surface and the outer surface of the flexible tubular structure the at least one microbe-promoting agent, as shown in block 4100. In an aspect, the method includes binding on the at least one of the inner surface and the outer surface of the flexible tubular structure the at least one microbe-promoting agent with at least one non-selective binding agent or selective binding agent, as shown in block 4110. In an aspect, the at least one selective binding agent includes an antibody, a protein, a peptide, a DNA fragment, an RNA fragment, a lectin, or an aptamer, as shown in block 4120. For example, the method can include binding the at least one microbe-promoting agent to an antibody cross-linked to the flexible tubular structure, the antibody configured to recognize and bind the at least one microbe-promoting agent. In an aspect, the at least one non-selective binding agent includes at least one of an adhesive, an absorbent, an adsorbent, a gel, or a matrix, as shown in block 4130.

In an aspect, the method includes impregnating the at least one of the inner surface and the outer surface of the flexible tubular structure with the at least one microbe-promoting agent, as shown in block 4140. For example, the method can include impregnating the inner and/or outer surface of a porous or fibrous material forming the flexible tubular structure with the at least one microbe-promoting agent. In an aspect, the method includes embedding into the at least one of the inner surface and the outer surface of the flexible tubular structure the at least one microbe-promoting agent, as shown in block 4150. In an aspect, the method includes adsorbing, absorbing, covalently binding, or non-covalently binding onto the at least one of the inner surface and the outer surface of the flexible tubular structure the at least one microbe-promoting agent, as shown in block 4160. In an aspect, the method includes embedding the at least one microbe-promoting agent into the flexible tubular structure at the time of manufacture, as shown in block 4170. For example, the at least one microbe-promoting agent can be incorporated into a polymer during a liquid or gel phase prior to forming a solid phase.

FIG. 42 shows further aspects of a method for generating a gastrointestinal device such as shown in FIG. 39. The method includes distributing on the at least one of the inner surface and the outer surface of the flexible tubular structure at least one microbe-promoting agent, the at least one microbe-promoting agent configured to promote at least one of attraction, colonization, and growth of at least one type of commensal microbe. In an aspect, the at least one microbe-promoting agent is configured to promote at least one of attraction, colonization, and growth of at least one type of commensal gut microbe, as shown in block 4200. In an aspect, the at least one microbe-promoting agent is configured to promote at least one of attraction, colonization, and growth of at least part of a gut microbiota, as shown in block 4210. In an aspect, the at least one microbe-promoting agent is configured to promote at least one of attraction, colonization, and growth of at least one type of endogenous commensal microbe, as shown in block 4220. In an aspect, the at least one microbe-promoting agent is configured to promote at least one of attraction, colonization, and growth of at least one type of administered commensal microbe, as shown in block 4230. In an aspect, the at least one microbe-promoting agent is configured to promote at least one of attraction, colonization, and growth of at least one type of commensal microbe derived from a fecal sample, as shown in block 4240. In an aspect, the at least one microbe-promoting agent is configured to promote at least one of attraction, colonization, and growth of at least one type of genetically engineered microbe, as shown in block 4250. In an aspect, the at least one microbe-promoting agent is configured to promote at least one of attraction, colonization, and growth of at least one type of commensal microbe derived from in vitro culture, as shown in block 4260. In an aspect, the at least one microbe-promoting agent is configured to promote at least one of attraction, colonization, and growth of at least one type of probiotic, as shown in block 4270. In an aspect, the at least one microbe-promoting agent is configured to promote at least one of attraction, colonization, and growth of a phylogenetically diverse mini-microbiota, as shown in block 4280.

FIG. 43 shows further aspects of a method for generating a gastrointestinal device such as shown in FIG. 39. The method includes distributing on at least one of the inner surface and the outer surface of the flexible tubular structure at least one microbe-promoting agent. In an aspect, the at least one microbe-promoting agent is configured to promote at least one of attraction, colonization, and growth of at least one type of commensal microbe beneficial to the subject, as shown in block 4300. In an aspect, the at least one microbe-promoting agent is configured to promote at least one of attraction, colonization, and growth of at least one type of commensal microbe beneficial to at least one of the immune system of the subject, a dietary condition of the subject, or a medical condition of the subject, as shown in block 4310. In an aspect, the at least one microbe-promoting agent is configured to promote at least one of attraction, colonization, and growth of at least one type of commensal microbe beneficial to the subject with a *Clostridium difficile* infection. In an aspect, the at least one microbe-promoting agent is configured to promote at least one of attraction, colonization, and growth of at least one type of commensal microbe beneficial to the subject with Crohn's disease.

In an aspect, the at least one microbe-promoting agent is configured to promote formation of a microbiome, as shown in block 4320. For example, the at least one microbe-promoting agent can be configured to promote formation of a healthy microbiome or preferred microbiome. The microbiome can include the environment as well as microbes associated with the environment. For example, the at least one microbe-promoting agent directly promote attraction, colonization, and/or growth of microbes associated with a microbiome. For example, the at least one microbe-promoting agent can indirectly promote attraction, colonization, and/or growth of microbes associated with a microbiome by altering the environment, e.g., the pH of the environment.

In an aspect, the at least one microbe-promoting agent includes at least one prebiotic agent, as shown in block 4330. For example, the at least one prebiotic agent can include inulin. Non-limiting examples of prebiotic agents have been described above herein. In an aspect, the at least one microbe-promoting agent includes a mucus, as shown in block 4340. For example, the at least one microbe-promoting agent can include natural mucus. For example, the at least one microbe-promoting agent can include synthetic mucus. Non-limiting aspects of mucus have been described above herein. In an aspect, the at least one microbe-promoting agent includes a binding agent, as shown in block 4350. For example, the at least one microbe-promoting agent can include an antibody or an aptamer that recognizes and binds at least one type of commensal microbe. Non-limiting examples of binding agents have been described above herein. In an aspect, the at least one microbe-promoting agent includes at least one lectin, as shown in block 4360. For example, the at least one microbe-promoting agent can include mannan-binding lectin for interaction with D-mannose and/or L-fucose residues on microbes, including intestinal pathogens such as *Salmonella*. Non-limiting examples of lectins have been described above herein.

In an aspect, the method further includes distributing on at least one first portion of the flexible tubular structure at least one first microbe-promoting agent and distributing on at least one second portion of the flexible tubular structure at least one second microbe-promoting agent, as shown in block 4370.

In an aspect, the method further includes distributing on at least one of the inner surface and the outer surface of the flexible tubular structure at least one therapeutic agent, as shown in block 4380. For example, the method can include distributing on at least one surface of the flexible tubular structure an antibiotic or anti-inflammatory agent. Non-limiting example of therapeutic agents have been described above herein. In an aspect, the method includes distributing on at least a portion of the inner surface of the flexible tubular structure at least one therapeutic agent. In an aspect, the method includes distributing on at least a portion of the outer surface of the flexible tubular structure at least one therapeutic agent. In an aspect, the method includes distributing on at least a portion of both the inner surface and the outer surface of the flexible tubular structure with at least one therapeutic agent. In an aspect, the method includes distributing on at least a portion of at least one of the inner surface and the outer surface of the flexible tubular structure at least one first therapeutic agent and at least one second therapeutic agent. In an aspect, the method includes distributing on at least a portion of at least one of the inner surface and the outer surface of the flexible tubular structure at least one therapeutic agent in a coating material. In an aspect, the coating material includes at least one of a degradable coating material, a matrix coating material, a fibrous coating material, a hydrogel coating material, a mucus coating material, or a stimulus-responsive coating material.

In an aspect, the method further includes distributing on at least one of the inner surface and the outer surface of the flexible tubular structure at least one bioactive agent, as shown in block 4390. For example, the method can include distributing on at least one surface of the flexible tubular structure a digestive enzyme. Non-limiting examples of bioactive agents have been described above herein. In an aspect, the method includes distributing on at least a portion of the inner surface of the flexible tubular structure at least one bioactive agent. In an aspect, the method includes distributing on at least a portion of the outer surface of the flexible tubular structure at least one bioactive agent. In an aspect, the method includes distributing on at least a portion of both the inner surface and the outer surface of the flexible tubular structure with at least one bioactive agent. In an aspect, the method includes distributing on at least a portion of at least one of the inner surface and the outer surface of the flexible tubular structure at least one first bioactive agent and at least one second bioactive agent. In an aspect, the method includes distributing on at least a portion of at least one of the inner surface and the outer surface of the flexible tubular structure at least one bioactive agent in a coating material. In an aspect, the coating material includes at least one of a degradable coating material, a matrix coating material, a fibrous coating material, a hydrogel coating material, a mucus coating material, or a stimulus-responsive coating material.

FIGS. 44-48 show block flow diagrams of a method for generating a gastrointestinal device with a layered wall encasing a plurality of at least one type of commensal microbe. FIG. 44 shows a flow diagram of a method including obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place, in block 4400; distributing on one surface of the first material a plurality of at least one type of commensal microbe, in block 4410; and applying a second material over the plurality of the at least one type of commensal microbe to form a layered wall, the layered wall allowing an interaction between the plurality of the at least one type of commensal microbe and an ingested product within the flexible tubular structure, in block 4420.

FIG. 45 shows further aspects of a method of generating a gastrointestinal device including a layered wall. The method includes obtaining a gastrointestinal device. In an aspect, the method includes manufacturing the gastrointestinal device, as shown in block 4500. For example, the method can include manufacturing a bariatric sleeve such as described in U.S. Patent Application No. 2014/0012178 to Chin titled "Systems and Methods for Bariatric Therapy," which is incorporated herein by reference. In an aspect, the method includes using a commercially available gastrointestinal device.

The method includes distributing on one surface of the first material a plurality of at least one type of commensal microbe and applying a second material over the plurality of the at least one type of commensal microbe. In an aspect, at least one of the first material and the second material includes a semi-permeable material, as shown in block 4510. In an aspect, at least one of the first material and the second material includes a selectively permeable material. In an aspect, the selectively permeable material is selectively permeable based on size, hydrophobicity, or charge. Non-limiting examples of semi-permeable materials have been described above herein. In an aspect, the first material includes a first semi-permeable material and the second material includes a second semi-permeable material, as shown in block 4520. In an aspect, the first semi-permeable material differs from the second semi-permeable material, as shown in block 4530. For example, the first semi-permeable material can differ from the second semi-permeable material based on selectivity to size, hydrophobicity, or charge.

In an aspect, the method includes distributing on an inner surface of the first material the plurality of the at least one type of commensal microbe, the inner surface facing the flow conduit through the flexible tubular structure, as shown in block 4540. In an aspect, the method includes distributing on an outer surface of the first material the plurality of the at least one type of commensal microbe, the outer surface facing the wall of the gastrointestinal tract, as shown in block 4550.

The method includes distributing on one surface of the first material a plurality of at least one type of commensal microbe. In an aspect, the method includes coating the one surface of the first material with the plurality of the at least one type of commensal microbe, as shown in block 4560. In an aspect, coating includes spraying, dipping, or spreading a composition including the plurality of the at least one type of commensal microbe on the one surface of the first material. In an aspect, the method includes distributing on the one surface of the first material the plurality of the at least one type of commensal microbe in a coating material, as shown in block 4570. In an aspect, the coating material includes at least one of a degradable coating material, a matrix coating material, a fibrous coating material, a porous coating material, a gel coating material, or a mucus coating material, as shown in block 4580. In an aspect, the method includes distributing on the one surface of the first material the plurality of the at least one type of commensal microbe in a stimulus-responsive coating material, as shown in block 4590. In an aspect, the stimulus-responsive coating material includes at least one of a time-responsive coating material, a moisture-responsive coating material, a temperature-responsive coating material, a pH-responsive coating material, or a chemical-responsive coating material, as shown in block 4595.

FIG. 46 illustrates further aspects of a method such as shown in FIG. 44. In an aspect, the method includes in block 4600 binding to the one surface of the first material the plurality of the at least one type of commensal microbe. In an aspect, the method includes in block 4610 binding to the one surface of the first material the plurality of the at least one type of commensal microbe with at least one non-selective binding agent or selective binding agent. In an aspect, the at least one selective binding agent includes at least one of an antibody, a protein, a peptide, a DNA fragment, an RNA fragment, a lectin, or an aptamer, as shown in block 4620. In an aspect, the at least one non-selective binding agent includes at least one of an adhesive, an absorbent, an adsorbent, a gel, or a matrix, as shown in block 4630. Non-limiting examples of selective binding agents and non-selective binding agents have been described above herein.

In an aspect, the method includes in block 4640 impregnating into the one surface of the first material the plurality of the at least one type of commensal microbe. In an aspect, the method includes in block 4650 embedding into the one surface of the first material the plurality of the at least one type of commensal microbe. In an aspect, the method includes in block 4660 adsorbing, absorbing, covalently binding, or non-covalently binding onto the one surface of the first material the plurality of the at least one type of commensal microbe. In an aspect, the method further includes in block 4670 embedding the plurality of the at least one type of commensal microbe into the flexible tubular structure at the time of manufacture.

FIG. 47 shows further aspects of a method such as shown in FIG. 44. The method includes distributing on one surface of the first material a plurality of at least one type of commensal microbe. In an aspect, the plurality of the at least one type of commensal microbe includes at least one type of gut microbe, as shown in block 4700. In an aspect, the plurality of the at least one type of commensal microbe includes at least one type of genetically modified microbe, as shown in block 4710. In an aspect, the plurality of the at least one type of commensal microbe is derived from a fecal sample, as shown in block 4720. In an aspect, the plurality of the at least one type of commensal microbe includes at least part of a gut microbiota, as shown in block 4730. In an aspect, the at least part of the gut microbiota includes at least part of a gut microbiota from at least one of the subject or one or more other individuals, as shown in block 4740. In an aspect, the at least part of the gut microbiota includes at least part of a healthy gut microbiota, a preferred gut microbiota, or a theoretical gut microbiota, as shown in block 4750. In an aspect, the method includes preparing the at least part of the gut microbiota from a fecal sample, as shown in block 4760. In an aspect, the method includes preparing the at least a part of the gut microbiota from in vitro culture of one or more types of gut microbes, as shown in block 4770. In an aspect, the plurality of the at least one type of commensal microbe includes a phylogenetically diverse mini-microbiota, as shown in block 4780. In an aspect, the plurality of the at least one type of commensal microbe includes a plurality of at least one type of probiotic, as shown in block 4790.

FIG. 48 shows further aspects of a method such as shown in FIG. 44. The method includes distributing on one surface of the first material a plurality of at least one type of commensal microbe. In an aspect, the at least one type of commensal microbe is beneficial to the subject, as shown in block 4800. In an aspect, the at least one type of commensal microbe is beneficial to at least one of the immune system of the subject, a dietary condition of the subject, or a medical condition of the subject, as shown in block 4810.

In an aspect, the method further includes distributing on a surface of the first material at least one of a prebiotic agent, a therapeutic agent, or a bioactive agent, as shown in block 4820. Non-limiting examples of prebiotic agents, therapeutic agents, and bioactive agents have been described above herein.

The method further includes applying a second material over the plurality of the at least one type of commensal microbe to form a layered wall, the layered wall allowing an interaction between the plurality of the at least one type of commensal microbe and an ingested product within the flexible tubular structure. In an aspect, the method includes applying a second material substantially identical to the first material, as shown in block 4830. In an aspect, the method includes applying a second material with a permeability property that differs from a permeability property of the first material, as shown in block 4840. In an aspect, the permeability property includes at least one of a sized-based permeability property, a charge-based permeability property, a pH-based permeability property, or a hydrophobicity-based permeability property, as shown in block 4850.

In an aspect, the method further includes attaching the first material including the plurality of the at least one type of commensal microbe to the second material. In an aspect, the method includes adhering (e.g., gluing) the first material to the second material. In an aspect, the method includes stapling the first material to the second material. In an aspect, the method includes stitching the first material to the second material. In an aspect, the method includes fusing the first material to the second material. For example, the first material including the plurality of the at least one type of commensal microbe can be fused in one or more positions along the length of the flexible tubular structure using pressure, heat, or a chemical. In an aspect, the method includes attaching the first material including the at least one microbe-promoting agent to the at least one anchor structure and attaching the second material to the at least one anchor structure.

In an aspect, the method further includes distributing on at least one surface of the second material at least one of a prebiotic agent, a therapeutic agent, or a bioactive agent, as shown in block 4860.

FIGS. 49-54 show block flow diagrams of a method for generating a gastrointestinal device with a layered wall encasing a plurality of at least one type of commensal microbe. FIG. 49 shows a flow diagram of a method including obtaining a gastrointestinal device, the gastrointestinal device including a flexible tubular structure formed from a first material, the flexible tubular structure including a proximal end and a distal end, the proximal end and the distal end forming a flow conduit through the flexible tubular structure; and at least one anchor structure including one or more gastric wall-engaging components configured to engage a wall of the gastrointestinal tract of a subject and hold the flexible tubular structure in place, in block 4900; distributing on one surface of the first material at least one microbe-promoting agent, in block 4910; and applying a second material over the at least one microbe-promoting agent to form a layered wall, the layered wall allowing an interaction the at least one microbe-promoting agent and at least one of an ingested product within the flexible tubular structure and a component of the gastrointestinal tract of the subject, in block 4920.

FIG. 50 shows further aspects of a method of generating a gastrointestinal device including a layered wall and at least one microbe-promoting agent. The method includes obtaining a gastrointestinal device. In an aspect, the method includes manufacturing the gastrointestinal device, as shown in block 5000. For example, the method can include manufacturing a bariatric sleeve such as described in U.S. Patent Application No. 2014/0012178 to Chin titled "Systems and Methods for Bariatric Therapy," which is incorporated herein by reference. In an aspect, the method includes using a commercially available gastrointestinal device.

The method includes distributing on one surface of the first material at least one microbe-promoting agent and applying a second material over the at least one microbe-promoting agent. In an aspect, at least one of the first material and the second material includes a semi-permeable material, as shown in block 5010. In an aspect, at least one of the first material and the second material includes a selectively permeable material. In an aspect, the selectively permeable material is selectively permeable based on size, hydrophobicity, or charge. Non-limiting examples of semi-permeable materials have been described above herein. In an aspect, the first material includes a first semi-permeable material and the second material includes a second semi-permeable material, as shown in block 5020. In an aspect, the first semi-permeable material differs from the second semi-permeable material, as shown in block 5030. For example, the first semi-permeable material can differ from the second semi-permeable material based on selectivity to size, hydrophobicity, or charge.

In an aspect, the method includes distributing on an inner surface of the first material the at least one microbe-promoting agent, the inner surface facing the flow conduit through the flexible tubular structure, as shown in block 5040. In an aspect, the method includes distributing on an outer surface of the first material the at least one microbe-promoting agent, the outer surface facing the wall of the gastrointestinal tract, as shown in block 5050.

The method includes distributing on one surface of the first material at least one microbe-promoting agent. In an aspect, the method includes coating the one surface of the first material with the at least one microbe-promoting agent, as shown in block 5060. In an aspect, coating includes spraying, dipping, or spreading a composition including the at least one microbe-promoting agent on the one surface of the first material. In an aspect, the method includes distributing on the one surface of the first material the at least one microbe-promoting agent in a coating material, as shown in block 5070. In an aspect, the coating material includes at least one of a degradable coating material, a matrix coating material, a fibrous coating material, a porous coating material, a gel coating material, or a mucus coating material, as shown in block 5080. In an aspect, the method includes distributing on the one surface of the first material the at least one microbe-promoting agent in a stimulus-responsive coating material, as shown in block 5090. In an aspect, the stimulus-responsive coating material includes at least one of a time-responsive coating material, a moisture-responsive coating material, a temperature-responsive coating material, a pH-responsive coating material, or a chemical-responsive coating material, as shown in block 5095.

FIG. 51 illustrates further aspects of a method such as shown in FIG. 49. In an aspect, the method includes in block 5100 binding to the one surface of the first material the at least one microbe-promoting agent. In an aspect, the method includes in block 5110 binding to the one surface of the first material the at least one microbe-promoting agent with at least one non-selective binding agent or selective binding agent. In an aspect, the at least one selective binding agent includes at least one of an antibody, a protein, a peptide, a DNA fragment, an RNA fragment, a lectin, or an aptamer, as shown in block 5120. In an aspect, the at least one non-selective binding agent includes at least one of an adhesive, an absorbent, an adsorbent, a gel, or a matrix, as shown in block 5130. Non-limiting examples of selective binding agents and non-selective binding agents have been described above herein.

In an aspect, the method includes in block 5140 impregnating into the one surface of the first material the at least one microbe-promoting agent. In an aspect, the method includes in block 5150 embedding into the one surface of the first material the at least one microbe-promoting agent. In an aspect, the method includes in block 5160 adsorbing, absorbing, covalently binding, or non-covalently binding onto the one surface of the first material the at least one microbe-promoting agent. In an aspect, the method further includes embedding the at least one microbe-promoting agent into the flexible tubular structure at the time of manufacture.

FIG. 52 shows further aspects of a method such as shown in FIG. 49. The method includes distributing on one surface of the first material at least one microbe-promoting agent. In an aspect, the at least one microbe-promoting agent is configured to promote at least one of attraction, colonization, and growth of at least one type of commensal microbe, as shown in block 5200. In an aspect, the at least one microbe-promoting agent is configured to promote at least one of attraction, colonization, and growth of at least one type of commensal gut microbe, as shown in block 5210. In an aspect, the at least one microbe-promoting agent is configured to promote at least one of attraction, colonization, and growth of at least part of a gut microbiota, as shown in block 5220. In an aspect, the at least one microbe-promoting agent is configured to promote at least one of attraction, colonization, and growth of at least one type of endogenous commensal microbe, as shown in block 5230. In an aspect, the at least one microbe-promoting agent is configured to promote at least one of attraction, colonization, and growth of at least one type of administered commensal microbe, as shown in block 5240. In an aspect, the at least one microbe-promoting agent is configured to promote at least one of attraction, colonization, and growth of at least one type of commensal microbe derived from a fecal sample, as shown in block 5250. In an aspect, the at least one microbe-promoting agent is configured to promote at least one of attraction, colonization, and growth of at least one type of genetically engineered microbe, as shown in block 5260. In an aspect, the at least one microbe-promoting agent is configured to promote at least one of attraction, colonization, and growth of at least one type of commensal microbe derived from in vitro culture, as shown in block 5270. In an aspect, the at least one microbe-promoting agent is configured to promote at least one of attraction, colonization, and growth of at least one type of probiotic, as shown in block 5280. In an aspect, the at least one microbe-promoting agent is configured to promote at least one of attraction, colonization, and growth of a phylogenetically diverse mini-microbiota, as shown in block 5290.

FIG. 53 shows further aspects of a method such as shown in FIG. 49. The method includes distributing on one surface of the first material at least one microbe-promoting agent. In an aspect, the at least one microbe-promoting agent is configured to promote at least one of attraction, colonization, and growth of at least one type of commensal microbe beneficial to the subject, as shown in block 5300. In an aspect, the at least one microbe-promoting agent is configured to promote at least one of attraction, colonization, and growth of at least one type of commensal microbe beneficial to at least one of the immune system of the subject, a dietary condition of the subject, or a medical condition of the subject, as shown in block 5310. In an aspect, the at least one microbe-promoting agent is configured to promote formation of a microbiome, as shown in block 5320. In an aspect, the at least one microbe-promoting agent includes at least one prebiotic agent, as shown in block 5330. In an aspect, the at least one microbe-promoting agent includes mucus, as shown in block 5340. In an aspect, the at least one microbe-promoting agent includes a binding agent, as shown in block 5350. In an aspect, the at least one binding agent includes at least one of a selective binding agent or a non-selective binding agent. In an aspect, the at least one microbe-promoting agent includes at least one lectin, as shown in block 5360. In an aspect, the at least one microbe-promoting agent includes at least one chemoattractant, as shown in block 5370. Non-limiting examples of microbe-promoting agents have been described above herein.

FIG. 54 shows further aspects of a method such as shown in FIG. 49. In an aspect, the method includes distributing on a surface of the first material at least one therapeutic agent, as shown in block 5400. In an aspect, the method includes distributing on a surface of the first material at least one bioactive agent, as shown in block 5410. Non-limiting examples of therapeutic agents and bioactive agents have been described above herein.

The method further includes applying a second material over the at least one microbe-promoting agent to form a layered wall, the layered wall allowing an interaction between the at least one microbe-promoting agent and an ingested product within the flexible tubular structure and/or a component of the gastrointestinal tract. In an aspect, the method includes applying a second material substantially identical to the first material, as shown in block 5420. In an aspect, the method includes applying a second material with a permeability property that differs from a permeability property of the first material, as shown in block 5430. In an aspect, the permeability property includes at least one of a sized-based permeability property, a charge-based permeability property, a pH-based permeability property, or a hydrophobicity-based permeability property, as shown in block 5440.

In an aspect, the method further includes attaching the first material including the at least one microbe-promoting agent to the second material. In an aspect, the method includes adhering (e.g., gluing) the first material to the second material. In an aspect, the method includes stapling the first material to the second material. In an aspect, the method includes stitching the first material to the second material. In an aspect, the method includes fusing the first material to the second material. For example, the first material including the at least one microbe-promoting agent can be fused in one or more positions along the length of the flexible tubular structure using pressure, heat, or a chemical. In an aspect, the method includes attaching the first material including the at least one microbe-promoting agent to the at least one anchor structure and attaching the second material to the at least one anchor structure.

In an aspect, the method further includes distributing on at least one surface of the second material at least one of a therapeutic agent and a bioactive agent, as shown in block 5450.

In an embodiment, a lumen-resident device includes a flexible tubular structure including an inner surface and an outer surface; a plurality of at least one type of commensal microbe associated with at least one of the inner surface and the outer surface of the flexible tubular structure; and a proximal end and a distal end, the proximal end and the distal end forming a flow conduit through the flexible tubular structure; and at least one anchor structure including one or more lumen wall-engaging components configured to engage a wall of a lumen of a subject. In an aspect, the lumen is a digestive tract of the subject. In an aspect, the lumen is an esophagus of the subject. In an aspect, the lumen is a respiratory tract of the subject. In an aspect, the lumen is a reproductive tract of the subject.

In an embodiment, a lumen-resident device includes an inner surface and an outer surface; at least one microbe-promoting agent associated with at least one of the inner surface and the outer surface of the flexible tubular structure, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more lumen wall-engaging components configured to engage a wall of a lumen of a subject. In an aspect, the lumen is a digestive tract of the subject. In an aspect, the lumen is an esophagus of the subject. In an aspect, the lumen is a respiratory tract of the subject. In an aspect, the lumen is a reproductive tract of the subject.

In an embodiment, a lumen-resident device includes a flexible tubular structure including a layered wall, the flexible tubular structure including a plurality of at least one type of commensal microbe encased in the layered wall, the layered wall configured to allow an interaction between the plurality of the at least one type of commensal microbe and a lumen of a subject, and a proximal end and a distal end, the proximal end and the distal end forming a flow conduit through the flexible tubular structure; and at least one anchor structure including one or more lumen wall-engaging components configured to engage a wall of a lumen of the subject. In an aspect, the layered wall of the flexible tubular structure includes an outer layer, an inner layer, and an internal space, the outer layer proximal to the wall of the lumen, the inner layer proximal to the flow conduit through the flexible tubular structure, and the internal space positioned between the outer layer and the inner layer and including the plurality of the at least one type of commensal microbe. In an aspect, at least one of the outer layer and the inner layer are formed from a semi-permeable material.

In an embodiment, a lumen-resident device includes a flexible tubular structure including a layered wall, the flexible tubular structure including at least one microbe-promoting agent encased in the layered wall, the at least one microbe-promoting agent configured to promote at least one of attraction, colonization, and growth of at least one type of commensal microbe; and a proximal end and a distal end, the proximal end and the distal end forming a flow conduit through the flexible tubular structure; and at least one anchor structure including one or more lumen wall-engaging components configured to engage a wall of the lumen of the subject. In an aspect, the layered wall of the flexible tubular structure includes an outer layer, an inner layer, and an internal space, the outer layer proximal to the wall of the lumen, the inner layer proximal to the flow conduit through the flexible tubular structure, and the internal space positioned between the outer layer and the inner layer and including the at least one microbe-promoting agent. In an aspect, at least one of the outer layer and the inner layer is formed from a semi-permeable material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "operably coupled to" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications can be made without departing from the subject matter described herein and its broader aspects and, therefore, the appended claims are to encompass within their scope all such changes and modifications as are within the true spirit and scope of the subject matter described herein.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Various non-limiting embodiments are described herein as Prophetic Examples.

Prophetic Example 1: An Implanted Gastrointestinal Device Including a Semipermeable Sleeve with Microbes to Treat an Inflammatory Bowel Disease An implanted gastrointestinal device with a flexible tubular structure, e.g., a semipermeable sleeve, is designed to treat patients with an inflammatory bowel disease (IBD) and resulting inflamed section of colon. The implanted gastrointestinal device comprises a semipermeable sleeve, which is anchored in the transverse colon, extending distally for 20 cm. The inside surface of the semipermeable sleeve is coated with a set of microbes that approximates the microbiota at the site in a healthy subject and aids in protecting the inflamed section of the transverse colon of an IBD patient, providing microbial functions at the site and replenishing the microbiota of nearby tissues. The outside surface of the semipermeable sleeve is coated with a set of microbes for replenishing the microbiota of the affected side and nearby tissues.

The semipermeable sleeve is constructed to extend from an anchor point in the transverse colon distally for 20 cm, covering a length of the colon that includes a site of inflamed tissue of a patient with IBD. The semipermeable sleeve is formed from a biocompatible semipermeable membrane, for example, polyethylene-co-vinyl acetate (PEVA) (available from Polysciences, Inc., Warrington, Pa.; see PEVA info sheet). Methods and materials to manufacture semipermeable membranes with a desired porosity and physical properties (e.g., flexibility, tensile strength and biocompatibility) are described (see e.g., Handbook of Membrane Separations: Chemical, Pharmaceutical, Food, and Biotechnological Applications, edited by Anil K. Pabby, Syed S. H. Rizvi, Ana Maria Sastre, 2009, CRC Press, Boca Raton, Fla., which is incorporated herein by reference). The semipermeable sleeve formed from the biocompatible semipermeable membrane includes pores approximately 20 μm in diameter. The sleeve is anchored at its proximal end in the proximal transverse colon. During digestion, chyme enters the proximal end of the device and proceeds through the lumen of the device to the distal end. Select nutrients, micronutrients, vitamins, compounds, and water pass through the semipermeable membrane (i.e., 20 μm pores) to be absorbed by the intestinal wall.

The anchor at the proximal end of the device holds the semipermeable sleeve in place in the intestine and allows the flow of chyme down the lumen of the sleeve. The anchor structure is cast from PEV at the time of device manufacture, and is shaped like an umbrella that expands after implanting the device by colonoscopy. Anchors to retain intestinal sleeves in the gastrointestinal tract are described (see e.g., U.S. Patent Appl. No. 2013/0281911 by Babkes et al. published on Oct. 24, 2013, which is incorporated herein by reference).

The inner surface of the semipermeable sleeve of the gastrointestinal device is coated with microbes that are normally associated with a healthy transverse colon. The microbes include Firmicutes (including at least one *Lactobacillus*), Bacteroidetes, Actinobacteria (including *Bifidobacterium*) and/or Proteobacteria in a desired ratio that is determined based on data including the patient's characteristics such as age, ethnicity, and location, as well as population data. The microbes function as they would in a healthy colon by further digesting the chyme to release nutrients and prepare the chyme for downstream digestion. The microbes further aid in re-establishing and replenishing microbes at the affected site as well as nearby and downstream regions of the colon. The microbes are encapsulated in a coating to support continued health of the microbes and to allow exposure to the chyme. The coating is formed of a hydrogel made of a synthetic monomer, for example polyethylene glycol diacrylate/dimethacrylate (PEGDA/PEGDMA), as described in Lin & Metters (2006), ibid, and includes the synthetic mucin MUC2.

The outer surface of the semipermeable sleeve of the gastrointestinal device is coated with degradable coating that can release microbiota over time. For example, PLGA (polylactic coglycolic acid) may be used to encapsulate the commensal microbes and to coat the regions of the outer surface of the sleeve. Fabrication techniques and polymer compositions for PLGA biodegradable carriers are described (see e.g., Makadia et al., *Polymers* 3:1377-1397, 2011, which is incorporated herein by reference). The ratio of lactic acid to glycolic acid in the PLGA is adjusted to control the rate of PLGA degradation and release of the microbes. For example PLGA composed of 85% lactic acid and 15% glycolic acid biodegrades and releases its contents starting on day 22 following implantation and completes release by approximately day 110 (see e.g., Makadia et al., Ibid.). Microbes needed to reestablish a healthy microbiome for IBD patients may be identified for individual patients or from group studies. IBD patients display abnormal microbiota, or dysbiosis, with depletion of some phyla and overrepresentation of others. For example, IBD patient's microbiota may contain elevated numbers of injurious bacteria belonging to Proteobacteria and Actinobacteria phyla while protective bacteria from Firmicutes are underrepresented (see e.g., Wu and Lewis, *Clin. Gastroent. Hepatol.* 11:774-777, 2013, which is incorporated herein by reference). Thus, the intestinal sleeve is coated on the outer surface (facing the intestinal wall) with PLGA containing Firmicutes *Fecalibacterium prauzsnitzii*.

Prophetic Example 2: A Gastrointestinal Device with Fecal Microbiota for Treatment of Recurrent *Clostridium difficile* Infection An implantable gastrointestinal device is manufactured with microbes isolated from fecal transplants embedded in a semipermeable, degradable polymer, and used to treat recurrent or relapsing *Clostridium difficile* infections (CDI). The gastrointestinal device includes a flexible tubular structure formed from a biodegradable polymer, which degrades and releases fecal microbes. The device is designed as a flexible tube with an anchor at the proximal end that holds the device in the colon until it undergoes biodegradation and is excreted. The intestinal sleeve is designed to provide beneficial fecal microbiota to reestablish a healthy microbiome and correct dysbiosis seen in CDI.

The flexible tubular structure is manufactured from a biodegradable polymer as a flexible sleeve with an expandable anchor structure at the proximal end. The sleeve may be formed from a degradable polymer by casting or extrusion as a thin walled tube approximately 25 cm long with a diameter of approximately 20 mm. Semipermeable, biodegradable polymers are described (see, e.g., Pal et al., *Designed Monomers and Polymers* 12:197-220, 2009, which is incorporated herein by reference). The rate of degradation of a copolymer may be controlled by adjusting the molar ratio of the monomers (see, e.g., Makadia et al., *Polymers* 3:1377-1397, 2011 and Kong, et al., *Biomacromolecules* 5:1720-1727, 2004, which are incorporated herein by reference). For example, a copolymer composed of 85% lactic acid and 15% glycolic acid biodegrades and releases its contents starting on day 22 following implantation and completes release by approximately day 110 (see e.g., Makadia et al., Ibid.). The anchor structure at the proximal end of the sleeve is also fabricated from a biodegradable polymer that degrades over several months. The anchor structure expands to attach to the intestinal wall in the ascending colon after implantation of the device. Manufacture of expanding anchors from polymers is described (see, e.g., U.S. Patent Appl. No. 2013/0281911 by Babkes et al. published on Oct. 24, 2013 which is incorporated herein by reference). The anchor degrades after approximately 4 months and any remaining fragments are excreted.

The gastrointestinal device is manufactured with fecal microbiota embedded in the biodegradable sleeve. Fecal material is obtained from healthy donors and prepared by dilution, homogenization, and filtration according to established protocols (see e.g., Bakken et al., *Clin. Gastroenterol. Hepatol.* 9:1044-1049, 2011, which is incorporated herein by reference).

Fecal microbiota donors are screened for HIV, Hepatitis B or Hepatitis C infections, risky behavior, exposure to traveler's diarrhea, Creutzfeldt-Jakob disease, gastrointestinal disease (e.g., IBD, chronic diarrhea or constipation), and factors that may affect an individual's microbiome (e.g., antibiotics, and immunosuppressive medications such as glucocorticoids, biologics). Microbiota donors are excluded if they have had gastric bypass surgery, metabolic syndrome, systemic autoimmunity, atopic disease, or fibromyalgia. Also donor stools are tested for *Clostridium difficile* toxins by PCR or immunoassay, enteric pathogens, fecal *Giardia* antigen, and *Cryptosporidium*.

Fecal microbes are obtained from stool samples and incorporated in a biocompatible polymer used for making the gastrointestinal device. Fecal microbes are obtained from approximately 50 grams of feces using a combination of dilution in saline, homogenization, filtration and centrifugation. The microbes are concentrated and suspended in 10% glycerol in saline and stored frozen at −80 degrees C. Microbe sample aliquots obtained from 50 grams of feces are typically used for a fecal transplant (see, e.g., Hamilton et al., *Gut Microbes* 4:125-135, 2013, which is incorporated herein by reference). However, a gastrointestinal device containing embedded microbes may contain multiple aliquots of microbes to be released from the device over an extended period, e.g., 110 days. The gastrointestinal device is constructed with fecal microbiota embedded in sodium alginate. Methods to extrude alginate and to encapsulate intestinal bacteria in alginate are described (see e.g., Lotfipour et al., *Advanced Pharmaceutical Bulletin* 2:71-78, 2012, which is incorporated herein by reference). Moreover, the rate of degradation of alginate hydrogels can be modified using oxidized, low MW alginates. The degradation rate of alginate hydrogels for in vivo use is altered to deliver microbes on a preferred timescale without changing elasticity or gel formation (see, e.g., Kong, et al., *Biomacromolecules* 5:1720-1727, 2004, which is incorporated herein by reference). The intestinal sleeve may be fabricated with layers of different alginate hydrogels having different degradation rates. For example, following implantation of the intestinal sleeve, the outer layer of alginate may degrade and release fecal microbes from days 7-10, and then an inner layer may degrade at a later time, e.g., from days 30-36.

The gastrointestinal device with embedded fecal microbes is implanted by colonoscopy with the expandable anchor structure compressed until it reaches the ascending colon. Expansion of the anchor structure retains the proximal end of the intestinal sleeve in the ascending colon and allows excretion through the flexible tube, release of microbes adjacent to the colon mucosa, and exchange of water and metabolites across the semipermeable sleeve. Implantation of intestinal sleeves is described (see e.g., U.S. Patent Appl. No. 2013/0281911, ibid.)

Prophetic Example 3: Gastrointestinal Device Includes an Impermeable Flexible Tubular Structure with Microbial Coating to Treat Obese Patients A gastrointestinal device is described that includes a flexible tubular structure formed from an impermeable membrane and microbial coatings to treat obese patients. The impermeable flexible tubular structure restricts caloric intake by preventing digestion and absorption of nutrients until they have passed the duodenum. The microbial coating on the inside surface supplies microbes that function in place of the natural flora that normally reside in the section of the digestive tract covered by the gastrointestinal device The microbial coating on the outside surface supplies microbes to promote a healthy microbiome. The microbial coating on the outside surface includes a degradable polymer that releases microbes in a time-dependent fashion.

The gastrointestinal device includes a flexible tubular structure composed of an impermeable membrane and includes an anchor structure at the proximal end and a microbial coating. A biocompatible polymer, for example expanded polytetrafluoroethylene (ePTFE), with a thickness of approximately 0.001 inches is used to make a sleeve about 25 cm in length with a diameter ranging between 10 mm and 35 mm. The sleeve extends from the stomach through the pyloric sphincter and through the duodenum to the jejunum. Methods to manufacture a cylindrical flexible tube have been described. For example, an impermeable intestinal sleeve may be made by extrusion of ePTFE into a tube form and expansion of sections to fill differing intestinal diameters (see e.g., U.S. Patent Application No. 2012/0184893 by Thompson et al. published on Jul. 19, 2012, which is incorporated herein by reference). The intestinal sleeve is constructed with an expandable anchor at the proximal end which retains the proximal end of the sleeve in the stomach. The expandable anchor fabricated out of a polymer, (e.g., PTFE) is approximately 12 mm to 60 mm in outside diameter with an internal opening about 2 mm to 20 mm in diameter. Methods to manufacture the expandable anchor, which may include laser cutting, and heat setting are described (see e.g., U.S. Patent No. 2012/0184893, ibid.). The gastrointestinal device is designed to be implanted and deployed using endoscopic techniques (see, e.g., U.S. Patent Appl. No. 2013/0281911, ibid.)

The inner surface of the semipermeable sleeve of the gastrointestinal device is coated with microbes that are normally associated with a healthy gut, as described below, and may include *Clostridium, Streptococcus, Escherichia*, Firmicutes, Bacteroidetes, Actinobacteria and/or Proteobacteria. The microbes are arranged along the inside surface in a gradient of changing ratio that reflect the changes along the normal digestive lumen at the site of implantation. The ratios can be determined based on data including the patient's characteristics such as age, ethnicity, and location, as well as population data. The microbes function as they would in a healthy intestine by digesting the chyme and preparing it for further processing downstream. The microbes are encapsulated in a coating to support continued health of the microbes and to allow exposure to the chyme. The coating is formed of a hydrogel made of a synthetic monomer, for example polyethylene glycol diacrylate/dimethacrylate (PEGDA/PEGDMA), as described in Lin & Metters (2006), ibid, and includes the synthetic mucin MUC2.

Microbes are coated on the outside surface of the flexible tubular structure in a degradable polymer designed to release microbes into the intestinal lumen to correct imbalances in microbiota associated with obesity and metabolic dysfunction. Microbiome changes at the level of bacterial phyla, (e.g., reduced numbers of Bacteroidetes and increased numbers of Firmicutes) are associated with obesity and metabolic dysfunction (see e.g., Tilg and Kaiser, *J. Clin. Invest.* 121:2126-2132, 2011 which is incorporated herein by reference). Conversely weight loss in obese animals is associated with increased populations of Proteobacteria (*Escherichia*) and Verrucomicrobia (see e.g., Cox and Blaser, *Cell Metab.* 17:883-894, 2013, which is incorporated herein by reference). Thus to treat obese patients, the microbial coating contains, for example, $10^6$ to $10^{10}$ Bacteroidetes, Proteobacteria and Verrrucomicrobia, which are suspended in a biocompatible, degradable polymer, e.g., PLGA (polylactic coglycolic acid) and coated onto the outer surface of the intestinal sleeve. Administration and dosing of microbes are described (see, e.g., U.S. Pat. No. 7,101,565 to Monte titled "Probiotic/Prebiotic Composition and Delivery Method," which is incorporated herein by reference). Fabrication techniques and polymer compositions for PLGA degradable carriers are described (see e.g., Makadia et al., *Polymers* 3:1377-1397, 2011, which is incorporated herein by reference). The ratio of lactic acid to glycolic acid in the PLGA is adjusted to control the rate of PLGA degradation and release of the bacteria. For example PLGA composed of 85% lactic acid and 15% glycolic acid biodegrades and releases its contents starting on day 22 following implantation, and completes release by approximately day 110 (see e.g., Makadia et al., Ibid.).

Microbes localized to specific portions of the intestine may be coated on select portions of the intestinal sleeve in corresponding locations. For example, preferred microbes found in the small intestine of healthy subjects are coated on the inside and/or outside surface of the flexible tubular structure in regions that will line the small intestine or subsections of the small intestine, e.g., jejunum, ileum, duodenum. For example, dominant phylogenetic groups present in the small intestine include *Clostridium* sp., *Streptococcus* sp. and *Escherichia* sp., which are adapted to the acidity and bile components present in the small intestine (see e.g., Zoetendal et al., *ISME Journal* 6:1415-1426, 2012, which is incorporated herein by reference). Microbes associated with a healthy mucosal microbiome may be coated on the intestinal sleeve at increasing distances from the proximal end, i.e. the anchor structure, to deliver microbes to the mucosa of the duodenum, jejunum or ileum when the sleeve is implanted and extended from the pyloric valve to the small intestine. For example, *Clostridium* sp. may be coated on the outer sleeve approximately 20 cm from the proximal end to deliver *Clostridium* sp., to the jejunum once the device is implanted, as well as on the inner surface of the sleeve to provide microbial function to the device lumen. Methods and apparatus to determine gastrointestinal locations, e.g., distances from pylorus to: jejunum, or to ileum, or to colon are described (see e.g., Zoetendal et al., Ibid.).

Moreover, different microbes may be coated on different portions of the flexible tubular structure to provide selected microbes to specific locations in the intestine distal to the device. For example, Bacteriodetes may be coated distal to *Clostridium* sp. on the flexible tubular structure to provide delivery of Bacteriodetes to the colon and *Clostridium* sp. to the jejunum once the device is implanted.

Prophetic Example 4: An Implanted Gastrointestinal Device with a Semipermeable Sleeve and Prebiotics to Treat Inflammatory Bowel Disease An implanted gastrointestinal device with a flexible tubular structure formed from a semipermeable material is designed to treat patients with inflammatory bowel disease (IBD) and resulting inflamed section of colon. The implanted gastrointestinal device comprises a flexible semipermeable tube which is anchored in the transverse colon, extending distally for 20 cm. The flexible tubular structure is coated with at least one microbe-promoting agent to promote attraction, colonization, and growth of commensal microbes. The semipermeable sleeve with at least one microbe-promoting agent provides protection to the inflamed tissue while allowing some compounds to pass through for absorption, and provides an environment for commensal microbes to colonize and thereby provide microbial function at the implantation site and aids in replenishing the microbiota of nearby tissues.

The flexible, semipermeable tube is constructed to extend from an anchor point in the transverse colon distally for 20 cm, covering a length of the colon that includes a site of inflamed tissue of a patient with an inflammatory bowel disease, e.g., Crohn's disease. The flexible tube is a biocompatible semipermeable membrane, constructed from, for example, polyethylene-co-vinyl acetate (PEVA) as described above herein. A flexible tube containing a membrane with pores approximately 20 μm in diameter is anchored with its proximal end in the proximal transverse colon. Select nutrients, micronutrients, vitamins, compounds, and water pass through the semipermeable membrane (i.e., 20 μm pores) to be absorbed by the intestinal wall. The gastrointestinal device is held in place with an anchor structure is cast from PEV at the time of device manufacture, and is shaped like an umbrella that expands after implantation of the device. Anchors to retain intestinal sleeves in the gastrointestinal tract are described (see e.g., U.S. Patent Appl. No. 2013/0281911 by Babkes et al. published on Oct. 24, 2013, which is incorporated herein by reference).

The inner surface of the semipermeable sleeve of the gastrointestinal device is coated with microbe-promoting agents that promote the attraction, colonization, and growth of commensal microbes that are normally associated with a healthy transverse colon. The microbes within the device can then function as they would in a healthy colon by further digesting the chyme to release nutrients and prepare the chyme for downstream digestion. The microbes further aid in re-establishing and replenishing microbes at the affected site as well as nearby and downstream regions of the colon. The microbe-promoting agents are encapsulated in a coating to support continued health of the microbes and to allow exposure to the chyme. The coating is formed of a hydrogel made of a synthetic monomer, for example polyethylene glycol diacrylate/dimethacrylate (PEGDA/PEGDMA), as described in Lin & Metters (2006). Microbe-promoting agents encapsulated in the hydrogel can include at least one chemoattractant, e.g., serine or alpha-methyl-DL-aspartate, for attraction; prebiotics and nutrients for bacterial growth, as described below; and matrix proteins, including mucins, for support. Microbe-promoting agents can include bacterial or mammalian cells, e.g., goblet cells and/or genetically engineered cells, that provide the promoting environment and/or produce the chemoattractant, growth nutrients, or matrix proteins. Microbe-promoting agents are chosen and distributed in a pattern on the semipermeable sleeve depending on the microbial distribution desired based on informational data regarding the patient, such as age, gender, and diet, as well as on populational data. Degradable coatings as described below can be included in the coating of the inner sleeve to release a microbe-promoting agent, e.g., a chemoattractant.

The outer surface of the flexible tubular structure is coated with at least one microbe-promoting agent, for example at least one prebiotic agent, to restore a healthy microbiome to the intestine of the IBD patient. Degradable coatings that release prebiotic agents over time into the intestine are used to coat the outside surface of the intestinal sleeve. For example, PLGA (polylactic coglycolic acid) may be used to encapsulate prebiotics and to coat the outer surface of the sleeve. Fabrication techniques and polymer compositions for PLGA biodegradable carriers are described (see e.g., Makadia et al., *Polymers* 3:1377-1397, 2011, which is incorporated herein by reference). The ratio of lactic acid to glycolic acid in the copolymer, PLGA, is adjusted to control the rate of PLGA degradation and release of the prebiotic agents. For example PLGA composed of 85% lactic acid and 15% glycolic acid biodegrades and releases its contents starting on day 22 following implantation and completes release by approximately day 110 (see e.g., Makadia et al., Ibid.

The microbe-promoting agents coating the inner surface and outer surface of the flexible tubular structure include prebiotic agents to promote growth of preferred microbes in the endogenous microflora, as well as orally administered bacteria of the Firmicutes species. The prebiotics oligofructose and inulin are carbohydrates that promote the growth of preferred bacteria and lead to production of short chain fatty acids (e.g., butyric acid), which reduce inflammation. For example, PLGA containing oligofructose and inulin is distributed on the inner wall and the outer wall of the flexible, semipermeable tube to promote the growth of beneficial bacteria (e.g., *Lactobacilli* and *Bifidobacteria*) and to stimulate the production of butryric acid, which reduces inflammation in the colonic mucosa (see e.g., Damaskos and Kollos, *Brit. J. Clin. Pharm.* 65:453-467, 2008, which is incorporated herein by reference).

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A gastrointestinal device comprising:
   a flexible tubular structure sized for placement in a portion of the gastrointestinal tract of a subject and including
   an inner surface and an outer surface;
   a proximal end and a distal end, the proximal end and the distal end forming a flow conduit through the flexible tubular structure;
   a stimulus-responsive degradable material associated with at least one of the inner surface and the outer surface of the flexible tubular structure, the stimulus-responsive degradable material responsive to an ingested chemical carried in chyme; and
   a plurality of at least one type of commensal microbe embedded in the stimulus-responsive degradable material associated with the at least one of the inner surface and the outer surface of the flexible tubular structure; wherein the at least one type of commensal microbe is releasable from the stimulus-responsive degradable material in response to the ingested chemical carried in the chyme; and wherein the plurality of the at least one type of commensal microbe embedded in the stimulus-responsive degradable material forms an artificial microbiota, wherein a type and a distribution of the plurality of the at least one type of commensal microbe along a length of the flexible tubular structure is substantially identical to a type and a distribution of one or more endogenous microbes associated with the portion of the gastrointestinal tract of the individual for which the flexible tubular structure is sized; and
   at least one anchor structure attached to the flexible tubular structure and including one or more gastric wall-engaging components configured to engage a wall of the gastrointestinal tract of a subject.

2. The device of claim 1, wherein the stimulus-responsive degradable material and the plurality of the at least one type of commensal microbe embedded therein are associated with the outer surface of the flexible tubular structure; and the flexible tubular structure is formed from a sheet of semi-permeable material that is selectively permeable to the ingested chemical carried in the chyme.

3. The device of claim 1, wherein the flexible tubular structure is formed from a sheet of degradable material.

4. The device of claim 1, wherein the flexible tubular structure is formed from two or more noncontiguous segments attached to one another through at least one degradable linker.

5. The device of claim 1, wherein the plurality of the at least one type of commensal microbe embedded in the stimulus-responsive degradable material includes a plurality of at least one type of gut microbe embedded in the stimulus-responsive degradable material.

6. The device of claim 1, wherein the plurality of the at least one type of commensal microbe embedded in the stimulus-responsive degradable material includes a plurality of at least one type of genetically modified microbe embedded in the stimulus-responsive degradable material.

7. The device of claim 1, wherein the plurality of the at least one type of commensal microbe embedded in the stimulus-responsive degradable material includes a plurality of at least one type of commensal microbe from a fecal sample embedded in the stimulus-responsive degradable material.

8. The device of claim 1, wherein the plurality of the at least one type of commensal microbe embedded in the stimulus-responsive degradable material includes at least part of a gut microbiota embedded in the stimulus-responsive degradable material.

9. The device of claim 1, wherein the plurality of the at least one type of commensal microbe includes at least one first type of commensal microbe embedded in the stimulus-responsive degradable material on at least one first portion of the flexible tubular structure and at least one second type of commensal microbe embedded in the stimulus-responsive degradable material on at least one second portion of the flexible tubular structure.

10. The device of claim 1, wherein the plurality of the at least one type of commensal microbe embedded in the stimulus-responsive degradable material forms a gradient of microbes on the at least one of the inner surface and the outer surface of the flexible tubular structure, wherein the gradient of microbes on the at least one of the inner surface and the outer surface of the flexible tubular structure is substantially identical to at least a portion of an endogenous gradient of microbes associated with the portion of the gastrointestinal tract of the individual for which the flexible tubular structure is sized.

11. The device of claim 1, wherein the plurality of the at least one type of commensal microbe embedded in the stimulus-responsive degradable material includes at least one type of probiotic embedded in the stimulus-responsive degradable material.

12. The device of claim 1, wherein the stimulus-responsive degradable material and the plurality of the at least one type of commensal microbe embedded therein form a coating on the at least one of the inner surface and the outer surface of the flexible tubular structure.

13. The device of claim 1, further comprising a plurality of at least one first type of commensal microbe embedded in a first stimulus-responsive degradable material responsive to a first ingested chemical carried in the chyme and a plurality of at least one second type of commensal microbe embedded in a second stimulus-responsive degradable material responsive to a second ingested chemical carried in the chyme.

14. The device of claim 1, further comprising at least one prebiotic agent in a degradable coating associated with at least one of the inner surface and the outer surface of the flexible tubular structure.

15. The device of claim 1, further comprising at least one therapeutic agent in a degradable coating associated with at least one of the inner surface and the outer surface of the flexible tubular structure.

16. The device of claim 15, wherein the therapeutic agent includes an antimicrobial agent, an anti-inflammatory agent, a muscle relaxant, an anti-spasmodic agent, or an analgesic in a degradable coating associated with at least one of the inner surface and the outer surface of the flexible tubular structure.

17. The device of claim 1, further comprising at least one bioactive agent in a degradable coating associated with at least one of the inner surface and the outer surface of the flexible tubular structure.

18. The device of claim 17, wherein the bioactive agent includes a digestive enzyme or a hormone in a degradable coating associated with at least one of the inner surface and the outer surface of the flexible tubular structure.

19. The device of claim 1, wherein the one or more gastric wall-engaging components include one or more barbs or one or more hooks.

20. The device of claim 1, wherein the one or more gastric wall-engaging components include at least one of an adhesive or an adherent.

21. The device of claim 1, wherein the at least one anchor structure is at least one of inflatable or expandable.

22. The device of claim 1, wherein the flexible tubular structure is a sleeve.

23. The device of claim 1, wherein the flexible tubular structure is formed from a sheet of the stimulus-responsive degradable material and the plurality of the at least one type of commensal microbe is embedded therein.

24. The device of claim 1, wherein the flexible tubular structure is formed from a sheet of semi-permeable material that is laterally and bi-directionally semi-permeable from one of the inner surface or the outer surface of the flexible tubular structure through to the other of the inner surface or the outer surface of the flexible tubular structure permeable; and wherein the sheet of semi-permeable material is selectively permeable to at least one of a subset of ingested molecules, a subset of endogenous gastrointestinal molecules, or a combination thereof.

25. The device of claim 1, wherein the stimulus-responsive degradable material includes a hydrogel responsive to the ingested chemical carried in the chyme.

26. The device of claim 1, wherein the stimulus-responsive degradable material is responsive to ingested glucose carried in the chyme.

27. The device of claim 1, wherein the stimulus-responsive degradable material is responsive to an ingested protein carried in the chyme.

28. The device of claim 1, wherein the stimulus-responsive degradable material is responsive to an ingested antibody carried in the chyme.

29. The device of claim 1, wherein the stimulus-responsive degradable material is responsive to an ingested aptamer carried in the chyme.

30. A method comprising:
distributing a stimulus-responsive degradable material and a plurality of at least one type of commensal microbe on at least one of an inner surface and an outer surface of a flexible tubular structure sized for placement in a portion of the gastrointestinal tract of a subject to form an artificial gut microbiota, wherein the plurality of the at least one type of commensal microbe is embedded in the stimulus-responsive degradable material, and wherein the stimulus-responsive degradable material is responsive to an ingested chemical carried in chyme, a type and a distribution of the plurality of the at least one type of commensal microbe along a length of the flexible tubular structure distributed to mirror a type and a distribution of one or more endogenous microbes associated with the portion of the gastrointestinal tract of the individual for which the flexible tubular structure is sized.

31. The method of claim 30, further comprising:
distributing the stimulus-responsive degradable material and the plurality of the at least one type of commensal microbe on the outer surface of a flexible tubular structure formed from a sheet of semi-permeable material, wherein the plurality of the at least one type of commensal microbe is embedded in the stimulus-responsive degradable material, and wherein the semi-permeable material is selectively permeable to the ingested chemical carried in the chyme.

32. The method of claim 30, wherein the plurality of the at least one type of commensal microbe embedded in the stimulus-responsive degradable material includes at least part of a healthy gut microbiota.

* * * * *